United States Patent
Hong et al.

(10) Patent No.: US 11,118,184 B2
(45) Date of Patent: Sep. 14, 2021

(54) ASYMMETRIC SIRNA FOR INHIBITING EXPRESSION OF MALE PATTERN HAIR LOSS TARGET GENE

(71) Applicant: OliX Pharmaceuticals, Inc., Gyeonggi-do (KR)

(72) Inventors: Sun Woo Hong, Gyeonggi-do (KR); Jihye Hwang, Gyeonggi-do (KR)

(73) Assignee: OLIX PHARMACEUTICALS, INC., Gyeonggi-Do (KR)

( * ) Notice: Subject to any disclaimer, the term of this patent is extended or adjusted under 35 U.S.C. 154(b) by 26 days.

(21) Appl. No.: 16/486,833

(22) PCT Filed: Feb. 21, 2018

(86) PCT No.: PCT/KR2018/002103
§ 371 (c)(1),
(2) Date: Aug. 18, 2019

(87) PCT Pub. No.: WO2018/155890
PCT Pub. Date: Aug. 30, 2018

(65) Prior Publication Data
US 2019/0382771 A1    Dec. 19, 2019

(30) Foreign Application Priority Data

Feb. 21, 2017    (KR) .................. 10-2017-0022909

(51) Int. Cl.
*C12N 15/113*    (2010.01)
*C12Q 1/68*    (2018.01)

(52) U.S. Cl.
CPC ...... *C12N 15/1137* (2013.01); *C12N 15/1138* (2013.01); *C12Q 1/68* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 2005/0164970 A1* | 7/2005 | Li | C12N 15/1138 514/44 R |
| 2009/0282496 A1* | 11/2009 | Chang | A61K 31/16 800/18 |
| 2012/0238017 A1* | 9/2012 | Lee | A61P 43/00 435/375 |
| 2014/0322243 A1* | 10/2014 | Salhia | C12Q 1/6886 424/174.1 |
| 2015/0197756 A1* | 7/2015 | Brown | A61P 1/16 514/44 A |
| 2015/0284717 A1* | 10/2015 | Templin | C12Y 103/99005 514/44 A |
| 2019/0336520 A1* | 11/2019 | Cabon | C12N 15/1138 |

FOREIGN PATENT DOCUMENTS

| | | |
|---|---|---|
| JP | 2011-120589 A | 6/2011 |
| KR | 20090065880 A | 6/2009 |
| KR | 20110049733 A | 5/2011 |
| KR | 20120042645 A | 5/2012 |
| WO | 2005045037 A2 | 5/2005 |
| WO | WO2009078685 A2 | 6/2009 |
| WO | 2012006241 A2 | 1/2012 |

OTHER PUBLICATIONS

Chang et al., Molecular Therapy vol. 17(4)725-732, Apr. 2009.*
Azzouni, F., et al., "The 5 Alpha-Reductase Isozyme Family: A Review of Basic Biology and Their Role in Human Diseases", "Advances in Urology", 2012, pp. 1-18.
Chhipa, R.R., et al., "The Direct Inhibitory Effect of Dutasteride or Finasteride on Androgen Receptor Activity is Cell Line Specific", "Prostate", Oct. 2013, pp. 1483-1494, vol. 73, No. 14.
Genbank, "Predicted: Ailuropoda Melanoleuca Androgen Receptor (AR), mRNA", "Genbank: NCBI Reference Sequence: XM_002929171.3", Dec. 28, 2016, pp. 1-2.
Winiarska, A., et al., "Effect of 5 alpha-Dihydrotestosterone and Testosterone on Apoptosis in Human Dermal Papilla Cells", "Skin Pharmacol. Physiol.", 2006, pp. 311-321, vol. 19.
Chang, C., et al., "The Design, Preparation, and Evaluation of Asymmetric Smalll Interfering RNA for Specific Gene Silencing in Mammalian Cells", "Methods in Molecular Biology", 2013, pp. 135-152, vol. 942, Publisher: Springer Science+Business Media, LLC.
Socheata, L., et al., "Visualization of self-delivering hydrophobically modified siRNA cellular internalization", "Nucleic Acids Research", 2017, pp. 15-25, vol. 45, No. 1.
Dugour, A., et al., "Silencing the androgen receptor: New skills for antiandrogen oligonucleotide skin and hair therapy", Journal of Dermatological Science, May 1, 2009, pp. 123-125, vol. 54, No. 2, Publisher: Elsevier.

* cited by examiner

Primary Examiner — Sean McGarry
(74) Attorney, Agent, or Firm — Hultquist, PLLC; Steven J. Hultquist

(57) ABSTRACT

The present invention relates to an asymmetric siRNA which inhibits an expression of male pattern hair loss target genes and a use thereof and, more particularly, to an asymmetric siRNA which inhibits an expression of 3-oxo-5-alpha-steroid-4-dehydrogenase 1 (SRD5A1) gene, 3-oxo-5-alpha-steroid-4-dehydrogenase 2 (SRD5A2) gene or androgen receptor (AR) gene, and a composition for prevention or treatment of hair loss comprising the asymmetric siRNA.

6 Claims, 12 Drawing Sheets
Specification includes a Sequence Listing.

ASYMMETRIC SIRNA FOR INHIBITING EXPRESSION OF MALE PATTERN HAIR LOSS TARGET GENE

CROSS-REFERENCE TO RELATED APPLICATIONS

This application is a U.S. national phase under the provisions of 35 U.S.C. § 371 of International Patent Application No. PCT/KR18/02103 filed Feb. 21, 2018, which in turn claims priority of Korean Patent Application No. 10-2017-0022909 filed Feb. 21, 2017. The disclosures of International Patent Application No. PCT/KR18/02103 and Korean Patent Application No. 10-2017-0022909 are hereby incorporated herein by reference in their respective entireties, for all purposes.

TECHNICAL FIELD

The present invention relates to asymmetric siRNA for inhibiting the expression of a target gene for male pattern hair loss and a use thereof, and more particularly to asymmetric siRNA for inhibiting the expression of the 3-oxo-5-alpha-steroid 4-dehydrogenase 1 (SRD5A1) gene, the 3-oxo-5-alpha-steroid 4-dehydrogenase 2 (SRD5A2) gene, or the androgen receptor (AR) gene, and a composition for preventing or treating hair loss which comprises the asymmetric siRNA.

BACKGROUND ART

Human hair is formed in hair follicles. There are papillae in the hair follicles, small blood vessels are distributed in the papillae to supply nutrients necessary for hair growth, and sebaceous glands are distributed on the upper ends of side surfaces of the papillae to secrete sebum to protect the hair. The dermal papilla regulates hair growth and is the site where male hormones act in male-pattern hair loss. The hair matrix is a site where cell division occurs under the control of the dermal papilla and hair grows.

The main factor of male hair loss is due to the effect of abnormal hormones. At puberty, sex hormones are actively secreted and the secondary sexual character appears. These changes are caused by sex hormones, i.e., androgens (male hormones) and estrogens (female hormones). Androgens develop body hair under the eyebrows, and estrogen mainly promotes hair growth. For men, hair loss is due to excessive secretion of androgens which results in inhibition of the action of estrogen by the excessively secreted androgens.

Specifically, steroid 5-alpha reductase is involved in the male hair loss mechanism by male hormones, and steroid 5-alpha reductase is a main enzyme that reduces testosterone, which is a male hormone, to DHT (dihydrotestosterone). The resulting DHT is known to bind to an androgen receptor to thereby regulate hair growth in the hair follicles and be involved in the proliferation of sebaceous glands.

The androgen receptor is a male hormone (androgen) receptor and is known to be capable of binding to both testosterone and DHT, but have a stronger binding affinity with DHT. It is known that the inhibition of steroid 5-alpha reductase and an androgen receptor increases hair growth factors and induces hair growth, whereas the activation of steroid 5-alpha reductase and an androgen receptor inhibits hair growth, resulting in the occurrence of hair loss (Chhipa, R R et al., Prostate, 73:1483, 2013; Azzouni, F et al, Advances in Urology, 2012:18, 2012; Winiarska, A. et al., Skin Pharmacology and Physiology, 19:311, 2006).

There are two types of steroid 5-alpha reductase: type 1 and type 2. Steroid 5-alpha reductase type 1 is mainly distributed throughout the skin, especially in the sebaceous glands, and steroid 5-alpha reductase type 2 is mainly distributed around the dermal papilla of the hair follicles and in the outer root sheath. In the early stage of drug development, hair loss therapeutic agents targeting only steroid 5-alpha reductase type 2 have mainly been developed, but therapeutic agents for inhibiting both steroid 5-alpha reductase type 1 and type 2 have recently been developed since the type 1 also has been found to affect hair growth.

Among these, finasteride may be used as a drug for inhibiting steroid 5-alpha reductase type 2. Finasteride was originally developed as a therapeutic agent for benign prostatic hypertrophy, it has been approved by the FDA and the Korean Food and Drug Administration as a male pattern hair loss therapeutic agent since finasteride was confirmed to promote hair growth in patients administered. Dutasteride is known to be a therapeutic ingredient that inhibits both steroid 5-alpha reductase type 1 and type 2. Drugs which bind to the androgen receptor and thus acts as an antagonist that hinders the binding between the androgen receptor and DHT are called anti-androgen drugs, and as these anti-androgen drugs, Cimetidine, Spironolactone, Flutamide, Cyproterone acetate, and the like are known.

However, these therapeutic ingredients have problems such as sexual dysfunction, fatigue appeal, and the like, and the use thereof is limited in women of childbearing age. These may cause fetal malformations when exposed to pregnant women. Therefore, there is a need to develop a therapeutic agent for hair loss without such side effects.

Under these technical backgrounds, the inventors of the present invention confirmed that a novel RNAi drug with minimal side effects developed using siRNA for inhibiting the expression of the 3-oxo-5-alpha-steroid 4-dehydrogenase 1 (SRD5A1) gene, the 3-oxo-5-alpha-steroid 4-dehydrogenase 2 (SRD5A2) gene, or the androgen receptor (AR) gene was able to exhibit a desired effect of preventing or treating hair loss, and thus completed the present invention.

DISCLOSURE

Technical Problem

It is an object of the present invention to provide asymmetric shorter duplex siRNA (asiRNA) specifically binding to a SRD5A1-encoding gene, a SRD5A2-encoding gene, or an AR-encoding gene.

It is another object of the present invention to provide a composition for preventing or treating hair loss which comprises the asiRNA, or a method of preventing or treating hair loss.

Technical Solution

To achieve the above object, the present invention provides siRNA specifically binding to mRNA of a 3-oxo-5-alpha-steroid 4-dehydrogenase 1 (SRD5A1)-encoding gene, mRNA of a 3-oxo-5-alpha-steroid 4-dehydrogenase 2 (SRD5A2)-encoding gene, or mRNA of an androgen receptor (AR)-encoding gene and comprising a sense strand having a length of 15-17 nt and an antisense strand complementary to the sense strand and having a length of 19 nt or more, wherein the 3'-terminus of the sense strand and the 5'-terminus of the antisense strand form a blunt end.

The present invention also provides a composition for preventing or treating hair loss which comprises the siRNA.

The present invention also provides a method of preventing or treating hair loss, comprising administering the siRNA to a subject.

The present invention also provides a use of the siRNA for preventing or treating hair loss.

The present invention also provides a use of the siRNA for preparing a drug for the prevention or treatment of hair loss.

DETAILED DESCRIPTION AND EXEMPLARY EMBODIMENTS

Figure 1A:
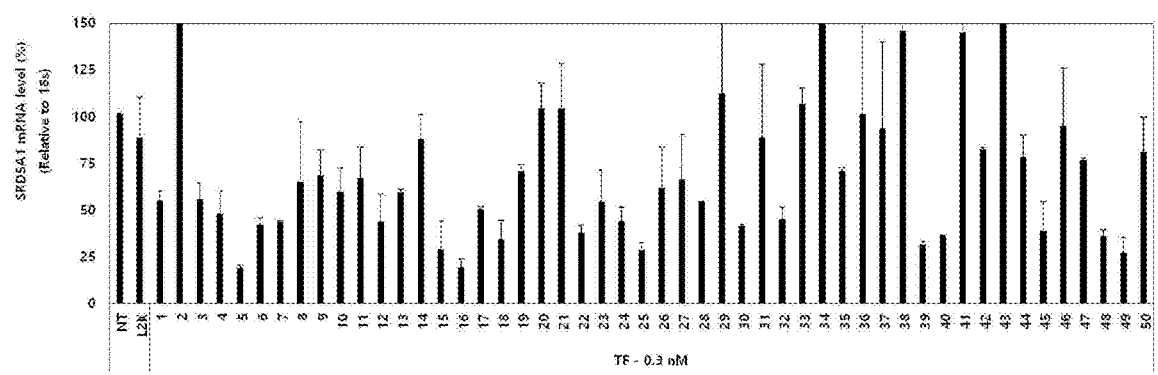
FIGS. 1A and 1B illustrate results showing the gene inhibitory efficiency of asiRNA against 100 sequences targeting SRD5A1. HuH-7 cells were transfected with 0.3 nM asiRNA targeting each nucleotide sequence, and after 24 hours, the expression level of SRD5A1 mRNA was measured using qRT-PCR, and the graphs show the mean and SD of two repeated experiments.

Unless otherwise defined, all technical and scientific terms as used herein have the same meanings as those commonly understood by one of ordinary skill in the art to which the present invention pertains. Generally, the nomenclature used herein is well known and commonly used in the art.

Accordingly, in one aspect, the present invention relates to siRNA specifically binding to mRNA of a 3-oxo-5-alpha-steroid 4-dehydrogenase 1 (SRD5A1)-encoding gene having SEQ ID NOs: 669, 670 or 671, mRNA of a 3-oxo-5-alpha-steroid 4-dehydrogenase 2 (SRD5A2)-encoding gene having SEQ ID NO: 672, or mRNA of an androgen receptor (AR)-encoding gene having SEQ ID NO: 673 and comprising a sense strand having a length of 15-17 nt and an antisense strand complementary to the sense strand and having a length of 19 nt or more, wherein the 3'-terminus of the sense strand and the 5'-terminus of the antisense strand form a blunt end.

The SRD5A1-encoding gene, which is a target gene for male pattern hair loss, for example, androgenetic alopecia, has mRNA Accession Number: NM_001047.3, NM_001324322.1, or NM_001324323.1, which respectively include sequences with SEQ ID: 669, SEQ ID NO: 670, and SEQ ID NO: 671. The SRD5A2-encoding gene has mRNA Accession Number: NM_000348.3 and includes a sequence having SEQ ID NO: 672. The AR-encoding gene has mRNA Accession Number: NM_001011645.2 and includes a sequence having SEQ ID NO: 673.

In the present invention, siRNA is a concept including all substances having a general RNA interference (RNAi) action. RNAi is an intracellular mechanism for gene regulation that was first found in *Caenorhabditis elegans* in 1998, and as for the mechanism action, it is known that the antisense strand of a double-stranded RNA introduced into a cell complementarily binds to mRNA of a target gene to thereby induce the degradation of the target gene. In this regard, small interfering RNA (siRNA) is one of the methods of inhibiting gene expression in vitro. siRNAs of 19-21 bp in length are theoretically capable of performing selective inhibition against almost all genes, and thus can be developed as therapeutic agents for various gene-related diseases such as cancer, viral infection, and the like, and is the new candidate drug development technology that has recently drawn the most attention. The first attempt to perform in vivo treatment using siRNA in mammals was in mid-2003, and since then, there have been numerous reports of in vivo treatment thanks to many attempts for application studies.

However, contrary to the possibility of in vivo treatment, side effects and disadvantages of siRNA have continually been reported. To develop an RNAi-based therapeutic agent, challenges such as: 1) the absence of an effective delivery system; 2) the off-target effect; 3) the induction of immune responses; and 4) intracellular RNAi mechanism saturation need to be overcome. Although siRNAs are an effective method of directly regulating target gene expression, it is difficult to develop a therapeutic agent using such siRNAs due to the above-described problems. With regard thereto, the applicant of the present invention has developed an asymmetric shorter duplex siRNA (asiRNA) structure-related technology (WO2009/078685). asiRNA is an asymmetric RNAi-inducing structure having a shorter double helix length than the 19+2 structure of existing siRNAs. asiRNA is a technology that has overcome known problems with the existing siRNA structure technology, such as the off-target effect, RNAi mechanism saturation, immune responses by TLR3, and the like, and accordingly is used for the development of a new RNAi drug with minimal side effects.

Based on this, the present invention provides asymmetric siRNA including a sense strand having a length of 15-17 nt and an antisense strand complementary to the sense strand and having a length of 19 nt or more, and thus the siRNA according to the present invention may stably maintain high delivery efficiency without incurring problems such as the off-target effect, RNAi mechanism saturation, immune responses by TLR3, and the like, and may inhibit the expression of a 5α-reductase type 1 target gene, a 5α-reductase type 2 target gene, and an androgen receptor target gene.

In the present invention, the term "sense strand" refers to a polynucleotide having the same nucleic acid sequence as that of the SRD5A1-, SRD5A2-, or AR-encoding gene, and has a length of 15-17 nt. In one embodiment, the sense strand may have a length of 15 nt, 16 nt, or 17 nt.

The inventors of the present application selected, as target genes, 5α-reductase type 1, 5α-reductase type 2, and an androgen receptor, which play a major role in inhibiting the synthesis of proteins required for hair follicle growth in male pattern hair loss and inducing hair loss by reducing the dermal papilla. As a result of screening 100 or more siRNAs targeting each target gene and selecting siRNAs with excellent inhibitory efficiency from among the same, it was confirmed that siRNA comprising a sense strand having one selected from SEQ ID NOS: 5, 6, 15, 18, 40, 48, 49, 59, 62, 69, 77, 86, 205, 208, 228, 231, 232, 233, 237, 238, 239, 240, 242, 248, 249, 259, 260, 262, 265, 283, 284, 285, 291, 292, 300, 471, 477, 498, 500, 502, 503, 505, 506, 507, 509, 510, 515, 517, 518, 521, 524, 534, 538, 539, and 546 and an antisense strand complementary to the sense strand, effectively reduced the expression of mRNA of the SRD5A1-, SRD5A2-, or AR-encoding gene.

Specifically, siRNA comprising a sense strand having SEQ ID NO: 5, 6, 15, 18, 40, 48, 49, 59, 62, 69, 77, or 86 and an antisense strand complementary to the sense strand, may reduce the expression of mRNA of the SRD5A1-encoding gene, siRNA comprising a sense strand having SEQ ID NO: 205, 208, 228, 231, 232, 233, 237, 238, 239, 240, 242, 248, 249, 259, 260, 262, 265, 283, 284, 285, 291, 292, or 300 and an antisense strand complementary to the sense strand, may reduce the expression of mRNA of the SRD5A2-encoding gene, and siRNA comprising a sense strand having SEQ ID NO: 471, 477, 498, 500, 502, 503, 505, 506, 507, 509, 510, 515, 517, 518, 521, 524, 534, 538, 539, or 546 and an antisense strand complementary to the sense strand, may reduce the expression of mRNA of the AR-encoding gene.

Specifically, it was confirmed that siRNA comprising a sense strand having one selected from the group consisting of SEQ ID NOS: 48, 49, 69, 86, 231, 259, 260, 262, 498, 500, 506, 509, 510, 518, 538, 539, and 546 and an antisense strand complementary to the sense strand also effectively inhibited the expression of the SRD5A1 protein, the SRD5A2 protein, or the AR protein.

The 3'-terminus of the sense strand and the 5'-terminus of the antisense strand form a blunt end. For example, the 5'-terminus of the antisense strand may include, for example, an overhang of 1 nt, 2 nt, 3 nt, 4 nt, 5 nt, 6 nt, 7 nt, or 8 nt.

In the present invention, the antisense strand is a polynucleotide complementary to the target gene and has a length of 19 nt or more, for example, 20 nt or more, 21 nt or more, 22 nt or more, 23 nt or more, 24 nt or more, 25 nt or more, 26 nt or more, 27 nt or more, 29 nt or more, 30 nt or more, or 31 nt or more. In one embodiment, the antisense strand may have a length between 19 nt and 24 nt, for example, 19 nt, 20 nt, 21 nt, 22 nt, 23 nt, or 24 nt. The antisense strand may have a sequence partially complementary to the sense strand in consideration of the asymmetric structure.

The antisense strand may, for example, be selected from the group consisting of SEQ ID NOS: 105, 106, 115, 118, 140, 148, 149, 159, 162, 169, 177, 186, 317, 320, 340, 343, 344, 345, 349, 350, 351, 352, 354, 360, 361, 371, 372, 374, 377, 395, 396, 397, 403, 404, 412, 589, 595, 616, 618, 620, 621, 623, 624, 625, 627, 628, 633, 635, 636, 639, 642, 652, 656, 657, and 664.

Specifically, it was confirmed that siRNA comprising an antisense strand selected from the group consisting of SEQ ID NOS: 148, 149, 169, 186, 343, 371, 372, 374, 616, 618, 624, 627, 628, 636, 656, 657, and 664 also effectively inhibited the expression of the SRD5A1 protein, the SRD5A2 protein, or the AR protein.

In some embodiments, the sense strand or antisense strand of the siRNA may include one or more chemical modifications.

General siRNAs are unable to penetrate through the cell membrane due to reasons such as high negative charge, high molecular weight, and the like, and are rapidly degraded and eliminated in the blood, making it difficult to deliver an amount sufficient for RNAi induction to an actual target site. Currently, in the case of in vitro delivery, numerous high-efficiency delivery methods using cationic lipids and cationic polymers have been developed, but in vivo delivery of siRNA as efficient as in vitro delivery thereof is difficult, and siRNA delivery efficiency is reduced by interactions between various proteins present in the living body.

Therefore, the inventors of the present application developed cell penetrating asiRNA (cp-asiRNA) having self-transfer ability that enables effective intracellular delivery without a separate delivery vehicle by introducing a chemical modification into an asymmetric siRNA structure.

The chemical modification in the sense strand or the antisense strand may comprise, for example, at least one selected from the group consisting of:

a modification in which an —OH group at the 2' carbon position of a sugar structure in a nucleotide is substituted with —CH$_3$ (methyl), —OCH$_3$ (methoxy), —NH$_2$, —F (fluorine), —O-2-methoxyethyl-O-propyl, —O-2-methylthioethyl, —O-3-aminopropyl, or —O-3-dimethylaminopropyl;

a modification in which oxygen in a sugar structure in a nucleotide is substituted with sulfur;

a modification of a nucleotide bond to a phosphorothioate, boranophosphate or methyl phosphonate;

a modification to peptide nucleic acid (PNA), locked nucleic acid (LNA), or unlocked nucleic acid (UNA); and cholesterol or cell-penetrating peptide binding.

In one embodiment, the chemical modification in the sense or antisense strand may be substitution of an —OH group at the 2' carbon position of a sugar structure in a nucleotide with —CH$_3$ (methyl), modification of a nucleotide bond into phosphorothioate, or cholesterol binding. This may enhance the in vivo stability of siRNA.

When the —OH group at the 2' carbon position of a sugar structure is substituted with —CH$_3$ (methyl) or when the nucleotide bond is modified into a phosphorothioate, resistance to nucleases may be increased, and binding to the cell membrane via cholesterol binding may facilitate the intracellular delivery of siRNA.

In particular, the chemical modification may include at least one modification selected from the group consisting of: a modification in which an —OH group at the 2' carbon position of a sugar structure in the 5'- or 3'-terminus nucleotide of the sense strand is substituted with —CH$_3$ (methyl); a modification in which an —OH group at the 2' carbon position of a sugar structure in two or more nucleotides of the sense strand or the antisense strand is substituted with —CH$_3$ (methyl); a modification of 25% or more of nucleotides bonds in the sense or antisense strand to phosphorothioate; and cholesterol binding at the 3'-terminus of the sense strand.

With regard to the modification in which an —OH group at the 2' carbon position of a sugar structure in a nucleotide is substituted with —CH$_3$ (methyl), the —OH group at the 2' carbon position of the sugar structure in a nucleotide positioned at the 5'-terminus of the sense strand may be substituted with —CH$_3$ (methyl). In addition, a 2'-O-methylated nucleoside, in which an —OH group at the 2' carbon position of a sugar structure is substituted with —CH$_3$ (methyl), may be continuously or discontinuously included in a 5'-terminus to 3'-terminus direction of the sense strand. 2'-O-methylated nucleosides and unmodified nucleosides may be alternately included in the sense strand. 2, 3, 4, 5, 6, 7, or 8 consecutive 2'-O-methylated nucleosides and unmodified nucleosides may be alternately included in the sense strand. For example, two or more, three or more, four or more, five or more, six or more, seven or more, eight or more, 2 to 8, or 8 2'-O-methylated nucleosides may be present in the sense strand.

2'-O-methylated nucleosides may be continuously or discontinuously included in a 5'-terminus to 3'-terminus of the antisense strand. 2'-O-methylated nucleosides and unmodified nucleotides may be alternately included in the antisense strand. 2, 3, 4, 5, 6, 7, or 8 consecutive 2'-O-methylated nucleosides and unmodified nucleosides may be alternately included in the antisense strand. For example, two or more, three or more, four or more, five or more, six or more, seven or more, eight or more, or 2-7 2'-O-methylated nucleosides may be present in the antisense strand.

With regard to the modification of a nucleotide bond to a phosphorothioate, at least 25%, 30%, 35%, 40%, 45%, 50%, 55%, 60%, 65%, 70%, 75%, 80%, 85%, 90%, or 95% of bonds between ribonucleotides in the sense strand may be modified into phosphorothioate. In some embodiments, all (100%) of the bonds between ribonucleotides in the sense strand may be modified into phosphorothioate.

At least 25%, 30%, 35%, 40%, 45%, 50%, 55%, 60%, 65%, 70%, 75%, 80%, 85%, 90%, or 95% of the bonds between ribonucleotides in the antisense strand may be modified into phosphorothioate. In some embodiments, a total (100%) of the bonds between ribonucleotides in the antisense strand may be modified into phosphorothioate.

In another aspect, the present invention relates to a composition for the prevention or treatment of hair loss, which comprises the siRNA.

The term "treatment" as used herein means reducing the symptoms of hair loss or the severity of hair loss in a subject to which the composition is administered or preventing the same from being aggravated, and in some cases may include the progression of hair growth. The term "prevention" as used herein means preventing or delaying the initiation of hair loss, or reducing the possibility of developing hair loss.

The composition may further be prepared including one or more pharmaceutically acceptable carriers, in addition to the siRNA as an active ingredient. The pharmaceutically acceptable carrier has to be compatible with the active ingredient of the present invention, and may be one selected from physiological saline, sterile water, Ringer's solution, buffered saline, dextrose solution, maltodextrin solution, glycerol, ethanol, and a mixture of two or more of these components. If necessary, the composition may include other general additives such as an antioxidant, a buffer, a bacteriostatic agent, and the like. In addition, the composition may be formulated into an injectable preparation such as an aqueous solution, a suspension, an emulsion, or the like by further adding a diluent, a dispersing agent, a surfactant, a binder, and a lubricant. In particular, the composition may be formulated into a lyophilized preparation. The lyophilized preparation may be formulated using a method commonly used in the art to which the present invention pertains, and a stabilizer for lyophilization may also be added.

An administration method of the composition may be determined by one of ordinary skill in the art on the basis of general symptoms of patients and the severity of diseases. In addition, the composition may be formulated into various forms such as powders, tablets, capsules, liquids, injections, ointments, syrups, and the like, and may also be provided in a unit dosage or multiple dosage container, for example, sealed ampoules and vials, and the like.

The composition may be administered orally or parenterally. The administration route of the composition according to the present invention may be, but is not limited to, for example, oral administration, intravenous administration, intramuscular administration, intraarterial administration, intramedullary administration, intradural administration, intracardiac administration, transdermal administration, subcutaneous administration, intraperitoneal administration, intestinal administration, sublingual administration, or topical administration. The dosage of the composition according to the present invention varies depending on the body weight, age, gender, and health condition of a patient, diet, administration time, administration method, excretion rate, severity of disease, or the like, and may be easily determined by those of ordinary skill in the art. In addition, for clinical administration, the composition of the present invention may be formulated into a suitable form using known techniques.

In another aspect of the present invention, there is provided a method of preventing or treating hair loss, comprising administering the siRNA to a subject.

In another aspect, the present invention relates to a use of the siRNA for preventing or treating hair loss.

In another aspect, the present invention relates to a use of the siRNA for preparing a drug for the prevention or treatment of hair loss.

Configurations included in the prevention or treatment method according to the present invention are the same as those included in the aforementioned embodiments, and thus the foregoing description may be equally applied to the prevention or treatment method.

Hereinafter, the present invention will be described in further detail with reference to the following examples. It will be obvious to those of ordinary skill in the art that these examples are provided for illustrative purposes only and are not intended to limit the scope of the present invention.

[Example 1] Screening for 100 Kinds of RNAi-Inducing Double-Stranded Nucleic Acid Molecules Targeting SRD5A1

To obtain high-efficiency RNAi-inducing double-stranded nucleic acid molecules targeting SRD5A1, the target sequence of the SRD5A1 gene was selected and then asiRNA was designed. The asiRNA structure is different from that of generally known siRNAs, and thus when the nucleotide sequences of asiRNA are designed using a general siRNA design program, it may be somewhat difficult to design an optimized asiRNA. Therefore, asiRNA was constructed by the following method. An NCBI db search was used to obtain information on the SRD5A1 gene (mRNA Accession Number: NM_001047.3, NM_001324322.1, NM_001324323.1), which is the target gene pertaining to male pattern hair loss (androgenetic hair loss). For subsequent animal experiments, nucleotide sequences were secured in consideration of the nucleotide sequence homology with mice, and then 100 kinds of asiRNA were designed according to a design method such as the exclusion of sequences having a GC content of 30-62% and 4 or more G or C consecutive bases, and then synthesized by OliX Inc. (Korea). The synthesized sense and antisense strand RNA oligonucleotides were annealed at 95° C. for 2 minutes through incubation at 37° C. for 1 hour, and the asiRNA annealed by 10% polyacrylamide gel electrophoresis (PAGE) was confirmed using a UV transilluminator.

TABLE 1

100 Kinds of asiRNA nucleotide sequences targeting 3-oxo-5-alpha-steroid 4-dehydrogenase 1

| No. | Name | S | AS |
|---|---|---|---|
| 1 | asiSRD5A1 1 | GCAGAUACUUGAGCCA (SEQ ID NO: 1) | UGGCUCAAGUAUCUG CUUUGC (SEQ ID NO: 101) |
| 2 | asiSRD5A1 2 | AAGCAGAUACUUGAGC (SEQ ID NO: 2) | GCUCAAGUAUCUGCU UUGCAA (SEQ ID NO: 102) |
| 3 | asiSRD5A1 3 | CAAAGCAGAUACUUGA (SEQ ID NO: 3) | UCAAGUAUCUGCUUU GCAAAU (SEQ ID NO: 103) |
| 4 | asiSRD5A1 4 | UGCAAAGCAGAUACUU (SEQ ID NO: 4) | AAGUAUCUGCUUUGC AAAUAG (SEQ ID NO: 104) |
| 5 | asiSRD5A1 5 | GUGCAGUGUAUGCUGA (SEQ ID NO: 5) | UCAGCAUACACUGCA CAAUGG (SEQ ID NO: 105) |
| 6 | asiSRD5A1 6 | UUGUGCAGUGUAUGCU (SEQ ID NO: 6) | AGCAUACACUGCACA AUGGCU (SEQ ID NO: 106) |
| 7 | asiSRD5A1 7 | CAUUGUGCAGUGUAUG (SEQ ID NO: 7) | CAUACACUGCACAAU GGCUCA (SEQ ID NO: 107) |
| 8 | asiSRD5A1 8 | UUUUGGCUUGUGGUUA (SEQ ID NO: 8) | UAACCACAAGCCAAA ACCUAU (SEQ ID NO: 108) |
| 9 | asiSRD5A1 9 | CGGGCAUGUUGAUAAA (SEQ ID NO: 9) | UUUAUCAACAUGCCC GUUAAC (SEQ ID NO: 109) |
| 10 | asiSRD5A1 10 | AUAUCCUAAGGAAUCU (SEQ ID NO: 10) | AGAUUCCUUAGGAUA UGAUCU (SEQ ID NO: 110) |
| 11 | asiSRD5A1 11 | AUCUCAGAAAACCAGG (SEQ ID NO: 11) | CCUGGUUUUCUGAGA UUCCUU (SEQ ID NO: 111) |
| 12 | asiSRD5A1 12 | GAAUCUCAGAAAACCA (SEQ ID NO: 12) | UGGUUUUCUGAGAUU CCUUAG (SEQ ID NO: 112) |
| 13 | asiSRD5A1 13 | AGGAAUCUCAGAAAAC (SEQ ID NO: 13) | GUUUUCUGAGAUUCC UUAGGA (SEQ ID NO: 113) |
| 14 | asiSRD5A1 14 | CUGGAUACAAAAUACC (SEQ ID NO: 14) | GGUAUUUUGUAUCCA GUAUCU (SEQ ID NO: 114) |
| 15 | asiSRD5A1 15 | UACUGGAUACAAAAUA (SEQ ID NO: 15) | UAUUUUGUAUCCAGU AUCUCC (SEQ ID NO: 115) |
| 16 | asiSRD5A1 16 | GAUACUGGAUACAAAA (SEQ ID NO: 16) | UUUUGUAUCCAGUAU CUCCUG (SEQ ID NO: 116) |
| 17 | asiSRD5A1 17 | GAGAUACUGGAUACAA (SEQ ID NO: 17) | UUGUAUCCAGUAUCU CCUGGU (SEQ ID NO: 117) |
| 18 | asiSRD5A1 18 | AGGAGAUACUGGAUAC (SEQ ID NO: 18) | GUAUCCAGUAUCUCC UGGUUU (SEQ ID NO: 118) |

TABLE 1-continued

100 Kinds of asiRNA nucleotide sequences targeting 3-oxo-5-alpha-steroid 4-dehydrogenase 1

| No. | Name | Sequence (5'-3') S | Sequence (5'-3') AS |
|---|---|---|---|
| 19 | asiSRD5A1 19 | CCAGGAGAUACUGGAU (SEQ ID NO: 19) | AUCCAGUAUCUCCUGGUUUUC (SEQ ID NO: 119) |
| 20 | asiSRD5A1 20 | AAUACCAAGGGGAGGC (SEQ ID NO: 20) | GCCUCCCCUUGGUAUUUUGUA (SEQ ID NO: 120) |
| 21 | asiSRD5A1 21 | AAAAUACCAAGGGGAG (SEQ ID NO: 21) | CUCCCCUUGGUAUUUUGUAUC (SEQ ID NO: 121) |
| 22 | asiSRD5A1 22 | GAGGCUUAUUUGAAUA (SEQ ID NO: 22) | UAUUCAAAUAAGCCUCCCCUU (SEQ ID NO: 122) |
| 23 | asiSRD5A1 23 | CAGCCAACUAUUUUGG (SEQ ID NO: 23) | CCAAAAUAGUUGGCUGCAGUU (SEQ ID NO: 123) |
| 24 | asiSRD5A1 24 | UGCAGCCAACUAUUUU (SEQ ID NO: 24) | AAAAUAGUUGGCUGCAGUUAC (SEQ ID NO: 124) |
| 25 | asiSRD5A1 25 | ACUGCAGCCAACUAUU (SEQ ID NO: 25) | AAUAGUUGGCUGCAGUUACGU (SEQ ID NO: 125) |
| 26 | asiSRD5A1 26 | UAACUGCAGCCAACUA (SEQ ID NO: 26) | UAGUUGGCUGCAGUUACGUAU (SEQ ID NO: 126) |
| 27 | asiSRD5A1 27 | CGUAACUGCAGCCAAC (SEQ ID NO: 27) | GUUGGCUGCAGUUACGUAUUC (SEQ ID NO: 127) |
| 28 | asiSRD5A1 28 | AUGGAGUGGUGUGGCU (SEQ ID NO: 28) | AGCCACACCACUCCAUGAUUU (SEQ ID NO: 128) |
| 29 | asiSRD5A1 29 | UCAUGGAGUGGUGUGG (SEQ ID NO: 29) | CCACACCACUCCAUGAUUUCU (SEQ ID NO: 129) |
| 30 | asiSRD5A1 30 | AAUCAUGGAGUGGUGU (SEQ ID NO: 30) | ACACCACUCCAUGAUUUCUCC (SEQ ID NO: 130) |
| 31 | asiSRD5A1 31 | GAAAUCAUGGAGUGGU (SEQ ID NO: 31) | ACCACUCCAUGAUUUCUCCAA (SEQ ID NO: 131) |
| 32 | asiSRD5A1 32 | GAGAAAUCAUGGAGUG (SEQ ID NO: 32) | CACUCCAUGAUUUCUCCAAAA (SEQ ID NO: 132) |
| 33 | asiSRD5A1 33 | CCCUGGCCAGCUGGUC (SEQ ID NO: 33) | GACCAGCUGGCCAGGGCAUAG (SEQ ID NO: 133) |
| 34 | asiSRD5A1 34 | UAUGCCCUGGCCAGCU (SEQ ID NO: 34) | AGCUGGCCAGGGCAUAGCCAC (SEQ ID NO: 134) |
| 35 | asiSRD5A1 35 | GCUAUGCCCUGGCCAG (SEQ ID NO: 35) | CUGGCCAGGGCAUAGCCACAC (SEQ ID NO: 135) |
| 36 | asiSRD5A1 36 | UCAUGAGUGGUACCUC (SEQ ID NO: 36) | GAGGUACCACUCAUGAUGCUC (SEQ ID NO: 136) |
| 37 | asiSRD5A1 37 | CAUCAUGAGUGGUACC (SEQ ID NO: 37) | GGUACCACUCAUGAUGCUCUU (SEQ ID NO: 137) |
| 38 | asiSRD5A1 38 | UCCGGAAAUUUGAAGA (SEQ ID NO: 38) | UCUUCAAAUUUCCGGAGGUAC (SEQ ID NO: 138) |
| 39 | asiSRD5A1 39 | CAGUGUAUGCUGAUGA (SEQ ID NO: 39) | UCAUCAGCAUACACUGCACAA (SEQ ID NO: 139) |
| 40 | asiSRD5A1 40 | GCAUGUUGAUAAACAU (SEQ ID NO: 40) | AUGUUUAUCAACAUGCCCGUU (SEQ ID NO: 140) |
| 41 | asiSRD5A1 41 | GUGGCUAUGCCCUGGC (SEQ ID NO: 41) | GCCAGGGCAUAGCCACACCAC (SEQ ID NO: 141) |
| 42 | asiSRD5A1 42 | GUGUGGCUAUGCCCUG (SEQ ID NO: 42) | CAGGGCAUAGCCACACCACUC (SEQ ID NO: 142) |
| 43 | asiSRD5A1 43 | UGGUGUGGCUAUGCCC (SEQ ID NO: 43) | GGGCAUAGCCACACCACUCCA (SEQ ID NO: 143) |
| 44 | asiSRD5A1 44 | AGUGGUGUGGCUAUGC (SEQ ID NO: 44) | GCAUAGCCACACCACUCCAUG (SEQ ID NO: 144) |
| 45 | asiSRD5A1 45 | UCUUCACGUUUUGUUU (SEQ ID NO: 45) | AAACAAAACGUGAAGAAAGCA (SEQ ID NO: 145) |
| 46 | asiSRD5A1 46 | GACUUGAGAACCCUUU (SEQ ID NO: 46) | AAAGGGUUCUCAAGUCAGGCU (SEQ ID NO: 146) |
| 47 | asiSRD5A1 47 | CUGUUGGCGUGUACAA (SEQ ID NO: 47) | UUGUACACGCCAACAGUGGCA (SEQ ID NO: 147) |
| 48 | asiSRD5A1 48 | UUAUUUGAAUACGUAA (SEQ ID NO: 48) | UUACGUAUUCAAAUAAGCCUC (SEQ ID NO: 148) |
| 49 | asiSRD5A1 49 | UUCCAAUGGCGCUUCU (SEQ ID NO: 49) | AGAAGCGCCAUUGGAAAGCUU (SEQ ID NO: 149) |
| 50 | asiSRD5A1 50 | AAAGGCAUCUGGACUU (SEQ ID NO: 50) | AAGUCCAGAUGCCUUUGCCUC (SEQ ID NO: 150) |
| 51 | asiSRD5A1 51 | AUCAAUGUGCUCUGGU (SEQ ID NO: 51) | ACCAGAGCACAUUGAUGGCUC (SEQ ID NO: 151) |
| 52 | asiSRD5A1 52 | GAUCACUUUCUGUAAC (SEQ ID NO: 52) | GUUACAGAAAGUGAUCAUUCU (SEQ ID NO: 152) |
| 53 | asiSRD5A1 53 | AUCUUCCUUCUAAUAG (SEQ ID NO: 53) | CUAUUAGAAGGAAGAUUAGCU (SEQ ID NO: 153) |
| 54 | asiSRD5A1 54 | GGCAUUGCUUUGCCUU (SEQ ID NO: 54) | AAGGCAAAGCAAUGCCAGAUG (SEQ ID NO: 154) |

TABLE 1-continued

100 Kinds of asiRNA nucleotide sequences targeting 3-oxo-5-alpha-steroid 4-dehydrogenase 1

| No. | Name | Sequence (5'-3') S | AS |
|---|---|---|---|
| 55 | asiSRD5A1 55 | UGUACAAUGGCGAUUA (SEQ ID NO: 55) | UAAUCGCCAUUGUACACGCCA (SEQ ID NO: 155) |
| 56 | asiSRD5A1 56 | CUUCUCUAUGGACUUU (SEQ ID NO: 56) | AAAGUCCAUAGAGAAGCGCCA (SEQ ID NO: 156) |
| 57 | asiSRD5A1 57 | UUCCAAGGUGAGGCAA (SEQ ID NO: 57) | UUGCCUCACCUUGGAAGGGCC (SEQ ID NO: 157) |
| 58 | asiSRD5A1 58 | UCCAAGGUGAGGCAAA (SEQ ID NO: 58) | UUUGCCUCACCUUGGAAGGGC (SEQ ID NO: 158) |
| 59 | asiSRD5A1 59 | GGUUCAUACGGAGUAA (SEQ ID NO: 59) | UUACUCCGUAUGAACCACCAC (SEQ ID NO: 159) |
| 60 | asiSRD5A1 60 | AUAGUAGAGAUUGUUG (SEQ ID NO: 60) | CAACAAUCUCUACUAUAUCCA (SEQ ID NO: 160) |
| 61 | asiSRD5A1 61 | UGUUGUCUGUGAAAUU (SEQ ID NO: 61) | AAUUUCACAGACAACAAUCUC (SEQ ID NO: 161) |
| 62 | asiSRD5A1 62 | UUCAAGCUCUGGGUAA (SEQ ID NO: 62) | UUACCCAGAGCUUGAAAUUCU (SEQ ID NO: 162) |
| 63 | asiSRD5A1 63 | UACCUAAUAAGUACCU (SEQ ID NO: 63) | AGGUACUUAUUAGGUAGAUUG (SEQ ID NO: 163) |
| 64 | asiSRD5A1 64 | AUUGUUGUCUGUGAAA (SEQ ID NO: 64) | UUUCACAGACAACAAUCUCUA (SEQ ID NO: 164) |
| 65 | asiSRD5A1 65 | CAAAAGAGCAUCAUGA (SEQ ID NO: 65) | UCAUGAUGCUCUUUUGCUCUA (SEQ ID NO: 165) |
| 66 | asiSRD5A1 66 | CUAUGGACUUUGUAAA (SEQ ID NO: 66) | UUUACAAAGUCCAUAGAGAAG (SEQ ID NO: 166) |
| 67 | asiSRD5A1 67 | CUGUCUUUGAUGGCAU (SEQ ID NO: 67) | AUGCCAUCAAAGACAGUUGUA (SEQ ID NO: 167) |
| 68 | asiSRD5A1 68 | UCUACCUAAUAAGUAC (SEQ ID NO: 68) | GUACUUAUUAGGUAGAUUGCA (SEQ ID NO: 168) |
| 69 | asiSRD5A1 69 | CUAAUCUUCCUUCUAA (SEQ ID NO: 69) | UUAGAAGGAAGAUUAGCUAUG (SEQ ID NO: 169) |
| 70 | asiSRD5A1 70 | CAUUUUCAGAACAAUA (SEQ ID NO: 70) | UAUUGUUCUGAAAAUGCCAUC (SEQ ID NO: 170) |
| 71 | asiSRD5A1 71 | GAUCUCUUCAAGGUCA (SEQ ID NO: 71) | UGACCUUGAAGAGAUCACUGU (SEQ ID NO: 171) |
| 72 | asiSRD5A1 72 | AGAUUGUUGUCUGUGA (SEQ ID NO: 72) | UCACAGACAACAAUCUCUACU (SEQ ID NO: 172) |
| 73 | asiSRD5A1 73 | AGAGAUUGUUGUCUGU (SEQ ID NO: 73) | ACAGACAACAAUCUCUACUAU (SEQ ID NO: 173) |
| 74 | asiSRD5A1 74 | AGACGAACUCAGUGUA (SEQ ID NO: 74) | UACACUGAGUUCGUCUGACGA (SEQ ID NO: 174) |
| 75 | asiSRD5A1 75 | UCCUCCUGGCCAUGUU (SEQ ID NO: 75) | AACAUGGCCAGGAGGAUGCAG (SEQ ID NO: 175) |
| 76 | asiSRD5A1 76 | CUUAAUUUACCCAUUU (SEQ ID NO: 76) | AAAUGGGUAAAUUAAGCACCG (SEQ ID NO: 176) |
| 77 | asiSRD5A1 77 | UGAUGCGAGGAGGAAA (SEQ ID NO: 77) | UUUCCUCCUCGCAUCAGAAAU (SEQ ID NO: 177) |
| 78 | asiSRD5A1 78 | UGUUCUGUACCUGUAA (SEQ ID NO: 78) | UUACAGGUACAGAACAUAAUC (SEQ ID NO: 178) |
| 79 | asiSRD5A1 79 | CCUGUAACGGCUAUUU (SEQ ID NO: 79) | AAAUAGCCGUUACAGGUACAG (SEQ ID NO: 179) |
| 80 | asiSRD5A1 80 | CCAUUGUGCAGUGUAU (SEQ ID NO: 80) | AUACACUGCACAAUGGCUCAA (SEQ ID NO: 180) |
| 81 | asiSRD5A1 81 | AACAUCCAUUCAGAUC (SEQ ID NO: 81) | GAUCUGAAUGGAUGUUUAUCA (SEQ ID NO: 181) |
| 82 | asiSRD5A1 82 | UAUCCAAAGUUCAGAA (SEQ ID NO: 82) | UUCUGAACUUUGGAUACUCUU (SEQ ID NO: 182) |
| 83 | asiSRD5A1 83 | ACCUAAAUACGCUGAA (SEQ ID NO: 83) | UUCAGCGUAUUUAGGUACUUA (SEQ ID NO: 183) |
| 84 | asiSRD5A1 84 | CGCUGAAAUGGAGGUU (SEQ ID NO: 84) | AACCUCCAUUUCAGCGUAUUU (SEQ ID NO: 184) |
| 85 | asiSRD5A1 85 | AAUGGAGGUUGAAUAU (SEQ ID NO: 85) | AUAUUCAACCUCCAUUUCAGC (SEQ ID NO: 185) |
| 86 | asiSRD5A1 86 | AUAUCCUACUGUGUAA (SEQ ID NO: 86) | UUACACAGUAGGAUAUUCAAC (SEQ ID NO: 186) |
| 87 | asiSRD5A1 87 | UAUGAGACUAGACUUU (SEQ ID NO: 87) | AAAGUCUAGUCUCAUACACAC (SEQ ID NO: 187) |
| 88 | asiSRD5A1 88 | AAUGUCACAAUCCCUU (SEQ ID NO: 88) | AAGGGAUUGUGACAUUUAUUG (SEQ ID NO: 188) |
| 89 | asiSRD5A1 89 | GGUCAACUGCAGUGUU (SEQ ID NO: 89) | AACACUGCAGUUGACCUUGAA (SEQ ID NO: 189) |
| 90 | asiSRD5A1 90 | GCCAUUGUGCAGUCAU (SEQ ID NO: 90) | AUGACUGCACAAUGGCUACCC (SEQ ID NO: 190) |

TABLE 1-continued

100 Kinds of asiRNA nucleotide sequences targeting 3-oxo-5-alpha-steroid 4-dehydrogenase 1

| 100 kinds | | Sequence (5'-3') | |
|---|---|---|---|
| No. | Name | S | AS |
| 91 | asiSRD5A1 91 | UGUAAGUGGAGAACUU (SEQ ID NO: 91) | AAGUUCUCCACUUAC ACACAG (SEQ ID NO: 191) |
| 92 | asiSRD5A1 92 | CUCUGCCUGUGUGAGU (SEQ ID NO: 92) | ACUCACACAGGCAGA GCAGCU (SEQ ID NO: 192) |
| 93 | asiSRD5A1 93 | ACCGUGAGCCAUCAAU (SEQ ID NO: 93) | AUUGAUGGCUCACGG UGAGUG (SEQ ID NO: 193) |
| 94 | asiSRD5A1 94 | GGUUUCUCUCUGUCUU (SEQ ID NO: 94) | AAGACAGAGAGAAAC CAUGUC (SEQ ID NO: 194) |
| 95 | asiSRD5A1 95 | UAGUCUAGACCUAGUU (SEQ ID NO: 95) | AACUAGGUCUAGACU AGAAGA (SEQ ID NO: 195) |
| 96 | asiSRD5A1 96 | UAGUGUAAAGAAUGAU (SEQ ID NO: 96) | AUCAUUCUUUACACU ACAAGG (SEQ ID NO: 196) |
| 97 | asiSRD5A1 97 | CUGUACCUGUUAUCAA (SEQ ID NO: 97) | UUGAUAACAGGUACA GGCUAU (SEQ ID NO: 197) |
| 98 | asiSRD5A1 98 | GAAUGCUUCAUGACUU (SEQ ID NO: 98) | AAGUCAUGAAGCAUU CAACAG (SEQ ID NO: 198) |
| 99 | asiSRD5A1 99 | UGCCUUAUCAUCUCAU (SEQ ID NO: 99) | AUGAGAUGAUAAGGC AAAGCA (SEQ ID NO: 199) |
| 100 | asiSRD5A1 100 | CAUCUCAUCUGGAGUU (SEQ ID NO: 100) | AACUCCAGAUGA GAUGAUAAG (SEQ ID NO: 200) |

[Example 2] Screening for RNAi-Inducing Double-Stranded Nucleic Acid Molecules Targeting SRD5A1

To confirm gene inhibitory efficiency at the mRNA level, 100 selected kinds of asiRNA were transfected into a HuH-7 cell line at a concentration of 0.3 nM, and qRT-PCR was performed to measure the expression level of SRD5A1 mRNA.

Figure 1B:
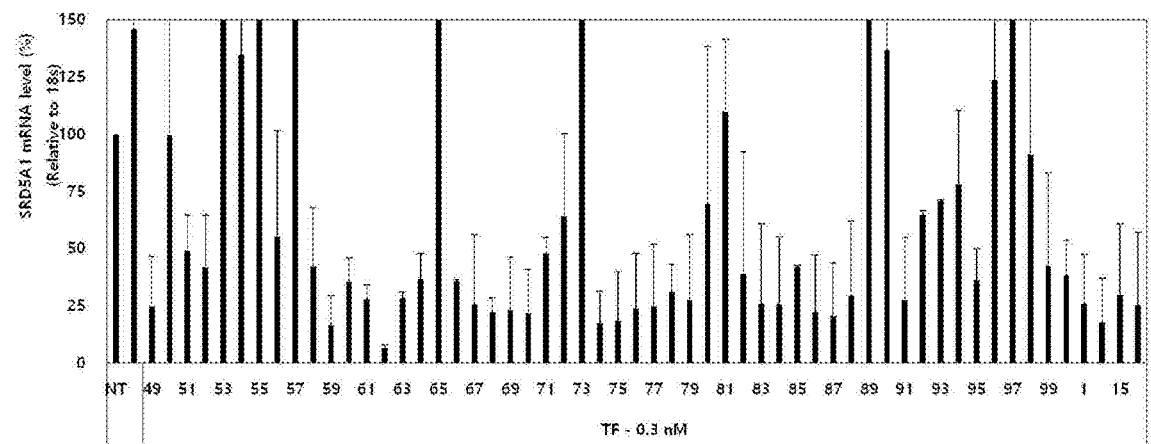

The HuH-7 cell line was cultured in Dulbecco's Modified Eagle's Medium (DMEM, Gibco) containing 10% fetal bovine serum (FBS, Gibco) and 100 units/ml of penicillin 100 μg/ml of streptomycin. HuH-7 cells were seeded in a 96-well plate at a density of 5×10$^3$ cells/well, and a reverse transfection experiment was conducted using asiRNA (0.3 nM, OliX Inc.) and Lipofectamine 2000 (1 μl/ml, Invitrogen Inc.) in Opti-MEM (a total volume of 100 μl) in accordance with Invitrogen's protocol. After 24 hours, RNA purification and cDNA synthesis were performed in accordance with a basic protocol provided by TOYOBO SuperPrep, the expression level of the SRD5A1 gene was examined with a SRD5A1 TaqMan probe (Hs00602694_mH) using a Bio-Rad CFX-4000 machine, and the results are illustrated in FIGS. 1A and 1B.

Figure 2:
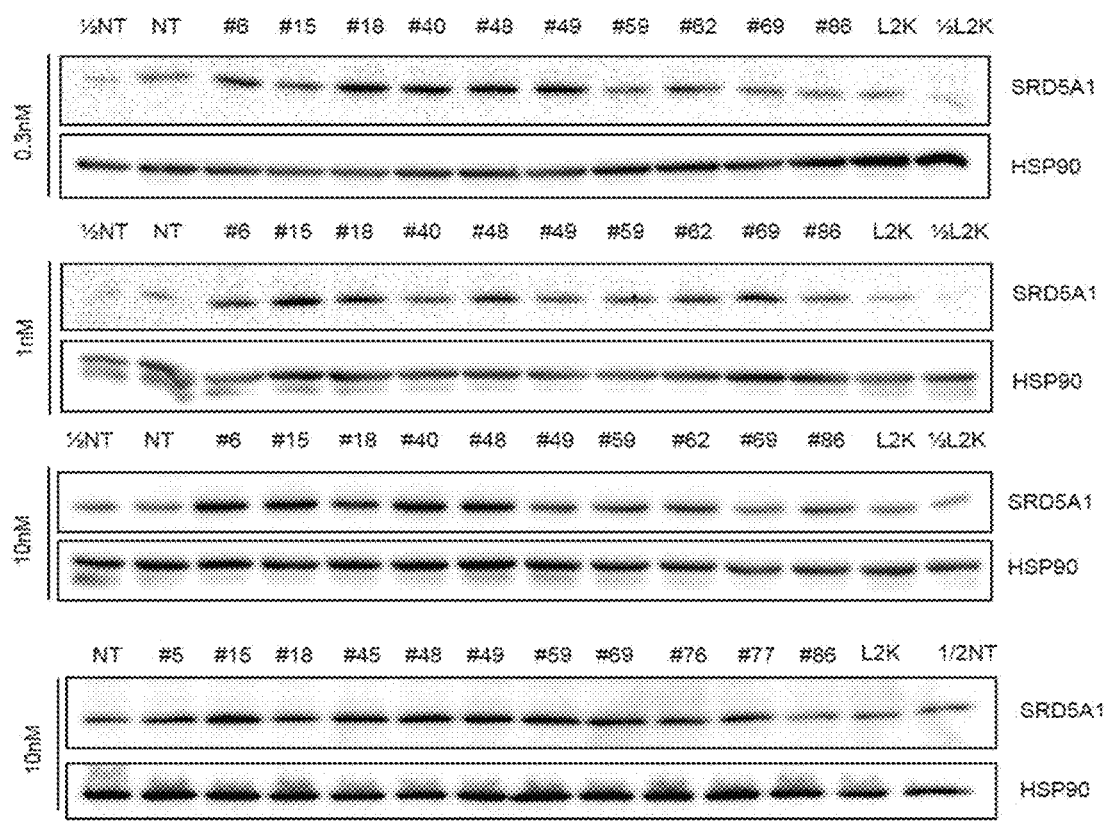
FIG. 2 illustrates results showing the gene inhibitory efficiency of asiRNA against 12 sequences targeting SRD5A1. HuH-7 cells were transfected with 0.3 nM, 1 nM, or 10 nM asiRNA targeting each nucleotide sequence, and after 48 hours, the expression level of the SRD5A1 protein was measured by western blotting.

From the results of screening the 100 kinds of asiRNA, the 12 top-ranked asiRNAs (in Table 1, No. 5, 6, 15, 18, 40, 48, 49, 59, 62, 77, and 86) were selected, followed by treatment with 0.3 nM, 1 nM, 3 nM, or 10 nM of asiRNA and western blotting to analyze the protein expression inhibitory effects thereof. HuH-7 cells were seeded in a 6-well plate at a density of 2.5×10$^3$ cells/well, and then a reverse transfection experiment was conducted using asiRNA and Lipofectamine 2000 (1 μl/ml, Invitrogen Inc.) in Opti-MEM (a total volume of 2 ml) in accordance with Invitrogen's protocol. After 48 hours, the cells were lysed using a mammalian protein extraction buffer (GE healthcare), and then proteins were quantified using a Bradford assay. 10 μg of the protein of each sample was electrophoresed using 12% SDS-PAGE at 80 V for 20 minutes and at 120 V for 1 hour, and then transferred onto a PVDE membrane (Bio-Rad) at 300 mA for 1 hour and 20 minutes. After transfer, the membrane was blocked in 5% skim milk for 1 hour and allowed to react with SRD5A1 antibody (ABcam, ab110123) at a ratio of 1:2000 for 12 hours. The next day, the resulting membrane was allowed to react with anti-Goat HRP (Santa Cruz) at a ratio of 1:10000 for 1 hour, and then the expression levels of the SRD5A1 protein were compared with each other using ChemiDoc (Bio-Rad). From the results of FIG. 2, 4 asiRNAs (in Table 1, No. 48, 49, 69, and 86) capable of inhibiting SRD5A1 protein expression were selected.

[Example 3] 16 Kinds of Cp-asiRNA Targeting SRD5A1 Gene and Having Self Cell-Penetrating Ability SRD5A1 cp-asiRNAs (a total of 16 strands) were designed by applying three modification patterns to 4 kinds (in Table 1, No. 48, 49, 69, and 86) of asiRNA targeting SRD5A1 according to the number and position of 2'OMe (methyl), phosphorothioate bonds (PS), and cholesterol, and then synthesized by OliX Inc. (Korea). cp-asiRNA enhances endocytosis efficiency and stability and thus may penetrate through the cell membrane with high efficiency without the aid of a delivery vehicle to thereby inhibit target gene expression. The synthesized sense and antisense strand RNA oligonucleotides were annealed at 95° C. for 2 minutes through incubation at 37° C. for 1 hour, and cp-asiRNAs annealed by 10% polyacrylamide gel electrophoresis (PAGE) were confirmed by a UV transilluminator.

TABLE 2

16 strands of cp-asiRNA nucleotide sequences targeting SRD5A1

| No. | Name | Sequence (5'-->3') |
|---|---|---|
| 1 | SRD5A1cp-asiRNA S 48 | mUUmAUmUUmGAmAUmACmGU*mA*A* cholesterol |
| 2 | SRD5A1cp-asiRNA AS 48(2, 4) | UUACGUAUUCAAAUmAmAG*C*C*U*C |
| 3 | SRD5A1cp-asiRNA AS 48(4, 4) | UUACGUAUUCAAAUmAmAmG*mC*C*U*C |
| 4 | SRD5A1cp-asiRNA AS 48(7, 4) | UUACGUAUUCAAAUmAmAmG*mC*mC*mU*mC |
| 5 | SRD5A1cp-asiRNA S 49 | mUUmCCmAAmUGmGCmGCmUU*mC*U* cholesterol |

TABLE 2-continued 16 strands of cp-asiRNA nucleotide sequences targeting SRD5A1

| No. | Name | Sequence (5'-->3') |
|---|---|---|
| 6 | SRD5A1cp-asiRNA AS 49(2, 4) | AGAAGCGCCAUUGGmAmAA*G*C*U*U |
| 7 | SRD5A1cp-asiRNA AS 49(4, 4) | AGAAGCGCCAUUGGmAmAmA*mG*C*U*U |
| 8 | SRD5A1cp-asiRNA AS 49(7, 4) | AGAAGCGCCAUUGGmAmAmA*mG*mC*mU*mU |
| 9 | SRD5A1cp-asiRNA S 69 | mCUmAAmUCmUUmCCmUUmCU*mA*A* cholesterol |
| 10 | SRD5A1cp-asiRNA AS 69(2, 4) | UUAGAAGGAAGAUUmAmGC*U*A*U*G |
| 11 | SRD5A1cp-asiRNA AS 69(4, 4) | UUAGAAGGAAGAUUmAmGmC*mU*A*U*G |
| 12 | SRD5A1cp-asiRNA AS 69(7, 4) | UUAGAAGGAAGAUUmAmGmC*mU*mA*mU*mG |
| 13 | SRD5A1cp-asiRNA S 86 | mAUmAUmCCmUAmCUmGUmGU*mA*A* cholesterol |
| 14 | SRD5A1cp-asiRNA AS 86(2, 4) | UUACACAGUAGGAUmAmUU*C*A*A*C |
| 15 | SRD5A1cp-asiRNA AS 86(4, 4) | UUACACAGUAGGAUmAmUmU*mC*A*A*C |
| 16 | SRD5A1cp-asiRNA AS 86(7, 4) | UUACACAGUAGGAUmAmUmU*mC*mA*mA*mC | m: 2'-O-Methyl/RNA
*: phosphorothioated bond

Figure 3:
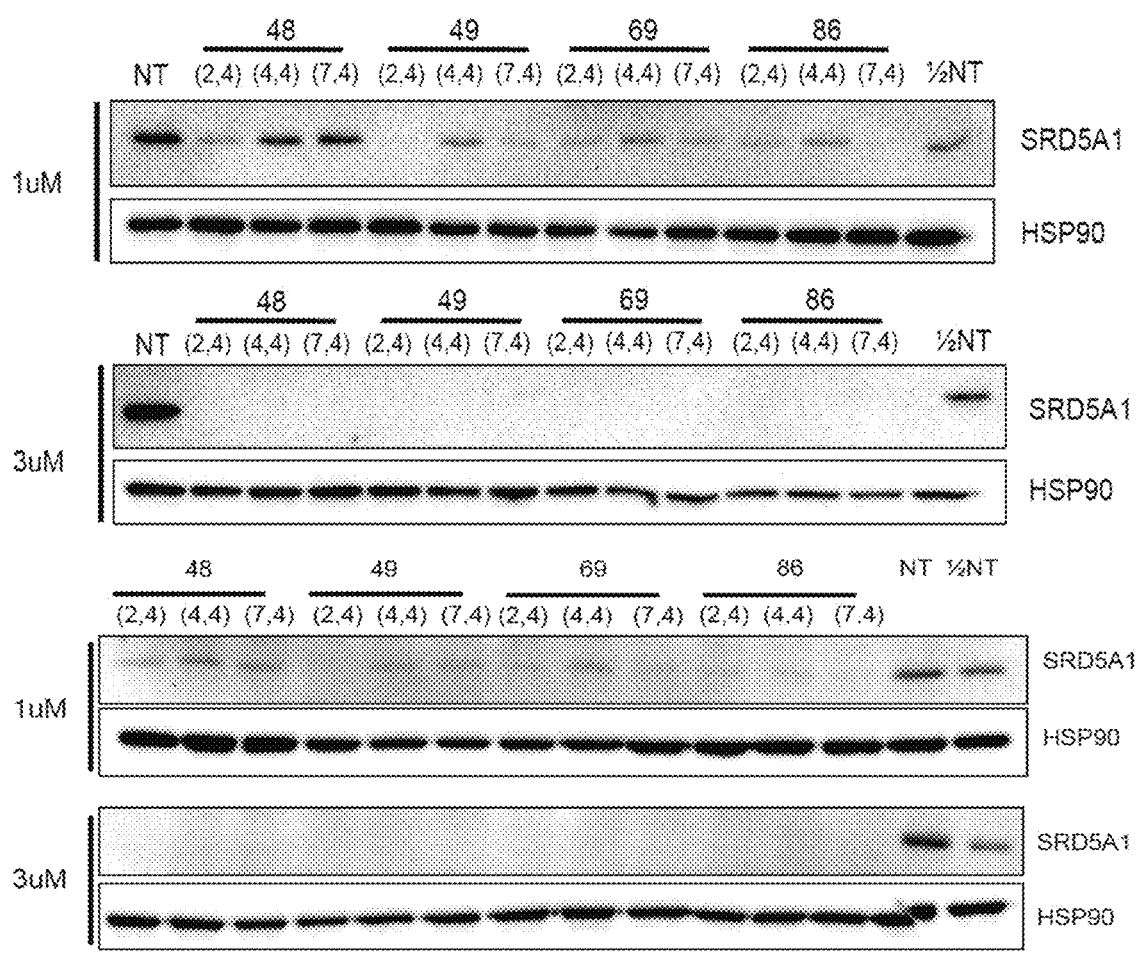
FIG. 3 illustrates results showing the gene inhibitory efficiency of 12 kinds of cp-asiRNAs targeting SRD5A1 and having various chemical modifications added thereto, through two repeated experiments. HuH-7 cells were incubated with 1 μM or 3 μM cp-asiRNA targeting each nucleotide sequence, and after 48 hours, the expression level of the SRD5A1 protein was measured by western blotting.

[Example 4] Screening for Cp-asiRNA Targeting SRD5A1 Gene and Having Self Cell-Penetrating Ability The inhibitory effects of the 12 kinds of cp-asiRNA shown in Table 2 against SRD5A1 expression were examined. A HuH-7 cell line was incubated with 1 μM or 3 μM of 12 kinds of cp-asiRNA in Opti-MEM media for 24 hours, and then the media were replaced with Dulbecco's Modified Eagle's Medium (Gibco) containing 10% fetal bovine serum (Gibco) and 100 units/ml penicillin 100 μg/ml streptomycin, and 24 hours after media replacement, SRD5A1 expression was examined at the protein level. As illustrated in FIG. 3, as the result of repeatedly conducting two experiments, it was confirmed that SRD5A1 cp-asiRNA #49(2,4) and #86 (7,4) exhibited gene inhibitory efficiency of 50% or higher.

Figure 4:
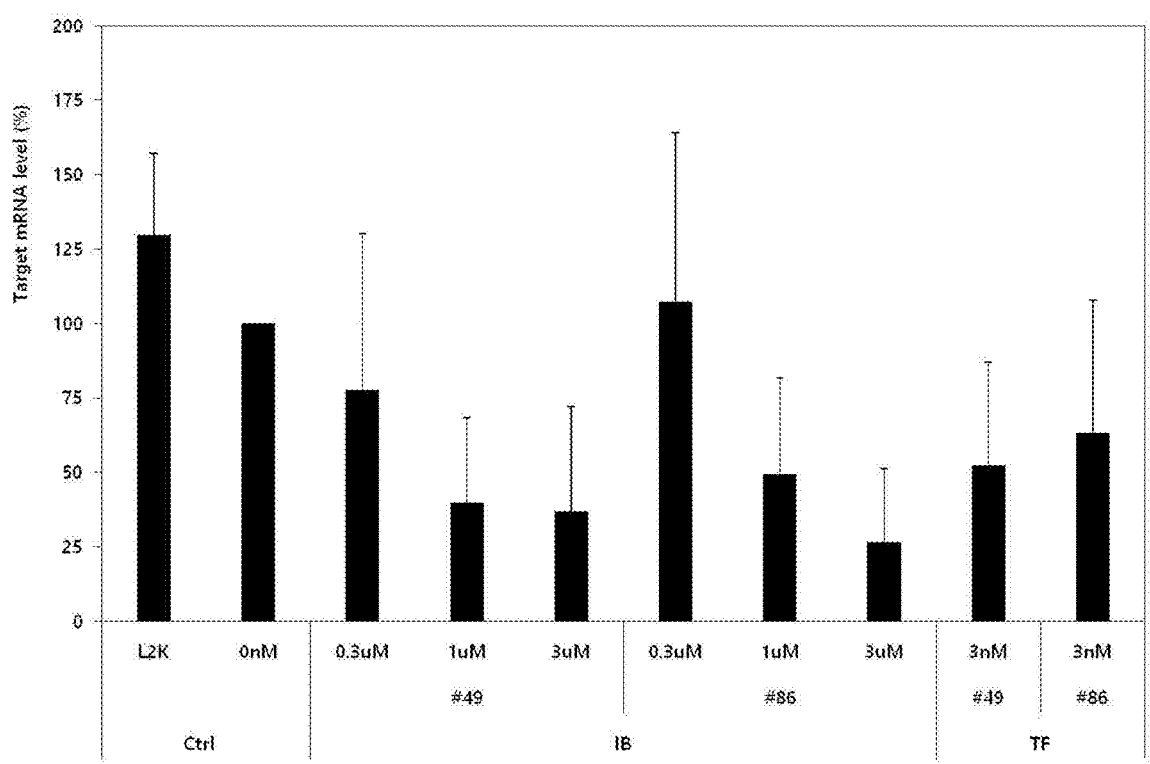
FIG. 4 illustrates results showing the gene inhibitory efficiency of 2 kinds of cp-asiRNA targeting SRD5A1 and having various chemical modifications added thereto. HuH-7 cells were incubated with 0.3 μM, 1 μM, or 3 μM cp-asiRNA targeting each nucleotide sequence, and after 24 hours, the expression level of SRD5A1 mRNA was measured using real-time PCR, and the graph shows the mean and SD of four repeated experiments.

The inhibitory effects of the two selected kinds of cp-asiRNA against SRD5A1 expression were examined in a HuH-7 cell line. The HuH-7 cell line was incubated with 0.3 μM, 1 μM, or 3 μM of each of the two kinds of cp-asiRNA in Opti-MEM media for 24 hours, and then SRD5A1 expression was examined at the mRNA level. As the result of repeatedly conducting four experiments, it was confirmed that SRD5A1 cp-asiRNA #49(2,4) and #86(7,4) exhibited gene inhibitory efficiency of 50% or higher at a concentration of 1 μM or higher (see FIG. 4).

[Example 5] Screening for 112 Kinds of RNAi-Inducing Double-Stranded Nucleic Acid Molecules Targeting SRD5A2

To obtain high-efficiency RNAi-inducing double-stranded nucleic acid molecules targeting SRD5A2, the target sequence of the SRD5A2 gene was selected and then asiRNA was designed. The asiRNA structure is different from that of generally known siRNAs, and thus when the nucleotide sequences of asiRNA are designed using a general siRNA design program, it may be somewhat difficult to design an optimized asiRNA. Therefore, asiRNA was constructed by the following method. An NCBI db search was used to obtain information on the SRD5A2 gene (mRNA Accession Number: NM_000348.3) which is thought to target male pattern hair loss (androgenetic hair loss). For subsequent animal experiments, nucleotide sequences with at least 80% homology to that of mice were secured, and then 100 kinds of asiRNA were designed according to a design method such as the exclusion of sequences having a GC content of 30-62% and 4 or more G or C consecutive bases, and then synthesized by OliX Inc. (Korea). The synthesized sense and antisense strand RNA oligonucleotides were annealed at 95° C. for 2 minutes through incubation at 37° C. for 1 hour, and the asiRNA annealed by 10% polyacrylamide gel electrophoresis (PAGE) was confirmed using a UV transilluminator.

TABLE 3

112 strands of asiRNA nucleotide sequences targeting 3-oxo-5-alpha-steroid 4-dehydrogenase 2

| 112 kinds | Sequence (5'-3') | |
|---|---|---|
| No. Name | S | AS |
| 1 asiSRD5A2 1 | GUUCCUGCAGGAGCUG (SEQ ID NO: 201) | CAGCUCCUGCAGGAACCAGGC (SEQ ID NO: 313) |
| 2 asiSRD5A2 2 | UUCCUGCAGGAGCUGC (SEQ ID NO: 202) | GCAGCUCCUGCAGGAACCAGG (SEQ ID NO: 314) |
| 3 asiSRD5A2 3 | UCCUGCAGGASCUGCC (SEQ ID NO: 203) | GGCAGCUCCUGCAGGAACCAG (SEQ ID NO: 315) |
| 4 asiSRD5A2 4 | CCUGCAGGAGCUGCCU (SEQ ID NO: 204) | AGGCAGCUCCUGCAGGAACCA (SEQ ID NO: 316) |
| 5 asiSRD5A2 5 | CUGCAGGAGCUGCCUU (SEQ ID NO: 205) | AAGGCAGCUCCUGCAGGAACC (SEQ ID NO: 317) |
| 6 asiSRD5A2 6 | UGCAGGAGCUGCCUUC (SEQ ID NO: 206) | GAAGGCAGCUCCUGCAGGAAC (SEQ ID NO: 318) |
| 7 asiSRD5A2 7 | GCAGGAGCUGCCUUCC (SEQ ID NO: 207) | GGAAGGCAGCUCCUGCAGGAA (SEQ ID NO: 319) |
| 8 asiSRD5A2 8 | CAGGAGCUGCCUUCCU (SEQ ID NO: 208) | AGGAAGGCAGCUCCUGCAGGA (SEQ ID NO: 320) |
| 9 asiSRD5A2 9 | AGGAGCUGCCUUCCUU (SEQ ID NO: 209) | AAGGAAGGCAGCUCCUGCAGG (SEQ ID NO: 321) |
| 10 asiSRD5A2 10 | ACUUCCACAGGACAUU (SEQ ID NO: 210) | AAUGUCCUGUGGAAGUAAUGU (SEQ ID NO: 322) |

TABLE 3-continued 112 strands of asiRNA nucleotide sequences targeting 3-oxo-5-alpha-steroid 4-dehydrogenase 2

| No. | Name | Sequence (5'-3') S | AS |
|---|---|---|---|
| 11 | asiSRD5A2 11 | CUUCCACAGGACAUUU (SEQ ID NO: 211) | AAAUGUCCUGUGGAAGUAAUG (SEQ ID NO: 323) |
| 12 | asiSRD5A2 12 | AGGUGGCUUGUUUACG (SEQ ID NO: 212) | CGUAAACAAGCCACCUUGUGG (SEQ ID NO: 324) |
| 13 | asiSRD5A2 13 | GGUGGCUUGUUUACGU (SEQ ID NO: 213) | ACGUAAACAAGCCACCUUGUG (SEQ ID NO: 325) |
| 14 | asiSRD5A2 14 | GUGGCUUGUUUACGUA (SEQ ID NO: 214) | UACGUAAACAAGCCACCUUGU (SEQ ID NO: 326) |
| 15 | asiSRD5A2 15 | UGGCUUGUUUACGUAU (SEQ ID NO: 215) | AUACGUAAACAAGCCACCUUG (SEQ ID NO: 327) |
| 16 | asiSRD5A2 16 | GGCUUGUUUACGUAUG (SEQ ID NO: 216) | CAUACGUAAACAAGCCACCUU (SEQ ID NO: 328) |
| 17 | asiSRD5A2 17 | GCUUGUUUACGUAUGU (SEQ ID NO: 217) | ACAUACGUAAACAAGCCACCU (SEQ ID NO: 329) |
| 18 | asiSRD5A2 18 | CUACCUCAAGAUGUUU (SEQ ID NO: 218) | AAACAUCUUGAGGUAGAACCU (SEQ ID NO: 330) |
| 19 | asiSRD5A2 19 | GGUUCCUGCAGGAGCU (SEQ ID NO: 219) | AGCUCCUGCAGGAACCAGGCG (SEQ ID NO: 331) |
| 20 | asiSRD5A2 20 | UACUUCCACAGGACAU (SEQ ID NO: 220) | AUGUCCUGUGGAAGUAAUGUA (SEQ ID NO: 332) |
| 21 | asiSRD5A2 21 | AGACAUACGGUUUAGC (SEQ ID NO: 221) | GCUAAACCGUAUGUCUGUGUA (SEQ ID NO: 333) |
| 22 | asiSRD5A2 22 | CAGACAUACGGUUUAG (SEQ ID NO: 222) | CUAAACCGUAUGUCUGUGUAC (SEQ ID NO: 334) |
| 23 | asiSRD5A2 23 | ACAGACAUACGGUUUA (SEQ ID NO: 223) | UAAACCGUAUGUCUGUGUACC (SEQ ID NO: 335) |
| 24 | asiSRD5A2 24 | CACAGACAUACGGUUU (SEQ ID NO: 224) | AAACCGUAUGUCUGUGUACCA (SEQ ID NO: 336) |
| 25 | asiSRD5A2 25 | GGAUUCCACAAGGUGG (SEQ ID NO: 225) | CCACCUUGUGGAAUCCUGUAG (SEQ ID NO: 337) |
| 26 | asiSRD5A2 26 | GAUUCCACAAGGUGGC (SEQ ID NO: 226) | GCCACCUUGUGGAAUCCUGUA (SEQ ID NO: 338) |
| 27 | asiSRD5A2 27 | AUUCCACAAGGUGGCU (SEQ ID NO: 227) | AGCCACCUUGUGGAAUCCUGU (SEQ ID NO: 339) |
| 28 | asiSRD5A2 28 | UUCCACAAGGUGGCUU (SEQ ID NO: 228) | AAGCCACCUUGUGGAAUCCUG (SEQ ID NO: 340) |
| 29 | asiSRD5A2 29 | UCCACAAGGUGGCUUG (SEQ ID NO: 228) | CAAGCCACCUUGUGGAAUCCU (SEQ ID NO: 341) |
| 30 | asiSRD5A2 30 | CCACAAGGUGGCUUGU (SEQ ID NO: 230) | ACAAGCCACCUUGUGGAAUCC (SEQ ID NO: 342) |
| 31 | asiSRD5A2 31 | CACAAGGUGGCUUGUU (SEQ ID NO: 231) | AACAAGCCACCUUGUGGAAUC (SEQ ID NO: 343) |
| 32 | asiSRD5A2 32 | ACAAGGUGGCUUGUUU (SEQ ID NO: 232) | AAACAAGCCACCUUGUGGAAU (SEQ ID NO: 344) |
| 33 | asiSRD5A2 33 | CAAGGUGGCUUGUUUA (SEQ ID NO: 233) | UAAACAAGCCACCUUGUGGAA (SEQ ID NO: 345) |
| 34 | asiSRD5A2 34 | AAGGUGGCUUGUUUAC (SEQ ID NO: 234) | GUAAACAAGCCACCUUGUGGA (SEQ ID NO: 346) |
| 35 | asiSRD5A2 35 | CUGGAGCCAAUUUCCU (SEQ ID NO: 235) | AGGAAAUUGGCUCCAGAAACA (SEQ ID NO: 347) |
| 36 | asiSRD5A2 36 | UCUGGAGCCAAUUUCC (SEQ ID NO: 236) | GGAAAUUGGCUCCAGAAACAU (SEQ ID NO: 348) |
| 37 | asiSRD5A2 37 | UUCUGGAGCCAAUUUC (SEQ ID NO: 237) | GAAAUUGGCUCCAGAAACAUA (SEQ ID NO: 349) |
| 38 | asiSRD5A2 38 | UUUCUGGAGCCAAUUU (SEQ ID NO: 238) | AAAUUGGCUCCAGAAACAUAC (SEQ ID NO: 350) |
| 39 | asiSRD5A2 39 | GUUUCUGGAGCCAAUU (SEQ ID NO: 239) | AAUUGGCUCCAGAAACAUACG (SEQ ID NO: 351) |
| 40 | asiSRD5A2 40 | UGUUUCUGGAGCCAAU (SEQ ID NO: 240) | AUUGGCUCCAGAAACAUACGU (SEQ ID NO: 352) |
| 41 | asiSRD5A2 41 | AUGUUUCUGGAGCCAA (SEQ ID NO: 241) | UUGGCUCCAGAAACAUACGUA (SEQ ID NO: 353) |
| 42 | asiSRD5A2 42 | UAUGUUUCUGGAGCCA (SEQ ID NO: 242) | UGGCUCCAGAAACAUACGUAA (SEQ ID NO: 354) |
| 43 | asiSRD5A2 43 | GUAUGUUUCUGGAGCC (SEQ ID NO: 243) | GGCUCCAGAAACAUACGUAAA (SEQ ID NO: 355) |
| 44 | asiSRD5A2 44 | GCUCCAGAAACAUACG (SEQ ID NO: 244) | GCUCCAGAAACAUACGUAAAC (SEQ ID NO: 356) |
| 45 | asiSRD5A2 45 | CAUAGGUUCUACCUCA (SEQ ID NO: 245) | UGAGGUAGAACCUAUGGUCGU (SEQ ID NO: 357) |
| 46 | asiSRD5A2 46 | AUAGGUUCUACCUCAA (SEQ ID NO: 246) | UUGAGGUAGAACCUAUGGUGG (SEQ ID NO: 358) |
| 47 | asiSRD5A2 47 | UAGGUUCUACCUCAAG (SEQ ID NO: 247) | CUUGAGGUAGAACCUAUGGUG (SEQ ID NO: 359) |
| 48 | asiSRD5A2 48 | AGGUUCUACCUCAAGA (SEQ ID NO: 248) | UCUUGAGGUAGAACCUAUGGU (SEQ ID NO: 360) |
| 49 | asiSRD5A2 49 | GGUUCUACCUCAAGAU (SEQ ID NO: 249) | AUCUUGAGGUAGAACCUAUGG (SEQ ID NO: 361) |
| 50 | asiSRD5A2 50 | GUUCUACCUCAAGAUG (SEQ ID NO: 250) | CAUCUUGAGGUAGAACCUAUG (SEQ ID NO: 362) |
| 51 | asiSRD5A2 51 | UUCUACCUCAAGAUGU (SEQ ID NO: 251) | ACAUCUUGAGGUAGAACCUAU (SEQ ID NO: 363) |
| 52 | asiSRD5A2 52 | UCUACCUCAAGAUGUU (SEQ ID NO: 252) | AACAUCUUGAGGUAGAACCUA (SEQ ID NO: 364) |
| 53 | asiSRD5A2 53 | CAAAUCUCGGAAAGCC (SEQ ID NO: 253) | GGCUUUCCGAGAUUUGGGUA (SEQ ID NO: 365) |
| 54 | asiSRD5A2 54 | AAAUCUCGGAAAGCCC (SEQ ID NO: 254) | GGGCUUUCCGAGAUUUGGGGU (SEQ ID NO: 366) |
| 55 | asiSRD5A2 55 | AAUCUCGGAAAGCCCU (SEQ ID NO: 255) | AGGGCUUUCCGAGAUUUGGGG (SEQ ID NO: 367) |
| 56 | asiSRD5A2 56 | GCCCUUAUUCCAUUCA (SEQ ID NO: 256) | UGAAUGGAAUAAGGGCUUUCC (SEQ ID NO: 368) |
| 57 | asiSRD5A2 57 | CCCUUAUUCCAUUCAU (SEQ ID NO: 257) | AUGAAUGGAAUAAGGGCUUUC (SEQ ID NO: 369) |
| 58 | asiSRD5A2 58 | CCUUAUUCCAUUCAUC (SEQ ID NO: 258) | GAUGAAUGGAAUAAGGGCUUU (SEQ ID NO: 370) |

TABLE 3-continued

112 strands of asiRNA nucleotide sequences targeting 3-oxo-5-alpha-steroid 4-dehydrogenase 2

| No. | Name | Sequence (5'-3') S | Sequence (5'-3') AS |
|---|---|---|---|
| 59 | asiSRD5A2 59 | CUUAUUCCAUUCAUCU (SEQ ID NO: 259) | AGAUGAAUGGAAUAAGGGCUU (SEQ ID NO: 371) |
| 60 | asiSRD5A2 60 | UUAUUCCAUUCAUCUU (SEQ ID NO: 260) | AAGAUGAAUGGAAUAAGGGCU (SEQ ID NO: 372) |
| 61 | asiSRD5A2 61 | UAUUCCAUUCAUCUUU (SEQ ID NO: 261) | AAAGAUGAAUGGAAUAAGGGC (SEQ ID NO: 373) |
| 62 | asiSRD5A2 62 | AUUCCAUUCAUCUUUU (SEQ ID NO: 262) | AAAAGAUGAAUGGAAUAAGGG (SEQ ID NO: 374) |
| 63 | asiSRD5A2 63 | UUCCAUUCAUCUUUUA (SEQ ID NO: 263) | UAAAAGAUGAAUGGAAUAAGG (SEQ ID NO: 375) |
| 64 | asiSRD5A2 64 | UCCAUUCAUCUUUUAA (SEQ ID NO: 264) | UUAAAAGAUGAAUGGAAUAAG (SEQ ID NO: 376) |
| 65 | asiSRD5A2 65 | UCUCACUUUGUUUCCU (SEQ ID NO: 265) | AGGAAACAAAGUGAGAAAAAU (SEQ ID NO: 377) |
| 66 | asiSRD5A2 66 | UUCUCACUUUGUUUCC (SEQ ID NO: 266) | GGAAACAAAGUGAGAAAAAUG (SEQ ID NO: 378) |
| 67 | asiSRD5A2 67 | UUUCUCACUUUGUUUC (SEQ ID NO: 267) | GAAACAAAGUGAGAAAAAUGC (SEQ ID NO: 379) |
| 68 | asiSRD5A2 68 | UUUUCUCACUUUGUUU (SEQ ID NO: 268) | AAACAAAGUGAGAAAAAUGCA (SEQ ID NO: 380) |
| 69 | asiSRD5A2 69 | UUUUUCUCACUUUGUU (SEQ ID NO: 269) | AACAAAGUGAGAAAAAUGCAA (SEQ ID NO: 381) |
| 70 | asiSRD5A2 70 | AUUUUUCUCACUUUGU (SEQ ID NO: 270) | ACAAAGUGAGAAAAAUGCAAA (SEQ ID NO: 382) |
| 71 | asiSRD5A2 71 | UGGCAGGCAGCGCCAC (SEQ ID NO: 271) | GUGGCGCUGCCUGCCAGCACU (SEQ ID NO: 363) |
| 72 | asiSRD5A2 72 | CUGGCAGGCAGCGCCA (SEQ ID NO: 272) | UGGCGCUGCCUGCCAGCACUG (SEQ ID NO: 384) |
| 73 | asiSRD5A2 73 | GGCAGGCAGCGCCACU (SEQ ID NO: 273) | AGUGGCGCUGCCUGCCAGCAC (SEQ ID NO: 385) |
| 74 | asiSRD5A2 74 | UGCCAGCCCGCGCCGC (SEQ ID NO: 274) | GCGGCGCGGGCUGGCAGGCGG (SEQ ID NO: 386) |
| 75 | asiSRD5A2 75 | UUACUUCCACAGGACA (SEQ ID NO: 275) | UGUCCUGUGGAAGUAAUGUAG (SEQ ID NO: 387) |
| 76 | asiSRD5A2 76 | GUGGAAGUAAUGUAGG (SEQ ID NO: 276) | CCUACAUUACUUCCACAGGAC (SEQ ID NO: 388) |
| 77 | asiSRD5A2 77 | CCCUGAUGGGUGGUAC (SEQ ID NO: 277) | GUACCACCCAUCAGGGUAUUC (SEQ ID NO: 389) |
| 78 | asiSRD5A2 78 | CCUGAUGGGUGGUACA (SEQ ID NO: 278) | UGUACCACCCAUCAGGGUAUU (SEQ ID NO: 390) |
| 79 | asiSRD5A2 79 | CUGAUGGGUGGUACAC (SEQ ID NO: 279) | GUGUACCACCCAUCAGGGUAU (SEQ ID NO: 391) |
| 80 | asiSRD5A2 80 | UGAUGGGUGGUACACA (SEQ ID NO: 280) | UGUGUACCACCCAUCAGGGUA (SEQ ID NO: 392) |
| 81 | asiSRD5A2 81 | GAUGGGUGGUACACAG (SEQ ID NO: 281) | CUGUGUACCACCCAUCAGGGU (SEQ ID NO: 393) |
| 82 | asiSRD5A2 82 | AUGGGUGGUACACAGA (SEQ ID NO: 282) | UCUGUGUACCACCCAUCAGGG (SEQ ID NO: 394) |
| 83 | asiSRD5A2 83 | UGGGUGGUACACAGAC (SEQ ID NO: 283) | GUCUGUGUACCACCCAUCAGG (SEQ ID NO: 395) |
| 84 | asiSRD5A2 84 | GGGUGGUACACAGACA (SEQ ID NO: 284) | UGUCUGUGUACCACCCAUCAG (SEQ ID NO: 396) |
| 85 | asiSRD5A2 85 | GGUGGUACACAGACAU (SEQ ID NO: 285) | AUGUCUGUGUACCACCCAUCA (SEQ ID NO: 397) |
| 86 | asiSRD5A2 86 | GACAUACGGUUUAGCU (SEQ ID NO: 286) | AGCUAAACCGUAUGUCUGUGU (SEQ ID NO: 390) |
| 87 | asiSRD5A2 87 | CUUGGGUGUCUUCUUA (SEQ ID NO: 287) | UAAGAAGACACCCAAGCUAAA (SEQ ID NO: 399) |
| 88 | asiSRD5A2 88 | GCUUGGGUGUCUUCUU (SEQ ID NO: 288) | AAGAAGACACCCAAGCUAAAC (SEQ ID NO: 400) |
| 89 | asiSRD5A2 89 | AGCUUGGGUGUCUUCU (SEQ ID NO: 289) | AGAAGACACCCAAGCUAAACC (SEQ ID NO: 401) |
| 90 | asiSRD5A2 90 | UAGCUUGGGUGUCUUC (SEQ ID NO: 290) | GAAGACACCCAAGCUAAACCG (SEQ ID NO: 402) |
| 91 | asiSRD5A2 91 | GCCAGCUCAGGAAGCC (SEQ ID NO: 291) | GGCUUCCUGAGCUGGCGCAAU (SEQ ID NO: 403) |
| 92 | asiSRD5A2 92 | CGCCAGCUCAGGAAGC (SEQ ID NO: 292) | GCUUCCUGAGCUGGCGCAAUA (SEQ ID NO: 404) |
| 93 | asiSRD5A2 93 | GCGCCAGCUCAGGAAG (SEQ ID NO: 293) | CUUCCUGAGCUGGCGCAAUAU (SEQ ID NO: 405) |
| 94 | asiSRD5A2 94 | UGGAGCCAAUUUCCUC (SEQ ID NO: 294) | GAGGAAAUUGGCUCCAGAAAC (SEQ ID NO: 406) |
| 95 | asiSRD5A2 95 | CUCACUUUGUUUCCUU (SEQ ID NO: 295) | AAGGAAACAAAGUGAGAAAAA (SEQ ID NO: 407) |
| 96 | asiSRD5A2 96 | CAUUUUUCUCACUUUG (SEQ ID NO: 296) | CAAAGUGAGAAAAAUGCAAAU (SEQ ID NO: 408) |
| 97 | asiSRD5A2 97 | CCAUAGGUUCUACCUC (SEQ ID NO: 297) | GAGGUAGAACCUAUGGUGGUG (SEQ ID NO: 409) |
| 98 | asiSRD5A2 98 | ACCAUAGGUUCUACCU (SEQ ID NO: 298) | AGGUAGAACCUAUGGUGGUGA (SEQ ID NO: 410) |
| 99 | asiSRD5A2 99 | CACCAUAGGUUCUACC (SEQ ID NO: 299) | GGUAGAACCUAUGGUGGUGAA (SEQ ID NO: 411) |
| 100 | asiSRD5A2 100 | CCACCAUAGGUUCUAC (SEQ ID NO: 300) | GUAGAACCUAUGGUGGUGAAA (SEQ ID NO: 412) |
| 101 | asiSRD5A2 101 | ACCACCAUAGGUUCUA (SEQ ID NO: 301) | UAGAACCUAUGGUGGUGAAAA (SEQ ID NO: 413) |
| 102 | asiSRD5A2 102 | CACCACCAUAGGUUCU (SEQ ID NO: 302) | AGAACCUAUGGUGGUGAAAAG (SEQ ID NO: 414) |
| 103 | asiSRD5A2 103 | GGACUACCCCAAAUCU (SEQ ID NO: 303) | AGAUUUGGGGUAGUCCUCAAA (SEQ ID NO: 415) |
| 104 | asiSRD5A2 104 | AGGACUACCCCAAAUC (SEQ ID NO: 304) | GAUUUGGGGUAGUCCUCAAAC (SEQ ID NO: 416) |
| 105 | asiSRD5A2 105 | GAGGACUACCCCAAAU (SEQ ID NO: 305) | AUUUGGGGUAGUCCUCAAACA (SEQ ID NO: 417) |
| 106 | asiSRD5A2 106 | UGAGGACUACCCCAAA (SEQ ID NO: 306) | UUUGGGGUAGUCCUCAAACAU (SEQ ID NO: 418) |

TABLE 3-continued 112 strands of asiRNA nucleotide sequences targeting 3-oxo-5-alpha-steroid 4-dehydrogenase 2

| 112 kinds | | Sequence (5'-3') | |
|---|---|---|---|
| No. | Name | S | AS |
| 107 | asiSRD5A2 107 | UUGAGGACUACCCCAA (SEQ ID NO: 307) | UUGGGGUAGUCCUCAAACAUC (SEQ ID NO: 419) |
| 108 | asiSRD5A2 108 | UUUGAGGACUACCCCA (SEQ ID NO: 308) | UGGGGUAGUCCUCAAACAUCU (SEQ ID NO: 420) |
| 109 | asiSRD5A2 109 | CCAAAUCUCGGAAAGC (SEQ ID NO: 309) | GCUUUCCGAGAUUUGGGGUAG (SEQ ID NO: 421) |
| 110 | asiSRD5A2 110 | AGCCCUUAUUCCAUUC (SEQ ID NO: 310) | GAAUGGAAUAAGGGCUUUCCG (SEQ ID NO: 422) |
| 111 | asiSRD5A2 111 | AAGCCCUUAUUCCAUU (SEQ ID NO: 311) | AAUGGAAUAAGGGCUUUCCGA (SEQ ID NO: 423) |
| 112 | asiSRD5A2 112 | GGCUAUGCCCUGGCCA (SEQ ID NO: 312) | UGGCCAGGGCAUAGCCGAUCC (SEQ ID NO: 424) |

[Example 6] Screening for RNAi-Inducing Double-Stranded Nucleic Acid Molecules Targeting SRD5A2

Figure 5A:
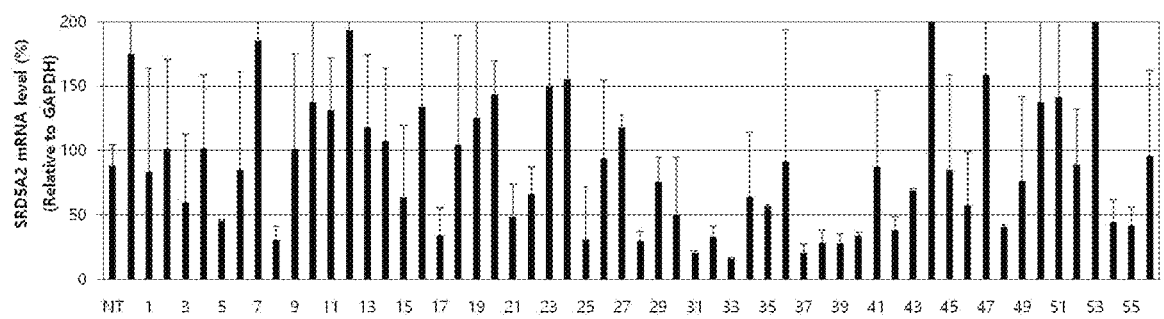
FIGS. 5A and 5B illustrate results showing the gene inhibitory efficiency of asiRNA against 112 sequences targeting SRD5A2. HuH-7 cells were transfected with 0.3 nM asiRNA targeting each nucleotide sequence, and after 24 hours, the expression level of SRD5A2 mRNA was measured using qRT-PCR, and the graphs show the mean and SD of two repeated experiments.
Figure 5B:
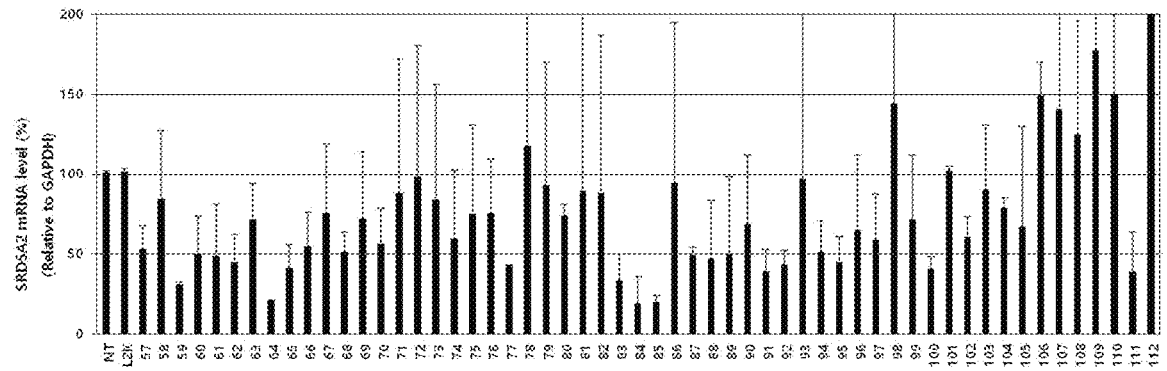

To confirm gene inhibitory efficiency at the mRNA level, 112 selected kinds of asiRNA were transfected into a HuH-7 cell line at a concentration of 0.3 nM, and qRT-PCR was performed to measure the expression level of SRD5A1 mRNA. The HuH-7 cell line was cultured in Dulbecco's Modified Eagle's Medium (DMEM, Gibco) containing 10% fetal bovine serum (FBS, Gibco) and 100 units/ml of penicillin 100 µg/ml of streptomycin. HuH-7 cells were seeded in a 24-well plate at a density of 5×10⁴ cells/well, and a reverse transfection experiment was conducted using asiRNA (0.3 nM, OliX Inc.) and Lipofectamine 2000 (1 µl/ml, Invitrogen Inc.) in Opti-MEM (a total volume of 500 µl) in accordance with Invitrogen's protocol. After 24 hours, total RNA was extracted using TRIzol (TaKaPa), and then cDNA was synthesized using a high-capacity cDNA reverse transcription kit (Applied Biosystems), and the expression level of the SRD5A2 gene was examined using power SYBR green PCR master Mix (Applied Biosystems), the following primers, and a StepOne real-time PCR system (see FIGS. 5A and 5B).

The nucleotide sequences of the primers used in the experiment are shown in Table 4 below.

TABLE 4

Primer nucleotide sequences

| Name | | Sequence (5'-3') | size |
|---|---|---|---|
| Human GAPDH | Forward | GAG TCA ACG GAT TTG GTC GT (SEQ ID NO: 425) | 186 |
| | Reverse | GAC AAG CTT CCC GTT CTC AG (SEQ ID NO: 426) | |
| Human SRD5A2 | Forward | TGA ACC TGG GTG GCT TAT GA (SEQ ID NO: 427) | 242 |
| | Reverse | GAA AGG AAA GTT GCT TGG G (SEQ ID NO: 428) | |

Figure 6A:
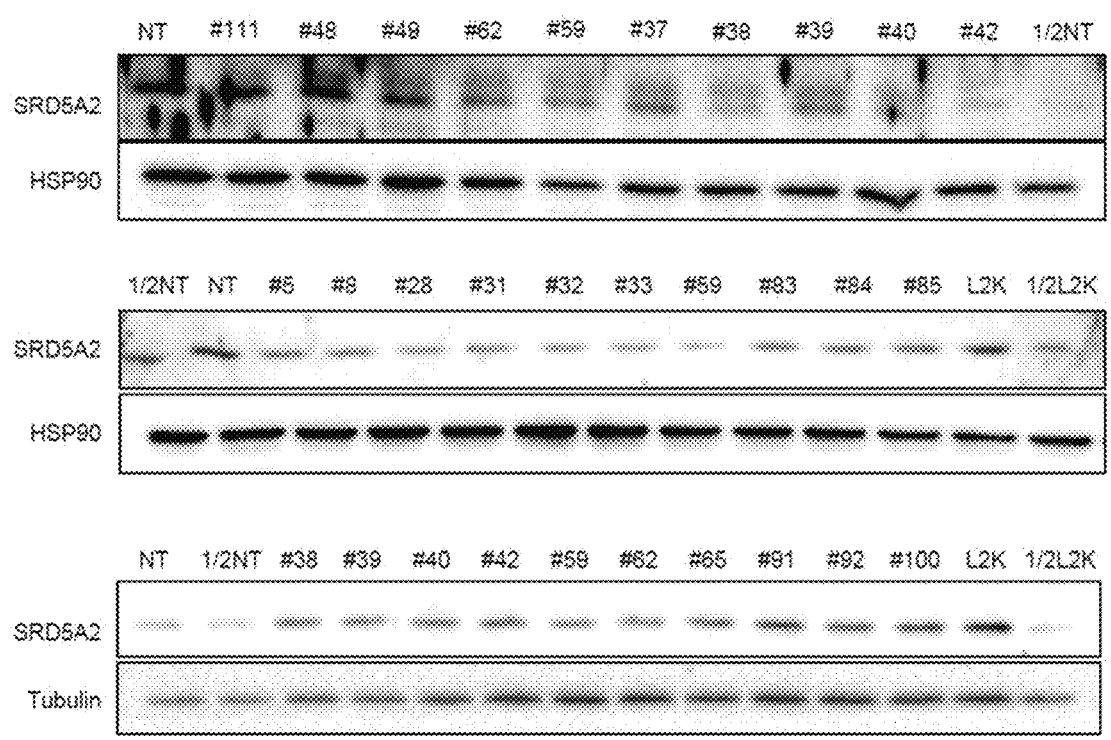
FIG. 6A illustrates results showing the gene inhibitory efficiency of asiRNA against 23 sequences targeting SRD5A2.
Figure 6B:
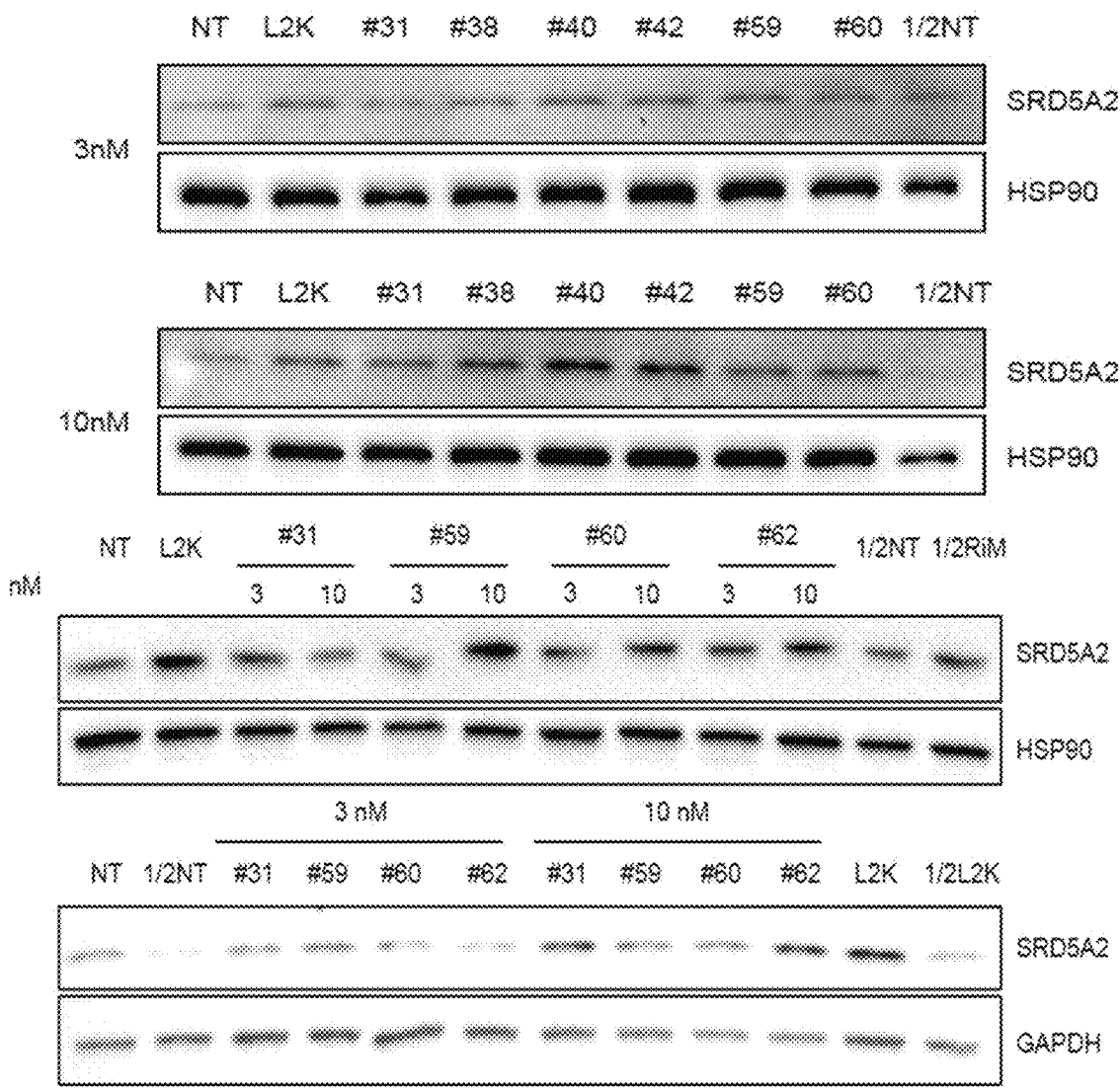
FIG. 6B illustrates results showing the gene inhibitory efficiency of asiRNA against 6 sequences and 4 sequences, which target SRD5A2. HuH-7 cells were transfected with 3 nM or 10 nM of asiRNA targeting each nucleotide sequence, and after 48 hours, the expression level of the SRD5A2 protein was measured by western blotting.

From the results of screening 112 asiRNAs, the 23 top-ranked asiRNAs (in Table 3, No. 5, 8, 28, 31, 32, 33, 37, 38, 39, 40, 42, 48, 49, 59, 60, 62, 65, 83, 84, 85, 91, 92, and 100) were selected, and western blotting was performed at a concentration of 10 nM. HuH-7 cells were seeded in a 6-well plate at a density of 2.5×10³ cells/well, and then a reverse transfection experiment was conducted using asiRNA and Lipofectamine 2000 (1 µl/ml, Invitrogen Inc.) in Opti-MEM (a total volume of 2 ml) in accordance with Invitrogen's protocol. After 48 hours, the cells were lysed using a mammalian protein extraction buffer (GE healthcare), and then proteins were quantified using a Bradford assay. 10 µg of the protein of each sample was electrophoresed using 12% SDS-PAGE at 80 V for 20 minutes and at 120 V for 1 hour, and then transferred onto a PVDE membrane (Bio-Rad) at 300 mA for 1 hour and 20 minutes. After transfer, the membrane was blocked in 5% skim milk for 1 hour and then allowed to react with SRD5A2 antibody (ABcam, ab124877) at a ratio of 1:2000 for 12 hours. The next day, the resulting membrane was allowed to react with anti-Rabbit HRP (Santa Cruz) at a ratio of 1:10000 for 1 hour, and then the expression levels of the SRD5A2 protein were compared with each other using ChemiDoc (Bio-Rad). In the present experiment, 4 asiRNAs (in Table 3, No. 31, 59, 60, and 62) capable of inhibiting SRD5A2 protein expression by about 50% or higher were selected (see FIGS. 6A and 6B).

[Example 7] 16 Kinds of Cp-asiRNA Targeting SRD5A2 Gene and Having Self Cell-Penetrating Ability SRD5A2 cp-asiRNAs (total 16 strands) were designed by applying three modification patterns to 4 kinds (in Table 3, No. 31, 59, 60, and 62) of asiRNA targeting SRD5A2 according to the number and position of 2'OMe (methyl), phosphorothioate bonds (PS), and cholesterol, and then synthesized by OliX Inc. (Korea). cp-asiRNA enhances endocytosis efficiency and stability and thus may penetrate through the cell membrane with high efficiency without the aid of a delivery vehicle to thereby inhibit the expression of the target gene. The synthesized sense and antisense strand RNA oligonucleotides were annealed at 95° C. for 2 minutes through incubation at 37° C. for 1 hour, and cp-asiRNAs annealed by 10% polyacrylamide gel electrophoresis (PAGE) were confirmed using a UV transilluminator.

TABLE 5

16 strands of cp-asiRNA nucleotide sequences targeting SRD5A2

| No. | Name | Sequence (5'-->3') |
|---|---|---|
| 1 | SRD5A2cp-asiRNA S 31 | mCAmCAmAGmGUmGCmCUmU*G*mU*U cholesterol |
| 2 | SRD5A2cp-asiRNA AS 31(2, 4) | AACAAGCCACCUUGmUmGG*A*A*U*C |
| 3 | SRD5A2cp-asiRNA AS 31(4, 4) | AACAAGCCACCUUGmUmSmG*mA*A*U*C |
| 4 | SRD5A2cp-asiRNA AS 31(7, 4) | AACAAGCCACCUUGmUmGmG*mA*mA*mU*mC |

TABLE 5-continued 16 strands of cp-asiRNA nucleotide sequences targeting SRD5A2

| No. | Name | Sequence (5'-->3') |
|---|---|---|
| 5 | SRD5A2cp-asiRNA S 59 | mCUmUAmUUmCCmAUMUCmA*U*mC*U cholesterol |
| 6 | SRD5A2cp-asiRNA AS 59(2, 4) | AGAUGAAUGGAAUAmAmGG*G*C*U*U |
| 7 | SRD5A2cp-asiRNA AS 59(4, 4) | AGAUGAAUGGAAUAmAmGmG*mG*C*U*U |
| 8 | SRD5A2cp-asiRNA AS 59(7, 4) | AGAUGAAUGGAAUAmAmGmG*mG*mC*mU*mU |
| 9 | SRD5A2cp-asiRNA S 60 | mUUmAUmUCmCAmUUmCAmU*C*mU*U cholesterol |
| 10 | SRD5A2cp-asiRNA AS 60(2, 4) | AAGAUGAAUGGAAUmAmAG*G*G*C*U |
| 11 | SRD5A2cp-asiRNA AS 60(4, 4) | AAGAUGAAUGGAAUmAmAmG*mG*G*C*U |
| 12 | SRD5A2cp-asiRNA AS 60(7, 4) | AAGAUGAAUGGAAUmAmAmG*mG*mG*mC*mU |
| 13 | SRD5A2cp-asiRNA S 62 | mAUmUCmCAmUUmCAmUC*mU*U*mU*U cholesterol |
| 14 | SRD5A2cp-asiRNA AS 62(2, 4) | AAAAGAUGAAUGGAmAmUA*A*G*G*G |
| 15 | SRD5A2cp-asiRNA AS 62(4, 4) | AAAAGAUGAAUGGAmAmUmA*mA*G*G*G |
| 16 | SRD5A2cp-asiRNA AS 62(7, 4) | AAAAGAUGAAUGGAmAmUmA*mA*mG*mG*mG | m: 2'-O-Methyl/RNA
*: phosphorothioated bond

Figure 7:
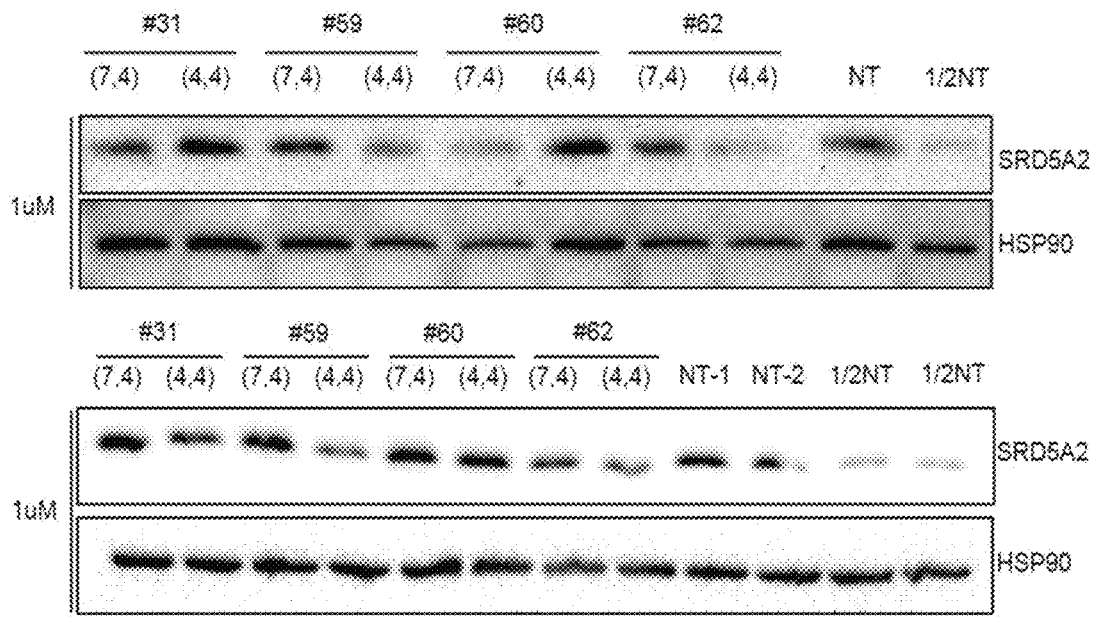
FIG. 7 illustrates results showing the gene inhibitory efficiency of 12 kinds of cp-asiRNA targeting SRD5A2 and having various chemical modifications added thereto, through two repeated experiments. HuH-7 cells were incubated with 1 μM of cp-asiRNA targeting each nucleotide sequence, and after 48 hours, the expression level of the SRD5A2 protein was measured by western blotting.

[Example 8] Screening for Cp-asiRNA Targeting SRD5A2 Gene and Having Self Cell-Penetrating Ability The inhibitory effects of the 12 kinds of cp-asiRNA shown in Table 5 against SRD5A2 expression were examined. A HuH-7 cell line was incubated with 1 µM or 3 µM of 12 kinds of cp-asiRNA in Opti-MEM media for 24 hours, and then the media were replaced with Dulbecco's Modified Eagle's Medium (Gibco) containing 10% fetal bovine serum (Gibco) and 100 units/ml penicillin 100 µg/ml streptomycin, and 24 hours after media replacement, SRD5A2 expression was examined at the protein level. As the result of repeatedly conducting two experiments, it was confirmed that SRD5A2 cp-asiRNA #59(4,4) and #62(4,4) exhibited gene inhibitory efficiency of 50% or higher (see FIG. 7).

Figure 8:
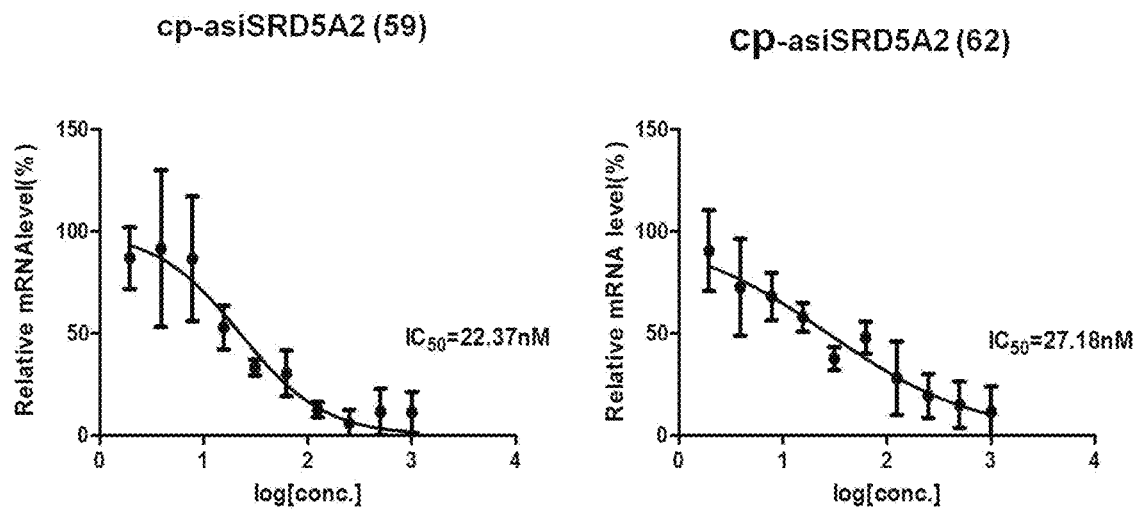
FIG. 8 illustrates results showing the gene inhibitory efficiency of 2 selected kinds of cp-asisRD5A2. HuH-7 cells were incubated with cp-asiRNA targeting each nucleotide sequence at a concentration ranging from 1.95 nM to 1,000 nM, and after 24 hours, the expression level of SRD5A2 mRNA was measured by RT-PCR.

[Example 9] Confirmation of Inhibitory Efficiency of 2 Selected Kinds of Cp-asiRNA Against Target Gene SRD5A2 Expression The inhibitory effects of the two above-selected kinds of cp-asiRNA against SRD5A2 expression were examined in a HuH-7 cell line. The HuH-7 cell line was incubated in Opti-MEM media with 1.95 nM, 3.9 nM, 7.8 nM, 15.6 nM, 31.3 nM, 62.5 nM, 125 nM, 250 nM, 500 nM, or 1,000 nM of each of the two kinds of cp-asiRNA for 24 hours, and then SRD5A2 expression was examined at the mRNA level. As the result of repeatedly conducting three experiments, it was confirmed that SRD5A2 cp-asiRNA #59(4,4) and #62(4,4) had $IC_{50}$ values of 22.37 nM and 27.18 nM, respectively (see FIG. 8).

Figure 9:
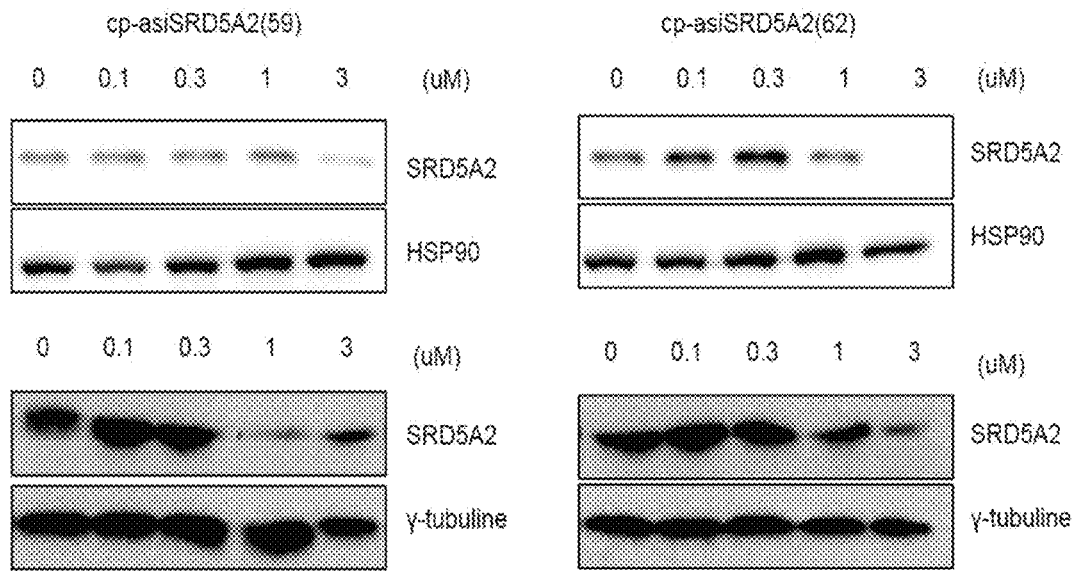
FIG. 9 illustrates results showing the gene inhibitory efficiency of 2 selected kinds of cp-asiSRD5A2. HuH-7 cells were incubated with 0.1 μM, 0.3 μM, 1 μM, or 3 μM of cp-asiRNA targeting each nucleotide sequence, and after 48 hours, the expression level of the SRD5A2 protein was measured by western blotting.

The inhibitory effects of the two above-selected kinds of cp-asiRNA against SRD5A2 expression were examined in a HuH-7 cell line. The HuH-7 cell line was incubated with 0.1 µM, 0.3 µM, 1 µM, or 3 µM of the two kinds of cp-asiRNA in Opti-MEM media for 24 hours, and then the media were replaced with Dulbecco's Modified Eagle's Medium (Gibco) containing 10% fetal bovine serum (Gibco) and 100 units/ml penicillin 100 µg/ml streptomycin, and 24 hours after media replacement, SRD5A2 expression was examined at the protein level. As the result of repeatedly conducting two experiments, it was confirmed that, as the treatment concentrations of cp-asiSRD5A2 #59(4,4) and #62(4,4) increased, the protein expression of the target gene SRD5A2 was reduced (see FIG. 9).

[Example 10] Screening for 118 Kinds of RNAi-Inducing Double-Stranded Nucleic Acid Molecules Targeting AR To obtain high-efficiency RNAi-inducing double-stranded nucleic acid molecules targeting AR, the target sequence of the AR gene was selected and then asiRNA was designed. The asiRNA structure is different from that of generally known siRNAs, and thus when the nucleotide sequences of asiRNA are designed using a general siRNA design program, it may be somewhat difficult to design an optimized asiRNA. Therefore, asiRNA was constructed by the following method. An NCBI db search was used to obtain information on the AR gene (mRNA Accession Number: NM_001011645.2), which is the target gene pertaining to male pattern hair loss (androgenetic hair loss). For subsequent animal experiments, nucleotide sequences with at least 80% homology to that of mice were secured, and then 100 asiRNAs were designed according to a design method such as the exclusion of sequences having a GC content of 30-62% and 4 or more G or C consecutive bases, and then synthesized by OliX Inc. (Korea). The synthesized sense and antisense strand RNA oligonucleotides were annealed at 95° C. for 2 minutes through incubation at 37° C. for 1 hour, and the asiRNA annealed by 10% polyacrylamide gel electrophoresis (PAGE) was confirmed using a UV transilluminator.

TABLE 6

118 strands of asiRNA nucleotide sequences targeting androgen receptor

| | | Sequence (5'-3') | |
|---|---|---|---|
| No. | Name | S (16mer) | As (21mer) |
| 1 | asiAR1 | GAGAUGAAGCUUCUGG (SEQ ID NO: 429) | CCAGAAGCUUCAUCUCCACAG (SEQ ID NO: 547) |

TABLE 6-continued 118 strands of asiRNA nucleotide sequences targeting androgen receptor

| No. | Name | Sequence (5'-3') S (16mer) | As (21mer) |
|---|---|---|---|
| 2 | asiAR2 | GGAGAUGAAGCUUCUG (SEQ ID NO: 430) | CAGAAGCUUCAUCUCCACAGA (SEQ ID NO: 548) |
| 3 | asiAR3 | GUGGAGAUGAAGCUUC (SEQ ID NO: 431) | GAAGCUUCAUCUCCACAGAUC (SEQ ID NO: 549) |
| 4 | asiAR4 | UGUGGAGAUGAAGCUU (SEQ ID NO: 432) | AAGCUUCAUCUCCACAGAUCA (SEQ ID NO: 550) |
| 5 | asiAR5 | UCUGUGGAGAUGAAGC (SEQ ID NO: 433) | GCUUCAUCUCCACAGAUCAGG (SEQ ID NO: 551) |
| 6 | asiAR6 | UGAUCUGUGGAGAUGA (SEQ ID NO: 434) | UCAUCUCCACAGAUCAGGCAG (SEQ ID NO: 552) |
| 7 | asiAR7 | CUGAUCUGUGGAGAUG (SEQ ID NO: 435) | CAUCUCCACAGAUCAGGCAGG (SEQ ID NO: 553) |
| 8 | asiAR8 | AAGACCUGCCUGAUCU (SEQ ID NO: 436) | AGAUCAGGCAGGUCUUCUGGG (SEQ ID NO: 554) |
| 9 | asiAR9 | UUUCCACCCCAGAAGA (SEQ ID NO: 437) | UCUUCUGGGGUGGAAAGUAAU (SEQ ID NO: 555) |
| 10 | asiAR10 | ACUUUCCACCCCAGAA (SEQ ID NO: 438) | UUCUGGGGUGGAAAGUAAUAG (SEQ ID NO: 556) |
| 11 | asiAR11 | AAGGGAAACAGAAGUA (SEQ ID NO: 439) | UACUUCUGUUUCCCUUCAGCG (SEQ ID NO: 557) |
| 12 | asiAR12 | GAAGGGAAACAGAAGU (SEQ ID NO: 440) | ACUUCUGUUUCCCUUCAGCGG (SEQ ID NO: 558) |
| 13 | asiAR13 | CUGAAGGGAAACAGAA (SEQ ID NO: 441) | UUCUGUUUCCCUUCAGCGGCU (SEQ ID NO: 559) |
| 14 | asiAR14 | CAAAAGAGCCGCUGAA (SEQ ID NO: 442) | UUCAGCGGCUCUUUUGAAGAA (SEQ ID NO: 560) |
| 15 | asiAR15 | UCAAAAGAGCCGCUGA (SEQ ID NO: 443) | UCAGCGGCUCUUUUGAAGAAG (SEQ ID NO: 561) |
| 16 | asiAR16 | CUUCAAAAGAGCCGCU (SEQ ID NO: 444) | AGCGGCUCUUUUGAAGAAGAC (SEQ ID NO: 562) |
| 17 | asiSR17 | CUUCUUCAAAAGAGCC (SEQ ID NO: 445) | GGCUCUUUUGAAGAAGACCUU (SEQ ID NO: 563) |
| 18 | asiAR18 | UCUUCUUCAAAAGAGC (SEQ ID NO: 446) | GCUCUUUUGAAGAAGACCUUG (SEQ ID NO: 564) |
| 19 | asiAR19 | AGGUCUUCUUCAAAAG (SEQ ID NO: 447) | CUUUUGAAGAAGACCUUGCAG (SEQ ID NO: 565) |
| 20 | asiAR20 | AACCAGGGAUGACUCU (SEQ ID NO: 448) | AGAGUCAUCCCUGCUUCAUAA (SEQ ID NO: 566) |
| 21 | asiAR21 | UGAAGCAGGGAUGACU (SEQ ID NO: 449) | AGUCAUCCCUGCUUCAUAACA (SEQ ID NO: 567) |
| 22 | asiAR22 | UUAUGAAGCAGGGAUG (SEQ ID NO: 450) | CAUCCCUGCUUCAUAACAUUU (SEQ ID NO: 568) |
| 23 | asiAR23 | UGUUAUGAAGCAGGGA (SEQ ID NO: 451) | UCCCUGCUUCAUAACAUUUCC (SEQ ID NO: 569) |
| 24 | asiAR24 | AUGUUAUGAAGCAGGG (SEQ ID NO: 452) | CCCUGCUUCAUAACAUUUCCG (SEQ ID NO: 570) |
| 25 | asiAR25 | GCUAUGAAUGUCAGCC (SEQ ID NO: 453) | GGCUGACAUUCAUAGCCUUCA (SEQ ID NO: 571) |
| 26 | asiAR26 | GGCUAUGAAUGUCAGC (SEQ ID NO: 454) | GCUGACAUUCAUAGCCUUCAA (SEQ ID NO: 572) |
| 27 | asiAR27 | GAAGGCUAUGAAUGUC (SEQ ID NO: 455) | GACAUUCAUAGCCUUCAAUGU (SEQ ID NO: 573) |
| 28 | asiAR28 | UUGAAGGCUAUGAAUG (SEQ ID NO: 456) | CAUUCAUAGCCUUCAAUGUGU (SEQ ID NO: 574) |
| 29 | asiAR29 | GAAGCCAUUGAGCCAG (SEQ ID NO: 457) | CUGGCUCAAUGGCUUCCAGGA (SEQ ID NO: 575) |
| 30 | asiAR30 | CUGGCUUCCGCAACUU (SEQ ID NO: 458) | AAGUUGCGGAAGCCAGGCAAG (SEQ ID NO: 576) |
| 31 | asiAR31 | UGCCUGGCUUCCGCAA (SEQ ID NO: 459) | UUGCGGAAGCCAGGCAAGGCC (SEQ ID NO: 577) |
| 32 | asiAR32 | AGUGGGCCAAGGCCUU (SEQ ID NO: 460) | AAGGCCUUGGCCCACUUGACC (SEQ ID NO: 578) |
| 33 | asiAR33 | CCAGGAUGCUCUACUU (SEQ ID NO: 481) | AAGUAGAGCAUCCUGGAGUUG (5E0 ID NO: 579) |
| 34 | asiAR34 | UCCAGGAUGCUCUACU (SEQ ID NO: 462) | AGUAGAGCAUCCUGGAGUUGA (SEQ ID NO: 580) |
| 35 | asiAR35 | AACUCCAGGAUGCUCU (SEQ ID NO: 463) | AGAGCAUCCUGGAGUUGACAU (SEQ ID NO: 581) |
| 36 | asiAR36 | UACCGCAUGCACAAGU (SEQ ID NO: 464) | ACUUGUGCAUGCGGUACUCAU (SEQ ID NO: 582) |
| 37 | asiAR37 | AGUACCGCAUGCACAA (SEQ ID NO: 465) | UUGUGCAUGCGGUACUCAUUG (SEQ ID NO: 583) |
| 38 | asiAR38 | CAAUGAGUACCGCAUG (SEQ ID NO: 466) | CAUGCGGUACUCAUUGAAAAC (SEQ ID NO: 594) |
| 39 | asiAR39 | UCAAUGAGUACCGCAU (SEQ ID NO: 467) | AUGCGGUACUCAUUGAAAACC (SEQ ID NO: 585) |
| 40 | asiAR40 | UUCAAUGAGUACCGCA (SEQ ID NO: 468) | UGCGGUACUCAUUGAAAACCA (SEQ ID NO: 586) |
| 41 | asiAR41 | UUGGAUGGCUCCAAAU (SEQ ID NO: 469) | AUUUGGAGCCAUCCAAACUCU (SEQ ID NO: 587) |
| 42 | asiAR42 | AGUUUGGAUGGCUCCA (SEQ ID NO: 470) | UGGAGCCAUCCAAACUCCUGA (SEQ ID NO: 588) |
| 43 | asiAR43 | AGAGUUUGGAUGGCUC (SEQ ID NO: 471) | GAGCCAUCCAAACUCUUGAGA (SEQ ID NO: 589) |
| 44 | asiAR44 | UCAAGGAACUCGAUCG (SEQ ID NO: 472) | CGAUCGAGUUCCUUGAUGUAG (SEQ ID NO: 590) |
| 45 | asiAR45 | CAUCAAGGAACUCGAU (SEQ ID NO: 473) | AUCGAGUUCCUUGAUGUAGUU (SEQ ID NO: 591) |
| 46 | asiAR46 | CUACAUCAAGGAACUC (SEQ ID NO: 474) | GAGUUCCUUGAUGUAGUUCAU (SEQ ID NO: 592) |
| 47 | asiAR47 | GAACUACAUCAAGGAA (SEQ ID NO: 475) | UUCCUUGAUGUAGUUCAUUCG (SEQ ID NO: 593) |
| 48 | asiAR48 | CUUCGAAUGAACUACA (SEQ ID NO: 476) | UGUAGUUCAUUCGAAGUUCAU (SEQ ID NO: 594) |
| 49 | asiAR49 | UGAACUUCGAAUGAAC (SEQ ID NO: 477) | GUUCAUUCGAAGUUCAUCAAA (SEQ ID NO: 595) |

TABLE 6-continued 118 strands of asiRNA nucleotide sequences targeting androgen receptor

| No. | Name | Sequence (5'-3') S (16mer) | As (21mer) |
|---|---|---|---|
| 50 | asiAR50 | UGAUGAACUUCGAAUG (SEQ ID NO: 478) | CAUUCGAAGUUCAUCAAAGAA (SEQ ID NO: 596) |
| 51 | asiAR51 | GGGCUGAAAAAUCAAA (SEQ ID NO: 479) | UUUGAUUUUCAGCCCAUCCA (SEQ ID NO: 597) |
| 52 | asiAR52 | GAUGGGCUGAAAAAUC (SEQ ID NO: 480) | GAUUUUUCAGCCCAUCCACUG (SEQ ID NO: 598) |
| 53 | asiAR53 | UAUUCCAGUGGAUGGG (SEQ ID NO: 481) | CCCAUCCACUGGAAUAAUGCU (SEQ ID NO: 599) |
| 54 | asiAR54 | CAUUAUUCCAGUGGAU (SEQ ID NO: 482) | AUCCACUGGAAUAAUGCUGAA (SEQ ID NO: 600) |
| 55 | asiAR55 | AGCAUUAUUCCAGUGG (SEQ ID NO: 483) | CCACUGGAAUAAUGCUGAAGA (SEQ ID NO: 601) |
| 56 | asiAR56 | UUCAGCAUUAUUCCAG (SEQ ID NO: 484) | CUGGAAUAAUGCUGAAGAGAG (SEQ ID NO: 602) |
| 57 | asiAR57 | CUCUUCAGCAUUAUUC (SEQ ID NO: 485) | GAAUAAUGCUGAAGAGAGCAG (SEQ ID NO: 603) |
| 58 | asiAR58 | CUGCUCUCUUCAGCAU (SEQ ID NO: 486) | AUGCUGAAGAGAGCAGUGCUU (SEQ ID NO: 604) |
| 59 | asiAR59 | AAGCACUGCUCUCUUC (SEQ ID NO: 487) | GAAGAGAGCAGUGCUUUCAUG (SEQ ID NO: 605) |
| 60 | asiAR60 | GAAAGCACUGCUCUCU (SEQ ID NO: 488) | AGAGAGCAGUGCUUUCAUGCA (SEQ ID NO: 606) |
| 61 | asiAR61 | CAUGAAAGCACUGCUC (SEQ ID NO: 489) | GAGCAGUGCUUUCAUGCACAG (SEQ ID NO: 607) |
| 62 | asiAR62 | GUGCAUGAAAGCACUG (SEQ ID NO: 490) | CAGUGCUUUCAUGCACAGGAA (SEQ ID NO: 608) |
| 63 | asiAR63 | UUCCUGUGCAUGAAAG (SEQ ID NO: 491) | CUUUCAUGCACAGGAAUUCCU (SEQ ID NO: 609) |
| 64 | asiAR64 | GAAUUCCUGUGCAUGA (SEQ ID NO: 492) | UCAUGCACAGGAAUUCCUGGG (SEQ ID NO: 610) |
| 65 | asiAR65 | AGGAAUUCCUGUGCAU (SEQ ID NO: 493) | AUGCACAGGAAUUCCUGGGGG (SEQ ID NO: 611) |
| 66 | asiAR66 | UCACCAAGCUCCUGGA (SEQ ID NO: 494) | UCCAGGAGCUUGGUGAGCUGG (SEQ ID NO: 612) |
| 67 | asiAR67 | ACCAGCUCACCAAGCU (SEQ ID NO: 495) | AGCUUGGUGAGCUGGUAGAAG (SEQ ID NO: 613) |
| 68 | asiAR68 | CUACCAGCUCACCAAG (SEQ ID NO: 496) | CUUGGUGAGCUGGUAGAAGCG (SEQ ID NO: 614) |
| 69 | asiAR69 | ACCUGCUAAUCAAGUC (SEQ ID NO: 497) | GACUUGAUUAGCAGGUCAAAA (SEQ ID NO: 615) |
| 70 | asiAR70 | GACCUGCUAAUCAAGU (SEQ ID NO: 498) | ACUUGAUUAGCAGGUCAAAAG (SEQ ID NO: 616) |
| 71 | asiAR71 | UUUGACCUGCUAAUCA (SEQ ID NO: 499) | UGAUUAGCAGGUCAAAAGUGA (SEQ ID NO: 617) |
| 72 | asiAR72 | CUUUUGACCUGCUAAU (SEQ ID NO: 500) | AUUAGCAGGUCAAAAGUGAAC (SEQ ID NO: 618) |
| 73 | asiAR73 | UCACUUUUGACCUGCU (SEQ ID NO: 501) | AGCAGGUCAAAAGUGAACUGA (SEQ ID NO: 619) |
| 74 | asiAR74 | UUCACUUUUGACCUGC (SEQ ID NO: 502) | GCAGGUCAAAAGUGAACUGAU (SEQ ID NO: 620) |
| 75 | asiAR75 | CAGUUCACUUUUGACC (SEQ ID NO: 503) | GGUCAAAAGUGAACUGAUGCA (SEQ ID NO: 621) |
| 76 | asiAR76 | CAUCAGUUCACUUUUG (SEQ ID NO: 504) | CAAAAGUGAACUGAUGCAGCU (SEQ ID NO: 622) |
| 77 | asiAR77 | CUGCAUCAGUUCACUU (SEQ ID NO: 505) | AAGUGAACUGAUGCAGCUCUC (SEQ ID NO: 623) |
| 78 | asiAR78 | GCUGCAUCAGUUCACU (SEQ ID NO: 506) | AGUGAACUGAUGCAGCUCUCU (SEQ ID NO: 624) |
| 79 | asiAR79 | CCAUCUAUUUCCACAC (SEQ ID NO: 507) | GUGUGGAAAUAGAUGGGCUUG (SEQ ID NO: 625) |
| 80 | asiAR80 | CCCAUCUAUUUCCACA (SEQ ID NO: 508) | UGUGGAAAUAGAUGGGCUUGA (SEQ ID NO: 626) |
| 81 | asiAR81 | AGCCCAUCUAUUUCCA (SEQ ID NO: 509) | UGGAAAUAGAUGGGCUUGACU (SEQ ID NO: 627) |
| 82 | asiAR82 | UCAAGCCCAUCUAUUU (SEQ ID NO: 510) | AAAUAGAUGGGCUUGACUUUC (SEQ ID NO: 628) |
| 83 | asiAR83 | GGAAAGUCAAGCCCAU (SEQ ID NO: 511) | AUGGGCUUGACUUUCCCAGAA (SEQ ID NO: 629) |
| 84 | asiAR84 | CUGGGAAAGUCAAGCC (SEQ ID NO: 512) | GGCUUGACUUUCCCAGAAAGG (SEQ ID NO: 630) |
| 85 | asiAR85 | UUUCUGGGAAAGUCAA (SEQ ID NO: 513) | UUGACUUUCCCAGAAAGGAUC (SEQ ID NO: 631) |
| 86 | asiAR86 | UCCUUUCUGGGAAAGU (SEQ ID NO: 514) | ACUUUCCCAGAAAGGAUCUUG (SEQ ID NO: 632) |
| 87 | asiAR87 | CCAAGAUCCUUUCUGG (SEQ ID NO: 515) | CCAGAAAGGAUCUUGGGCACU (SEQ ID NO: 633) |
| 88 | asiAR88 | UGCCCAAGAUCCUUUC (SEQ ID NO: 516) | GAAAGGAUCUUGGGCACUUGC (SEQ ID NO: 634) |
| 89 | asiAR89 | AAGUGCCCAAGAUCCU (SEQ ID NO: 517) | AGGAUCUUGGGCACUUGCACA (SEQ ID NO: 635) |
| 90 | asiAR90 | UGCAAGUGCCCAAGAU (SEQ ID NO: 518) | AUCUUGGGCACUUGCACAGAG (SEQ ID NO: 636) |
| 91 | asiAR91 | UCUCUGUGCAAGUGCC (SEQ ID NO: 519) | GGCACUUGCACAGAGAUGAUC (SEQ ID NO: 637) |
| 92 | asiAR92 | UCAUCUCUGUGCAAGU (SEQ ID NO: 520) | ACUUGCACAGAGAUGAUCUCU (SEQ ID NO: 636) |
| 93 | asiAR93 | AGAUCAUCUCUGUGCA (SEQ ID NO: 521) | UGCACAGAGAUGAUCUCUGCC (SEQ ID NO: 639) |
| 94 | asiAR94 | CAGAGAUCAUCUCUGU (SEQ ID NO: 522) | ACAGAGAUGAUCUCUGCCAUC (SEQ ID NO: 640) |
| 95 | asiAR95 | CACUGGCACUAAAAAA (SEQ ID NO: 523) | UUUUUUAGUGCCAGUGAACAU (SEQ ID NO: 641) |
| 96 | asiAR96 | UCACUGGCACUAAAAA (SEQ ID NO: 524) | UUUUUAGUGCCAGUGAACAUA (SEQ ID NO: 642) |
| 97 | asiAR97 | GUUCACUGGCACUAAA (SEQ ID NO: 525) | UUUAGUGCCAGUGAACAUACA (SEQ ID NO: 643) |

TABLE 6-continued 118 strands of asiRNA nucleotide sequences targeting androgen receptor

| No. | Name | S (16mer) Sequence (5'-3') | As (21mer) |
|---|---|---|---|
| 98 | asiAR98 | UAUGUUCACUGGCACU (SEQ ID NO: 526) | AGUGCCAGUGAACAUACAUAA (SEQ ID NO: 644) |
| 99 | asiAR99 | UGUAUGUUCACUGGCA (SEQ ID NO: 527) | UGCCAGUGAACAUACAUAAAA (SEQ ID NO: 645) |
| 100 | asiAR100 | UAUGUAUGUUCACUGG (SEQ ID NO: 528) | CCAGUGAACAUACAUAAAAAU (SEQ ID NO: 646) |
| 101 | asiAR101 | GGGUAGUUGCUGAGGU (SEQ ID NO: 529) | ACCUCAGCAACUACCCAAAGG (SEQ ID NO: 647) |
| 102 | asiAR102 | UGGGUAGUUGCUGAGG (SEQ ID NO: 530) | CCUCAGCAACUACCCAAAGGA (SEQ ID NO: 648) |
| 103 | asiAR103 | CUUUGGGUAGUUGCUG (SEQ ID NO: 531) | CAGCAACUACCCAAAGGACAG (SEQ ID NO: 649) |
| 104 | asiAR104 | CCUUUGGGUAGUUGCU (SEQ ID NO: 532) | AGCAACUACCCAAAGGACAGA (SEQ ID NO: 650) |
| 105 | asiAR105 | CCACCAUCCACAUGAU (SEQ ID NO: 533) | AUCAUGUGGAUGGUGGACAUA (SEQ ID NO: 651) |
| 106 | asiAR106 | CAUUAGUGCCUCUUUG (SEQ ID NO: 534) | CAAAGAGGCACUAAUGCUUGC (SEQ ID NO: 652) |
| 107 | asiAR107 | GCAUUAGUGCCUCUUU (SEQ ID NO: 535) | AAAGAGGCACUAAUGCUUGCU (SEQ ID NO: 653) |
| 108 | asiAR108 | AGCAUUAGUGCCUCUU (SEQ ID NO: 536) | AAGAGGCACUAAUGCUUGCUC (SEQ ID NO: 654) |
| 109 | asiAR109 | AAGCAUUAGUGCCUCU (SEQ ID NO: 537) | AGAGGCACUAAUGCUUGCUCC (SRI ID NO: 655) |
| 110 | asiAR110 | GCCCAUGUUAGCUUAU (SEQ ID NO: 538) | AUAAGCUAACAUGGGCACUAG (SEQ ID NO: 656) |
| 111 | asiAR111 | GAAACUUGUUUGUUGG (SEQ ID NO: 539) | CCAACAAACAAGUUUCUGCCA (SEQ ID NO: 657) |
| 112 | asiAR112 | GCAGAAACUUGUUUGU (SEQ ID NO: 540) | ACAAACAAGUUUCUGCCAUUU (SEQ ID NO: 658) |
| 113 | asiAR113 | AUGGCAGAAACUUGUU (SEQ ID NO: 541) | AACAAGUUUCUGCCAUUUUA (SEQ ID NO: 659) |
| 114 | asiAR114 | AAUGGCAGAAACUUGU (SEQ ID NO: 542) | ACAAGUUUCUGCCAUUUUAA (SEQ ID NO: 660) |
| 115 | asiAR115 | GGAAUCUUUUGUUGCU (SEQ ID NO: 543) | AGCAACAAAAGAUUCCAAGAU (SEQ ID NO: 661) |
| 116 | asiAR116 | UGGAAUCUUUUGUUGC (SEQ ID NO: 544) | GCAACAAAAGAUUCCAAGAUU (SEQ ID NO: 662) |
| 117 | asiAR117 | UAGUGUUCUGUUCUCU (SEQ ID NO: 545) | AGAGAACAGAACACUAGCGCU (SEQ ID NO: 663) |
| 118 | asiAR118 | CUAGUGUUCUGUUCUC (SEQ ID NO: 546) | GAGAACAGAACACUAGCGCUU (SEQ ID NO: 664) |

[Example 11] Screening for RNAi-Inducing Double-Stranded Nucleic Acid Molecules Targeting AR To confirm gene inhibitory efficiency at the mRNA level, the 118 selected asiRNAs were transfected into an A549 cell line at a concentration of 0.3 nM, and qRT-PCR was performed to measure the expression level of AR mRNA.

Figure 10A:
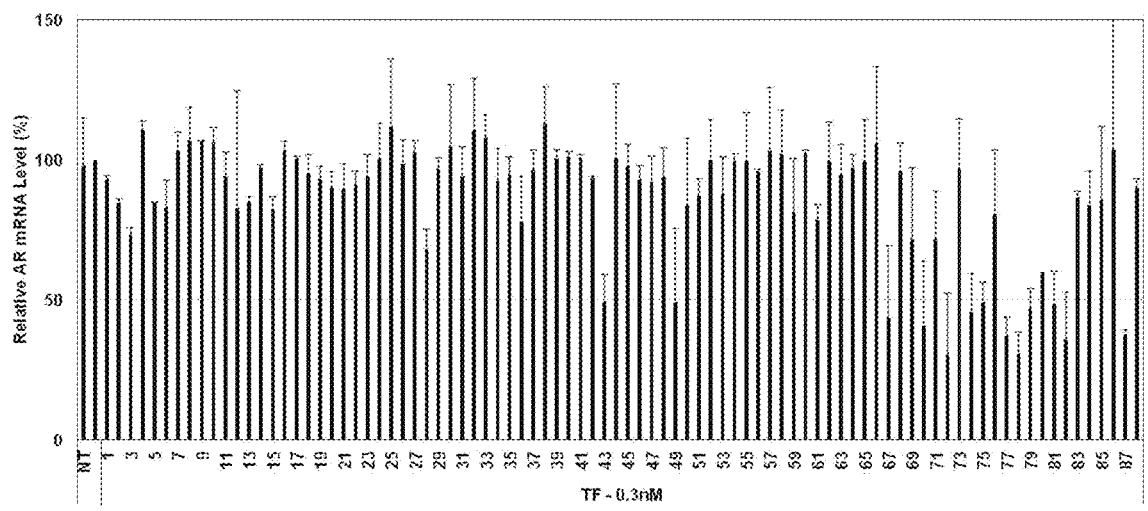
FIGS. 10A and 10B illustrate results showing the gene inhibitory efficiency of asiRNA against 118 sequences targeting AR. A549 cells were transfected with 0.3 nM of asiRNA targeting each nucleotide sequence, and after 24 hours, the expression level of AR mRNA was measured through qRT-PCR, the graphs showing the mean and SD of two repeated experiments.
Figure 10B:
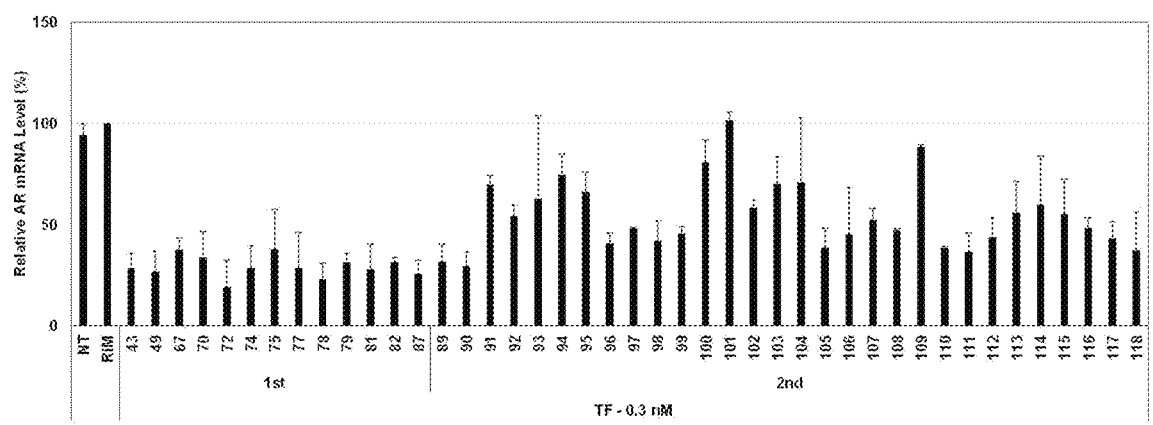

The A549 cell line was cultured in Dulbecco's Modified Eagle's Medium (DMEM, Gibco) containing 10% fetal bovine serum (FBS, Gibco) and 100 units/ml of penicillin 100 μg/ml of streptomycin. A549 cells were seeded in a 96-well plate at a density of $5 \times 10^3$ cells/well, and a transfection experiment was conducted using asiRNA (0.3 nM, OliX Pharmaceuticals Inc.) and RNAiMAX (1 μl/ml, Invitrogen Inc.) in Opti-MEM (a total volume of 100 μl) in accordance with Invitrogen's protocol. After 24 hours, RNA purification and cDNA synthesis were performed in accordance with a basic protocol provided by TOYOBO Super-Prep, the expression level of the AR gene was examined with an AR TaqMan probe (T) using a Bio-Rad CFX-4000 machine. First, 88 kinds of asiRNA from among the 118 kinds of asiRNA were subjected to an asiRNA screening experiment and the 13 top-ranked asiRNAs (in Table 6, No. 43, 49, 67, 70, 72, 74, 75, 77, 78, 79, 81, 82, and 87) were selected on the basis of inhibitory efficacy against the expression of the target gene, and the 13 selected asiRNAs and the 30 remaining asiRNAs (in Table 6, Nos. 88 to 118) were subjected to a secondary asiRNA screening experiment (see FIGS. 10A and 10B).

Figure 11:
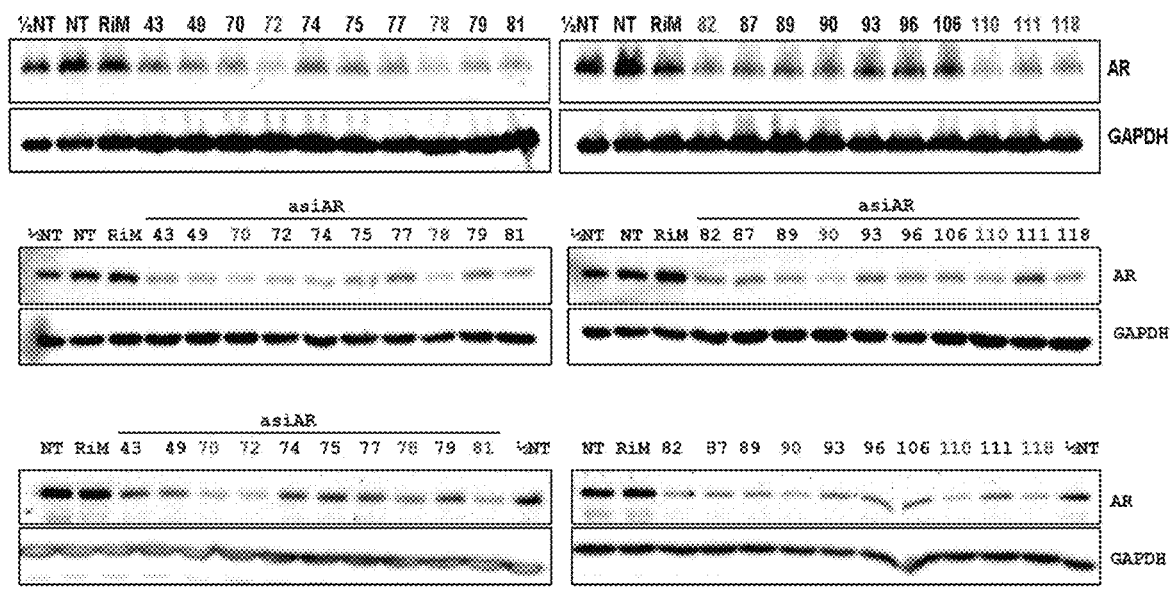
FIG. 11 illustrates results showing the inhibitory efficiency of asiRNA against 20 sequences targeting AR at a protein level. A549 cells were transfected with 0.3 nM asiRNA targeting each nucleotide sequence, and after 48 hours, the expression level of the AR protein was measured by western blotting, and experiments were repeated three times.

The 20 top-ranked asiRNAs (in Table 6, No. 43, 49, 70, 72, 74, 75, 77, 78, 79, 81, 82, 87, 89, 90, 93, 96, 106, 110, 111, and 118) having gone through secondary asiRNA screening were selected on the basis of inhibitory efficacy against the expression of the target gene, and an experiment for confirming the inhibitory effect of the 20 selected asiRNAs against AR expression at the protein level was performed. A549 cells were seeded in a 12-well plate at a density of $5 \times 10^4$ cells/well, and then a transfection experiment was conducted using asiRNA (0.3 nM, OliX Pharmaceuticals Inc.) and RNAiMAX (1 μl/ml, Invitrogen Inc.) in Opti-MEM (a total volume of 1 ml) in accordance with Invitrogen's protocol. After 48 hours, the cells were lysed using a mammalian protein extraction buffer (GE healthcare), and then proteins were quantified using a Bradford assay. 20 μg of the protein of each sample was electrophoresed using 10% SDS-PAGE at 80 V for 20 minutes and at 120 V for 1 hour, and then transferred onto a PVDE membrane (Bio-Rad) at 300 mA for 1 hour. After transfer, the membrane was blocked in 5% skim milk for 1 hour and allowed to react with AR antibody (ABcam, ab133273) at a ratio of 1:2000 for 12 hours. The next day, the resulting membrane was allowed to react with anti-Rabbit HRP (Santa Cruz) at a ratio of 1:5000 for 1 hour, and then the expression levels of the AR protein were compared with each other using ChemiDoc (Bio-Rad). From the results, the 9 top-ranked asiRNAs (No. 70, 72, 78, 81, 82, 90, 110, 111, and 118) capable of more effectively inhibiting AR protein expression were selected (see FIG. 11).

The 9 top-ranked asiRNA candidates (in Table 6, No. 70, 72, 78, 81, 82, 90, 110, 111, and 118) having gone through asiRNA screening were selected on the basis of inhibitory efficacy against the expression of the target gene, and an experiment for confirming the inhibitory effects of the 9 selected asiRNA candidates against AR expression at the mRNA and protein levels and a lower concentration (0.1 nM) was conducted. A549 cells were seeded in a 12-well plate at a density of $5 \times 10^4$ cells/well, and a transfection experiment was conducted using asiRNA and RNAiMAX (1 μl/ml, Invitrogen Inc.) in Opti-MEM (a total volume of 0.5 ml) in accordance with Invitrogen's protocol. After 48 hours, total RNA was extracted using TRIzol (TaKaPa), and then cDNA was synthesized using a high-capacity cDNA reverse transcription kit (Applied Biosystems), and the expression level of the AR gene was examined using power SYBR green PCR master Mix (Applied Biosystems), the primers shown in Table 7 below, and a StepOne real-time PCR system.

TABLE 7

Primer nucleotide sequences

| Name | | Sequence (5'-3') | size |
|---|---|---|---|
| Human GAPDH | Forward | GAG TCA ACG GAT TTG GTC GT (SEQ ID NO: 665) | 186 |
| | Reverse | GAC AAG CTT CCC GTT CTC AG (SEQ ID NO: 666) | |
| Human AR | Forward | GGG GCT AGA CTG CTC AAC TG (SEQ ID NO: 667) | 191 |
| | Reverse | GCC AAG TTT TGG CTG AAG AG (SEQ ID NO: 668) | |

Figure 12:
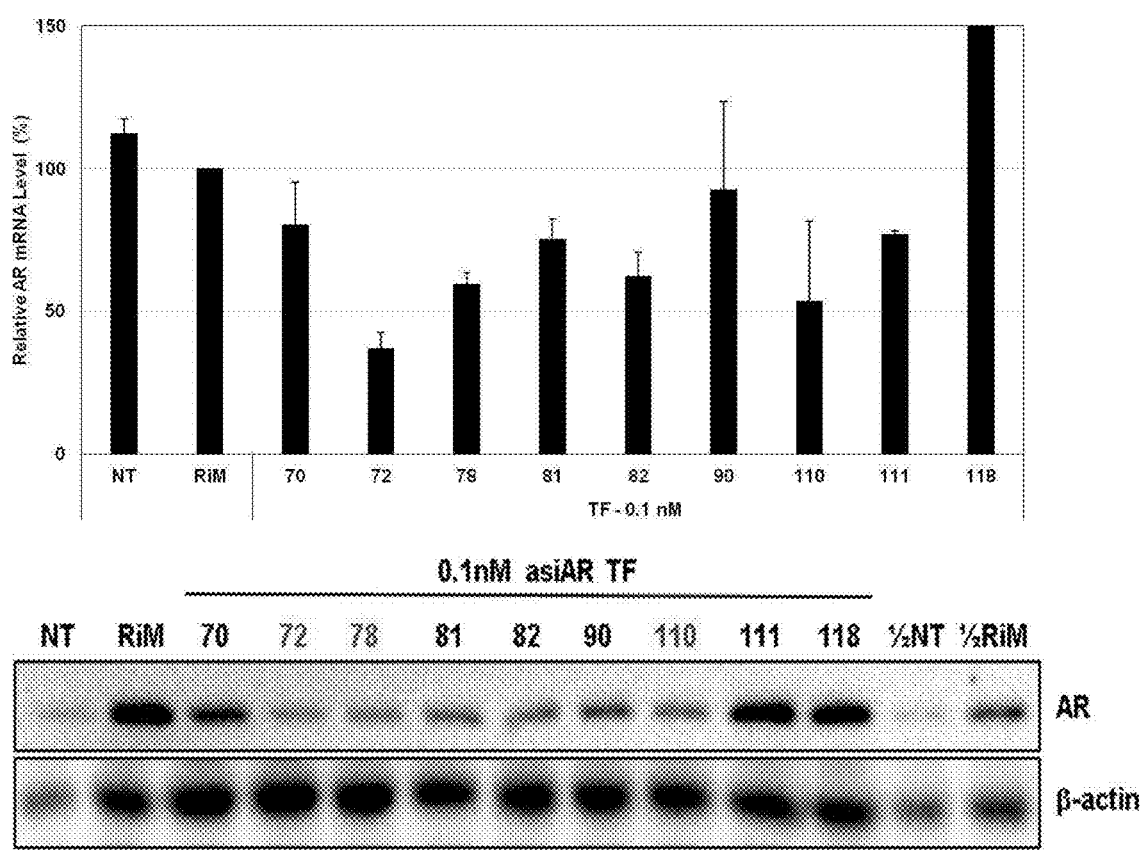
FIG. 12 illustrates results showing the gene inhibitory efficiency of asiRNA against 9 sequences targeting AR. A549 cells were transfected with 0.1 nM asiRNA targeting each nucleotide sequence, and after 48 hours, the expression levels of AR mRNA and the AR protein were measured by qRT-PCR and western blotting, respectively.

In addition, A549 cells were seeded in a 12-well plate at a density of 5×10⁴ cells/well, and a transfection experiment was conducted using asiRNA and RNAiMAX (1 µl/ml, Invitrogen Inc.) in Opti-MEM (a total volume of 0.5 ml) in accordance with Invitrogen's protocol. After 48 hours, the cells were lysed using a mammalian protein extraction buffer (GE healthcare), and then proteins were quantified using a Bradford assay. 20 µg of the protein of each sample was electrophoresed using 10% SDS-PAGE at 80 V for 20 minutes and at 120 V for 1 hour, and then transferred onto a PVDF membrane (Bio-Rad) at 300 mA for 1 hour. After transfer, the membrane was blocked in 5% skim milk for 1 hour and allowed to react with AR antibody (ABcam, ab133273) at a ratio of 1:2000 for 12 hours. The next day, the resulting membrane was allowed to react with anti-Rabbit HRP (Santa Cruz) at a ratio of 1:5000 for 1 hour, and then the expression levels of the AR protein were compared with each other using ChemiDoc (Bio-Rad). As the result of the experiment for the 9 selected asiRNAs, it was confirmed that asiRNA #72, 78, and 110 exhibited gene inhibitory efficiency of 50% or higher efficiently even at a concentration of 0.1 nM (see FIG. 12).

[Example 12] 9 Kinds of Cp-asiRNA Targeting AR Gene and Having Self Cell-Penetrating Ability AR cp-asiRNAs (a total of 9 kinds) were designed by applying three modification patterns to 3 kinds of asiRNA targeting AR according to the number and position of 2'OMe (methyl), phosphorothioate bonds (PS), and cholesterol, and then synthesized by Dharmacon. cp-asiRNA enhances endocytosis efficiency and stability, and thus may penetrate through the cell membrane with high efficiency without the aid of a delivery vehicle to thereby inhibit the expression of the target gene. The synthesized sense and antisense strand RNA oligonucleotides were annealed at 95° C. for 2 minutes through incubation at 37° C. for 1 hour, and cp-asiRNAs annealed by 10% polyacrylamide gel electrophoresis (PAGE) were confirmed using a UV transilluminator.

TABLE 8

9 kinds of cp-asiRNA nucleotide sequences targeting AR

| No. | Name | Sequence (5'-3') |
|---|---|---|
| 1 | cp-asiAR72 S | mCUmUUmUGmACmCUmGCmUAm*A*U*chol |
| 2 | cp-asiAR72 AS(7, 4) | AUUAGCAGGUCAAAmAmGmU*mG*mA*mA*mC |
| 3 | cp-asiAR72 AS(4, 4) | AUUAGCAGGUCAAAmAmGmU*mG*A*A*C |
| 4 | cp-asiAR72 AS(2, 4) | AUUAGCAGGUCAAAmAmGU*G*A*A*C |
| 5 | cp-asiAR78 S | mGCmUGmCAmUCmAGmUUmCAm*C*U*chol |
| 6 | cp-asiAR78 AS(7, 4) | AGUGAACUGAUGCAmGmCmU*mC*mU*mC*mU |
| 7 | cp-asiAR78 AS(4, 4) | AGUGAACUGAUGCAmGmCmU*mC*U*C*U |
| 8 | cp-asiAR78 AS(2, 4) | AGUGAACUGAUGCAmGmCU*C*U*C*U |
| 9 | cp-asiAR110 S | mGCmCCmAUmGUmUAmGCmUUm*A*U*chol |
| 10 | cp-asiAR110 AS(7, 4) | AUAAGCUAACAUGGmGmCmA*mC*mU*mA*mG |
| 11 | cp-asiAR110 AS(4, 4) | AUAAGCUAACAUGGmGmemA*mC*U*A*G |
| 12 | cp-asiAR110 AS(2, 4) | AUAAGCUAACAUGGmGmCA*C*U*A*G | m: 2'-O-Methyl RNA,
\*: phosphorothioated bond,
chol: cholesterol

Figure 13:
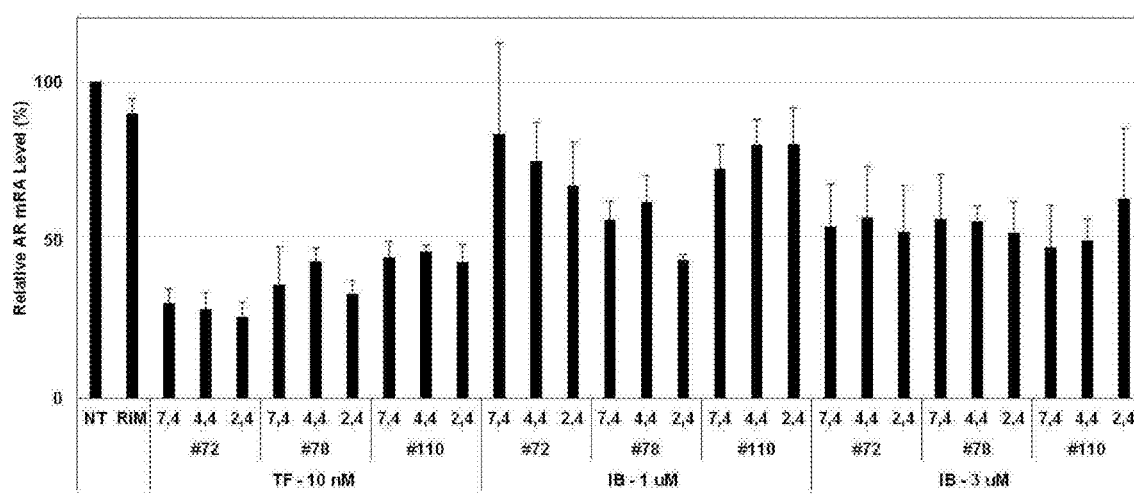
FIG. 13 illustrates results showing the gene inhibitory efficiency of 9 kinds of cp-asiRNA targeting an AR and having various chemical modifications added thereto. A549 cells were incubated with 1 μM or 3 μM of cp-asiRNA targeting each nucleotide sequence, and after 48 hours, the expression level of AR mRNA was measured through real-time PCR, and the graph shows the mean and SD of four repeated experiments.

[Example 13] Screening for Cp-asiRNA Targeting AR Gene and Having Self Cell-Penetrating Ability The inhibitory effects of the 9 kinds of cp-asiRNA shown in Table 8 against AR expression were examined. An A549 cell line was incubated with 1 µM or 3 µM of each of the 9 cp-asiRNAs in Opti-MEM media for 24 hours, and then the media were replaced with Dulbecco's Modified Eagle's Medium (Gibco) containing 10% fetal bovine serum (Gibco) and 100 units/ml penicillin 100 µg/ml streptomycin, and after 24 hours, AR expression was examined at the mRNA level. As the result of repeatedly conducting four experiments, it was confirmed that the 9 kinds of AR cp-asiRNA exhibited gene inhibitory efficiency of 50% at a concentration of 3 µM (see FIG. 13).

Figure 14:
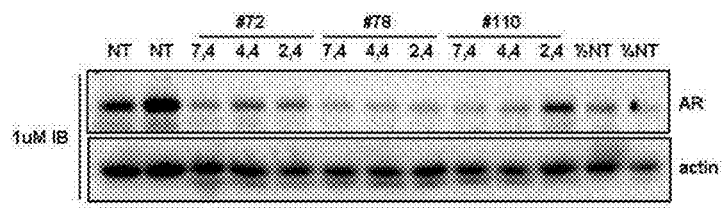
FIG. 14 illustrates results showing the gene inhibitory efficiency of 9 kinds of cp-asiRNA targeting an AR and having various chemical modifications added thereto. A549 cells were incubated with 1 μM of cp-asiRNA targeting each nucleotide sequence, and after 48 hours, the expression level of the AR protein was measured using a western blotting assay.

Under the same experimental conditions, the inhibitory effects of the 9 kinds of cp-asiRNA against AR expression were examined at the protein level in an A549 cell line. The A549 cell line was incubated with 1 µM or 3 µM of each of the 9 cp-asiRNAs in Opti-MEM media for 24 hours, and then the media were replaced with Dulbecco's Modified Eagle's Medium (Gibco) containing 10% fetal bovine serum (Gibco) and 100 units/ml penicillin 100 µg/ml streptomycin, and after 24 hours, AR expression was examined at the protein level. Among them, cp-asiRNA #72(7,4), #78(7,4) (4,4) (2,4), and #110(7,4) (4,4) exhibited target gene protein expression inhibitory efficiency of 50% or higher at a concentration of 1 μM on the basis of the band intensity of a no treatment (NT) sample and a ½ NT sample (see FIG. 14).

While the present invention has been described in detail with reference to specific embodiments thereof, it will be obvious to those of ordinary skill in the art that these embodiments are provided for illustrative purposes only and are not intended to limit the scope of the present invention. Therefore, the actual scope of the present invention will be defined by the appended claims and equivalents thereof.

INDUSTRIAL APPLICABILITY

A 5α-reductase type 1-encoding gene, a 5α-reductase type 2-encoding gene, and an androgen receptor-encoding gene, which play a major role in inhibiting the synthesis of proteins required for hair follicle growth in male pattern hair loss and inducing hair loss by reducing the size of the dermal papilla, were selected as target genes, and asymmetric siRNA with high inhibitory efficiency against each target gene was selected. siRNA according to the present invention exhibits the ability to inhibit the expression of the target gene for 5α-reductase type 1, 5α-reductase type 2, or an androgen receptor, and thus may be effectively used as an agent for preventing or treating hair loss.

While the present invention has been particularly shown and described with reference to specific embodiments thereof, it will be obvious to those of ordinary skill in the art that such embodiments are provided for illustrative purposes only and are not intended to limit the scope of the present invention. Therefore, the actual scope of the present invention should be defined by the appended claims and equivalents thereof.

SEQUENCE LIST FREE TEXT

Electronic files attached.

The invention claimed is:

1. The siRNA specifically binding to mRNA of an androgen receptor (AR)-encoding gene having SEQ ID NO: 673 and comprising a sense strand consisting of the sequence of SEQ ID NO: 500 and an antisense strand complementary to the sense strand and consisting of the sequence of SEQ ID NO: 618,
wherein a 3'-terminus of the sense strand and a 5'-terminus of the antisense strand form a blunt end.

2. The siRNA according to claim 1, wherein the sense strand or antisense strand of the siRNA comprises at least one chemical modification.

3. The siRNA according to claim 2, wherein the chemical modification comprises at least one selected from the group consisting of:
a modification in which an —OH group at a 2' carbon position of a sugar structure in a nucleotide is substituted with —CH₃ (methyl), —OCH₃ (methoxy), —NH₂, —F (fluorine), —O-2-methoxyethyl-O-propyl, —O-2-methylthioethyl, —O-3-aminopropyl, or —O-3-dimethylaminopropyl;
a modification in which oxygen in a sugar structure in a nucleotide is substituted with sulfur;
a modification of a nucleotide bond to a phosphorothioate, boranophosphate or methyl phosphonate;
a modification to peptide nucleic acid (PNA), locked nucleic acid (LNA), or unlocked nucleic acid (UNA); and
cholesterol or cell-penetrating peptide binding.

4. The siRNA according to claim 2, wherein the chemical modification is substitution of an —OH group at a 2' carbon position of a sugar structure in a nucleotide with —CH₃ (methyl), modification of a nucleotide bond to a phosphorothioate, or cholesterol binding.

5. The siRNA according to claim 4, wherein the chemical modification comprises at least one selected from the group consisting of:
a modification in which the —OH group at the 2' carbon position of a sugar structure in the 5'- or 3'-terminus nucleotide of the sense strand is substituted with —CH₃ (methyl);
a modification in which the —OH group at the 2' carbon position of a sugar structure in two or more nucleotides of the sense strand or the antisense strand is substituted with —CH₃ (methyl);
a modification of 25% or more of bonds between nucleotides in the sense or antisense strand to phosphorothioate; and
cholesterol binding at the 3'-terminus of the sense strand.

6. A composition for preventing or treating hair loss, the composition comprising the siRNA according to claim 1.

* * * * *

UNITED STATES PATENT AND TRADEMARK OFFICE
CERTIFICATE OF CORRECTION

PATENT NO. : 11,118,184 B2
APPLICATION NO. : 16/486833
DATED : September 14, 2021
INVENTOR(S) : Hong et al.

It is certified that error appears in the above-identified patent and that said Letters Patent is hereby corrected as shown below:

In the Specification

Column 16, Line 5, "$2.5 \times 10^3$ cells/well" should be -- $2.5 \times 10^5$ cells/well --.

Column 24, Line 6, "$2.5 \times 10^3$ cells/well" should be -- $2.5 \times 10^5$ cells/well --.

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*

```
                          SEQUENCE LISTING

<160> NUMBER OF SEQ ID NOS: 673

<210> SEQ ID NO 1
   <211> LENGTH: 16
   <212> TYPE: RNA
   <213> ORGANISM: Artificial Sequence
   <220> FEATURE:
   <223> OTHER INFORMATION: asiRNA

<400> SEQUENCE: 1
gcagauacuu gagcca                                                    16

<210> SEQ ID NO 2
   <211> LENGTH: 16
   <212> TYPE: RNA
   <213> ORGANISM: Artificial Sequence
   <220> FEATURE:
   <223> OTHER INFORMATION: asiRNA

<400> SEQUENCE: 2
aagcagauac uugagc                                                    16

<210> SEQ ID NO 3
   <211> LENGTH: 16
   <212> TYPE: RNA
   <213> ORGANISM: Artificial Sequence
   <220> FEATURE:
   <223> OTHER INFORMATION: asiRNA

<400> SEQUENCE: 3
caaagcagau acuuga                                                    16

<210> SEQ ID NO 4
   <211> LENGTH: 16
   <212> TYPE: RNA
   <213> ORGANISM: Artificial Sequence
   <220> FEATURE:
   <223> OTHER INFORMATION: asiRNA

<400> SEQUENCE: 4
ugcaaagcag auacuu                                                    16

<210> SEQ ID NO 5
   <211> LENGTH: 16
   <212> TYPE: RNA
   <213> ORGANISM: Artificial Sequence
```

```
<220> FEATURE:
<223> OTHER INFORMATION: asiRNA

<400> SEQUENCE: 5
gugcagugua ugcuga                                                       16

<210> SEQ ID NO 6
<211> LENGTH: 16
<212> TYPE: RNA
<213> ORGANISM: Artificial Sequence
<220> FEATURE:
<223> OTHER INFORMATION: asiRNA

<400> SEQUENCE: 6
uugugcagug uaugcu                                                       16

<210> SEQ ID NO 7
<211> LENGTH: 16
<212> TYPE: RNA
<213> ORGANISM: Artificial Sequence
<220> FEATURE:
<223> OTHER INFORMATION: asiRNA

<400> SEQUENCE: 7
cauugugcag uguaug                                                       16

<210> SEQ ID NO 8
<211> LENGTH: 16
<212> TYPE: RNA
<213> ORGANISM: Artificial Sequence
<220> FEATURE:
<223> OTHER INFORMATION: asiRNA

<400> SEQUENCE: 8
uuuuggcuug ugguua                                                       16

<210> SEQ ID NO 9
<211> LENGTH: 16
<212> TYPE: RNA
<213> ORGANISM: Artificial Sequence
<220> FEATURE:
<223> OTHER INFORMATION: asiRNA

<400> SEQUENCE: 9
cgggcauguu gauaaa                                                       16

<210> SEQ ID NO 10
<211> LENGTH: 16
<212> TYPE: RNA
<213> ORGANISM: Artificial Sequence
<220> FEATURE:
<223> OTHER INFORMATION: asiRNA

<400> SEQUENCE: 10
auauccuaag gaaucu                                                       16

<210> SEQ ID NO 11
<211> LENGTH: 16
<212> TYPE: RNA
<213> ORGANISM: Artificial Sequence
<220> FEATURE:
<223> OTHER INFORMATION: asiRNA

<400> SEQUENCE: 11
aucucagaaa accagg                                                       16
```

```
<210> SEQ ID NO 12
<211> LENGTH: 16
<212> TYPE: RNA
<213> ORGANISM: Artificial Sequence
<220> FEATURE:
<223> OTHER INFORMATION: asiRNA

<400> SEQUENCE: 12
gaaucucaga aaacca                                                   16

<210> SEQ ID NO 13
<211> LENGTH: 16
<212> TYPE: RNA
<213> ORGANISM: Artificial Sequence
<220> FEATURE:
<223> OTHER INFORMATION: asiRNA

<400> SEQUENCE: 13
aggaaucuca gaaaac                                                   16

<210> SEQ ID NO 14
<211> LENGTH: 16
<212> TYPE: RNA
<213> ORGANISM: Artificial Sequence
<220> FEATURE:
<223> OTHER INFORMATION: asiRNA

<400> SEQUENCE: 14
cuggauacaa aauacc                                                   16

<210> SEQ ID NO 15
<211> LENGTH: 16
<212> TYPE: RNA
<213> ORGANISM: Artificial Sequence
<220> FEATURE:
<223> OTHER INFORMATION: asiRNA

<400> SEQUENCE: 15
uacuggauac aaaaua                                                   16

<210> SEQ ID NO 16
<211> LENGTH: 16
<212> TYPE: RNA
<213> ORGANISM: Artificial Sequence
<220> FEATURE:
<223> OTHER INFORMATION: asiRNA

<400> SEQUENCE: 16
gauacuggau acaaaa                                                   16

<210> SEQ ID NO 17
<211> LENGTH: 16
<212> TYPE: RNA
<213> ORGANISM: Artificial Sequence
<220> FEATURE:
<223> OTHER INFORMATION: asiRNA

<400> SEQUENCE: 17
gagauacugg auacaa                                                   16

<210> SEQ ID NO 18
<211> LENGTH: 16
<212> TYPE: RNA
<213> ORGANISM: Artificial Sequence
<220> FEATURE:
<223> OTHER INFORMATION: asiRNA
```

-continued

```
<400> SEQUENCE: 18
aggagauacu ggauac                                                   16

<210> SEQ ID NO 19
<211> LENGTH: 16
<212> TYPE: RNA
<213> ORGANISM: Artificial Sequence
<220> FEATURE:
<223> OTHER INFORMATION: asiRNA

<400> SEQUENCE: 19
ccaggagaua cuggau                                                   16

<210> SEQ ID NO 20
<211> LENGTH: 16
<212> TYPE: RNA
<213> ORGANISM: Artificial Sequence
<220> FEATURE:
<223> OTHER INFORMATION: asiRNA

<400> SEQUENCE: 20
aauaccaagg ggaggc                                                   16

<210> SEQ ID NO 21
<211> LENGTH: 16
<212> TYPE: RNA
<213> ORGANISM: Artificial Sequence
<220> FEATURE:
<223> OTHER INFORMATION: asiRNA

<400> SEQUENCE: 21
aaaauaccaa ggggag                                                   16

<210> SEQ ID NO 22
<211> LENGTH: 16
<212> TYPE: RNA
<213> ORGANISM: Artificial Sequence
<220> FEATURE:
<223> OTHER INFORMATION: asiRNA

<400> SEQUENCE: 22
gaggcuuauu ugaaua                                                   16

<210> SEQ ID NO 23
<211> LENGTH: 16
<212> TYPE: RNA
<213> ORGANISM: Artificial Sequence
<220> FEATURE:
<223> OTHER INFORMATION: asiRNA

<400> SEQUENCE: 23
cagccaacua uuuugg                                                   16

<210> SEQ ID NO 24
<211> LENGTH: 16
<212> TYPE: RNA
<213> ORGANISM: Artificial Sequence
<220> FEATURE:
<223> OTHER INFORMATION: asiRNA

<400> SEQUENCE: 24
ugcagccaac uauuuu                                                   16

<210> SEQ ID NO 25
```

```
<211> LENGTH: 16
<212> TYPE: RNA
<213> ORGANISM: Artificial Sequence
<220> FEATURE:
<223> OTHER INFORMATION: asiRNA

<400> SEQUENCE: 25
acugcagcca acuauu                                                       16

<210> SEQ ID NO 26
<211> LENGTH: 16
<212> TYPE: RNA
<213> ORGANISM: Artificial Sequence
<220> FEATURE:
<223> OTHER INFORMATION: asiRNA

<400> SEQUENCE: 26
uaacugcagc caacua                                                       16

<210> SEQ ID NO 27
<211> LENGTH: 16
<212> TYPE: RNA
<213> ORGANISM: Artificial Sequence
<220> FEATURE:
<223> OTHER INFORMATION: asiRNA

<400> SEQUENCE: 27
cguaacugca gccaac                                                       16

<210> SEQ ID NO 28
<211> LENGTH: 16
<212> TYPE: RNA
<213> ORGANISM: Artificial Sequence
<220> FEATURE:
<223> OTHER INFORMATION: asiRNA

<400> SEQUENCE: 28
auggaguggu guggcu                                                       16

<210> SEQ ID NO 29
<211> LENGTH: 16
<212> TYPE: RNA
<213> ORGANISM: Artificial Sequence
<220> FEATURE:
<223> OTHER INFORMATION: asiRNA

<400> SEQUENCE: 29
ucauggagug gugugg                                                       16

<210> SEQ ID NO 30
<211> LENGTH: 16
<212> TYPE: RNA
<213> ORGANISM: Artificial Sequence
<220> FEATURE:
<223> OTHER INFORMATION: asiRNA

<400> SEQUENCE: 30
aaucauggag uggugu                                                       16

<210> SEQ ID NO 31
<211> LENGTH: 16
<212> TYPE: RNA
<213> ORGANISM: Artificial Sequence
<220> FEATURE:
<223> OTHER INFORMATION: asiRNA

<400> SEQUENCE: 31
```
gaaaucaugg aguggu                                                    16

<210> SEQ ID NO 32
<211> LENGTH: 16
<212> TYPE: RNA
<213> ORGANISM: Artificial Sequence
<220> FEATURE:
<223> OTHER INFORMATION: asiRNA

<400> SEQUENCE: 32
gagaaaucau ggagug                                                    16

<210> SEQ ID NO 33
<211> LENGTH: 16
<212> TYPE: RNA
<213> ORGANISM: Artificial Sequence
<220> FEATURE:
<223> OTHER INFORMATION: asiRNA

<400> SEQUENCE: 33
cccuggccag cugguc                                                    16

<210> SEQ ID NO 34
<211> LENGTH: 16
<212> TYPE: RNA
<213> ORGANISM: Artificial Sequence
<220> FEATURE:
<223> OTHER INFORMATION: asiRNA

<400> SEQUENCE: 34
uaugcccugg ccagcu                                                    16

<210> SEQ ID NO 35
<211> LENGTH: 16
<212> TYPE: RNA
<213> ORGANISM: Artificial Sequence
<220> FEATURE:
<223> OTHER INFORMATION: asiRNA

<400> SEQUENCE: 35
gcuaugcccu ggccag                                                    16

<210> SEQ ID NO 36
<211> LENGTH: 16
<212> TYPE: RNA
<213> ORGANISM: Artificial Sequence
<220> FEATURE:
<223> OTHER INFORMATION: asiRNA

<400> SEQUENCE: 36
ucaugagugg uaccuc                                                    16

<210> SEQ ID NO 37
<211> LENGTH: 16
<212> TYPE: RNA
<213> ORGANISM: Artificial Sequence
<220> FEATURE:
<223> OTHER INFORMATION: asiRNA

<400> SEQUENCE: 37
caucaugagu gguacc                                                    16

<210> SEQ ID NO 38
<211> LENGTH: 16
<212> TYPE: RNA

```
<213> ORGANISM: Artificial Sequence
<220> FEATURE:
<223> OTHER INFORMATION: asiRNA

<400> SEQUENCE: 38
uccggaaauu ugaaga                                                        16

<210> SEQ ID NO 39
<211> LENGTH: 16
<212> TYPE: RNA
<213> ORGANISM: Artificial Sequence
<220> FEATURE:
<223> OTHER INFORMATION: asiRNA

<400> SEQUENCE: 39
caguguaugc ugauga                                                        16

<210> SEQ ID NO 40
<211> LENGTH: 16
<212> TYPE: RNA
<213> ORGANISM: Artificial Sequence
<220> FEATURE:
<223> OTHER INFORMATION: asiRNA

<400> SEQUENCE: 40
gcauguugau aaacau                                                        16

<210> SEQ ID NO 41
<211> LENGTH: 16
<212> TYPE: RNA
<213> ORGANISM: Artificial Sequence
<220> FEATURE:
<223> OTHER INFORMATION: asiRNA

<400> SEQUENCE: 41
guggcuaugc ccuggc                                                        16

<210> SEQ ID NO 42
<211> LENGTH: 16
<212> TYPE: RNA
<213> ORGANISM: Artificial Sequence
<220> FEATURE:
<223> OTHER INFORMATION: asiRNA

<400> SEQUENCE: 42
guguggcuau gcccug                                                        16

<210> SEQ ID NO 43
<211> LENGTH: 16
<212> TYPE: RNA
<213> ORGANISM: Artificial Sequence
<220> FEATURE:
<223> OTHER INFORMATION: asiRNA

<400> SEQUENCE: 43
ugguguggcu augccc                                                        16

<210> SEQ ID NO 44
<211> LENGTH: 16
<212> TYPE: RNA
<213> ORGANISM: Artificial Sequence
<220> FEATURE:
<223> OTHER INFORMATION: asiRNA

<400> SEQUENCE: 44
aguggugugg cuaugc                                                        16
```

```
<210> SEQ ID NO 45
<211> LENGTH: 16
<212> TYPE: RNA
<213> ORGANISM: Artificial Sequence
<220> FEATURE:
<223> OTHER INFORMATION: asiRNA

<400> SEQUENCE: 45
ucuucacguu uuguuu                                                      16

<210> SEQ ID NO 46
<211> LENGTH: 16
<212> TYPE: RNA
<213> ORGANISM: Artificial Sequence
<220> FEATURE:
<223> OTHER INFORMATION: asiRNA

<400> SEQUENCE: 46
gacuugagaa cccuuu                                                      16

<210> SEQ ID NO 47
<211> LENGTH: 16
<212> TYPE: RNA
<213> ORGANISM: Artificial Sequence
<220> FEATURE:
<223> OTHER INFORMATION: asiRNA

<400> SEQUENCE: 47
cuguuggcgu guacaa                                                      16

<210> SEQ ID NO 48
<211> LENGTH: 16
<212> TYPE: RNA
<213> ORGANISM: Artificial Sequence
<220> FEATURE:
<223> OTHER INFORMATION: asiRNA

<400> SEQUENCE: 48
uuauuugaau acguaa                                                      16

<210> SEQ ID NO 49
<211> LENGTH: 16
<212> TYPE: RNA
<213> ORGANISM: Artificial Sequence
<220> FEATURE:
<223> OTHER INFORMATION: asiRNA

<400> SEQUENCE: 49
uuccaauggc gcuucu                                                      16

<210> SEQ ID NO 50
<211> LENGTH: 16
<212> TYPE: RNA
<213> ORGANISM: Artificial Sequence
<220> FEATURE:
<223> OTHER INFORMATION: asiRNA

<400> SEQUENCE: 50
aaaggcaucu ggacuu                                                      16

<210> SEQ ID NO 51
<211> LENGTH: 16
<212> TYPE: RNA
<213> ORGANISM: Artificial Sequence
<220> FEATURE:
```

<223> OTHER INFORMATION: asiRNA

<400> SEQUENCE: 51
aucaaugugc ucuggu                                                        16

<210> SEQ ID NO 52
<211> LENGTH: 16
<212> TYPE: RNA
<213> ORGANISM: Artificial Sequence
<220> FEATURE:
<223> OTHER INFORMATION: asiRNA

<400> SEQUENCE: 52
gaucacuuuc uguaac                                                        16

<210> SEQ ID NO 53
<211> LENGTH: 16
<212> TYPE: RNA
<213> ORGANISM: Artificial Sequence
<220> FEATURE:
<223> OTHER INFORMATION: asiRNA

<400> SEQUENCE: 53
aucuuccuuc uaauag                                                        16

<210> SEQ ID NO 54
<211> LENGTH: 16
<212> TYPE: RNA
<213> ORGANISM: Artificial Sequence
<220> FEATURE:
<223> OTHER INFORMATION: asiRNA

<400> SEQUENCE: 54
ggcauugcuu ugccuu                                                        16

<210> SEQ ID NO 55
<211> LENGTH: 16
<212> TYPE: RNA
<213> ORGANISM: Artificial Sequence
<220> FEATURE:
<223> OTHER INFORMATION: asiRNA

<400> SEQUENCE: 55
uguacaaugg cgauua                                                        16

<210> SEQ ID NO 56
<211> LENGTH: 16
<212> TYPE: RNA
<213> ORGANISM: Artificial Sequence
<220> FEATURE:
<223> OTHER INFORMATION: asiRNA

<400> SEQUENCE: 56
cuucucuaug gacuuu                                                        16

<210> SEQ ID NO 57
<211> LENGTH: 16
<212> TYPE: RNA
<213> ORGANISM: Artificial Sequence
<220> FEATURE:
<223> OTHER INFORMATION: asiRNA

<400> SEQUENCE: 57
uuccaaggug aggcaa                                                        16

```
<210> SEQ ID NO 58
<211> LENGTH: 16
<212> TYPE: RNA
<213> ORGANISM: Artificial Sequence
<220> FEATURE:
<223> OTHER INFORMATION: asiRNA

<400> SEQUENCE: 58
uccaagguga ggcaaa                                                    16

<210> SEQ ID NO 59
<211> LENGTH: 16
<212> TYPE: RNA
<213> ORGANISM: Artificial Sequence
<220> FEATURE:
<223> OTHER INFORMATION: asiRNA

<400> SEQUENCE: 59
gguucauacg gaguaa                                                    16

<210> SEQ ID NO 60
<211> LENGTH: 16
<212> TYPE: RNA
<213> ORGANISM: Artificial Sequence
<220> FEATURE:
<223> OTHER INFORMATION: asiRNA

<400> SEQUENCE: 60
auaguagaga uuguug                                                    16

<210> SEQ ID NO 61
<211> LENGTH: 16
<212> TYPE: RNA
<213> ORGANISM: Artificial Sequence
<220> FEATURE:
<223> OTHER INFORMATION: asiRNA

<400> SEQUENCE: 61
uguugucugu gaaauu                                                    16

<210> SEQ ID NO 62
<211> LENGTH: 16
<212> TYPE: RNA
<213> ORGANISM: Artificial Sequence
<220> FEATURE:
<223> OTHER INFORMATION: asiRNA

<400> SEQUENCE: 62
uucaagcucu ggguaa                                                    16

<210> SEQ ID NO 63
<211> LENGTH: 16
<212> TYPE: RNA
<213> ORGANISM: Artificial Sequence
<220> FEATURE:
<223> OTHER INFORMATION: asiRNA

<400> SEQUENCE: 63
uaccuaauaa guaccu                                                    16

<210> SEQ ID NO 64
<211> LENGTH: 16
<212> TYPE: RNA
<213> ORGANISM: Artificial Sequence
<220> FEATURE:
<223> OTHER INFORMATION: asiRNA
```

```
<400> SEQUENCE: 64
auuguugucu gugaaa                                              16

<210> SEQ ID NO 65
<211> LENGTH: 16
<212> TYPE: RNA
<213> ORGANISM: Artificial Sequence
<220> FEATURE:
<223> OTHER INFORMATION: asiRNA

<400> SEQUENCE: 65
caaaagagca ucauga                                              16

<210> SEQ ID NO 66
<211> LENGTH: 16
<212> TYPE: RNA
<213> ORGANISM: Artificial Sequence
<220> FEATURE:
<223> OTHER INFORMATION: asiRNA

<400> SEQUENCE: 66
cuauggacuu uguaaa                                              16

<210> SEQ ID NO 67
<211> LENGTH: 16
<212> TYPE: RNA
<213> ORGANISM: Artificial Sequence
<220> FEATURE:
<223> OTHER INFORMATION: asiRNA

<400> SEQUENCE: 67
cugucuuuga uggcau                                              16

<210> SEQ ID NO 68
<211> LENGTH: 16
<212> TYPE: RNA
<213> ORGANISM: Artificial Sequence
<220> FEATURE:
<223> OTHER INFORMATION: asiRNA

<400> SEQUENCE: 68
ucuaccuaau aaguac                                              16

<210> SEQ ID NO 69
<211> LENGTH: 16
<212> TYPE: RNA
<213> ORGANISM: Artificial Sequence
<220> FEATURE:
<223> OTHER INFORMATION: asiRNA

<400> SEQUENCE: 69
cuaaucuucc uucuaa                                              16

<210> SEQ ID NO 70
<211> LENGTH: 16
<212> TYPE: RNA
<213> ORGANISM: Artificial Sequence
<220> FEATURE:
<223> OTHER INFORMATION: asiRNA

<400> SEQUENCE: 70
cauuuucaga acaaua                                              16

<210> SEQ ID NO 71
<211> LENGTH: 16
```

```
<212> TYPE: RNA
<213> ORGANISM: Artificial Sequence
<220> FEATURE:
<223> OTHER INFORMATION: asiRNA

<400> SEQUENCE: 71
gaucucuuca agguca                                                         16

<210> SEQ ID NO 72
<211> LENGTH: 16
<212> TYPE: RNA
<213> ORGANISM: Artificial Sequence
<220> FEATURE:
<223> OTHER INFORMATION: asiRNA

<400> SEQUENCE: 72
agauuguugu cuguga                                                         16

<210> SEQ ID NO 73
<211> LENGTH: 16
<212> TYPE: RNA
<213> ORGANISM: Artificial Sequence
<220> FEATURE:
<223> OTHER INFORMATION: asiRNA

<400> SEQUENCE: 73
agagauuguu gucugu                                                         16

<210> SEQ ID NO 74
<211> LENGTH: 16
<212> TYPE: RNA
<213> ORGANISM: Artificial Sequence
<220> FEATURE:
<223> OTHER INFORMATION: asiRNA

<400> SEQUENCE: 74
agacgaacuc agugua                                                         16

<210> SEQ ID NO 75
<211> LENGTH: 16
<212> TYPE: RNA
<213> ORGANISM: Artificial Sequence
<220> FEATURE:
<223> OTHER INFORMATION: asiRNA

<400> SEQUENCE: 75
uccuccuggc cauguu                                                         16

<210> SEQ ID NO 76
<211> LENGTH: 16
<212> TYPE: RNA
<213> ORGANISM: Artificial Sequence
<220> FEATURE:
<223> OTHER INFORMATION: asiRNA

<400> SEQUENCE: 76
cuuaauuuac ccauuu                                                         16

<210> SEQ ID NO 77
<211> LENGTH: 16
<212> TYPE: RNA
<213> ORGANISM: Artificial Sequence
<220> FEATURE:
<223> OTHER INFORMATION: asiRNA

<400> SEQUENCE: 77
```
ugaugcgagg aggaaa                                                    16

<210> SEQ ID NO 78
<211> LENGTH: 16
<212> TYPE: RNA
<213> ORGANISM: Artificial Sequence
<220> FEATURE:
<223> OTHER INFORMATION: asiRNA

<400> SEQUENCE: 78
uguucuguac cuguaa                                                    16

<210> SEQ ID NO 79
<211> LENGTH: 16
<212> TYPE: RNA
<213> ORGANISM: Artificial Sequence
<220> FEATURE:
<223> OTHER INFORMATION: asiRNA

<400> SEQUENCE: 79
ccuguaacgg cuauuu                                                    16

<210> SEQ ID NO 80
<211> LENGTH: 16
<212> TYPE: RNA
<213> ORGANISM: Artificial Sequence
<220> FEATURE:
<223> OTHER INFORMATION: asiRNA

<400> SEQUENCE: 80
ccauugugca guguau                                                    16

<210> SEQ ID NO 81
<211> LENGTH: 16
<212> TYPE: RNA
<213> ORGANISM: Artificial Sequence
<220> FEATURE:
<223> OTHER INFORMATION: asiRNA

<400> SEQUENCE: 81
aacauccauu cagauc                                                    16

<210> SEQ ID NO 82
<211> LENGTH: 16
<212> TYPE: RNA
<213> ORGANISM: Artificial Sequence
<220> FEATURE:
<223> OTHER INFORMATION: asiRNA

<400> SEQUENCE: 82
uauccaaagu ucagaa                                                    16

<210> SEQ ID NO 83
<211> LENGTH: 16
<212> TYPE: RNA
<213> ORGANISM: Artificial Sequence
<220> FEATURE:
<223> OTHER INFORMATION: asiRNA

<400> SEQUENCE: 83
accuaaauac gcugaa                                                    16

<210> SEQ ID NO 84
<211> LENGTH: 16
<212> TYPE: RNA
<213> ORGANISM: Artificial Sequence

```
<220> FEATURE:
<223> OTHER INFORMATION: asiRNA

<400> SEQUENCE: 84
cgcugaaaug gagguu                                                        16

<210> SEQ ID NO 85
<211> LENGTH: 16
<212> TYPE: RNA
<213> ORGANISM: Artificial Sequence
<220> FEATURE:
<223> OTHER INFORMATION: asiRNA

<400> SEQUENCE: 85
aauggagguu gaauau                                                        16

<210> SEQ ID NO 86
<211> LENGTH: 16
<212> TYPE: RNA
<213> ORGANISM: Artificial Sequence
<220> FEATURE:
<223> OTHER INFORMATION: asiRNA

<400> SEQUENCE: 86
auauccuacu guguaa                                                        16

<210> SEQ ID NO 87
<211> LENGTH: 16
<212> TYPE: RNA
<213> ORGANISM: Artificial Sequence
<220> FEATURE:
<223> OTHER INFORMATION: asiRNA

<400> SEQUENCE: 87
uaugagacua gacuuu                                                        16

<210> SEQ ID NO 88
<211> LENGTH: 16
<212> TYPE: RNA
<213> ORGANISM: Artificial Sequence
<220> FEATURE:
<223> OTHER INFORMATION: asiRNA

<400> SEQUENCE: 88 aaugcacaa ucccuu                                                         16

<210> SEQ ID NO 89
<211> LENGTH: 16
<212> TYPE: RNA
<213> ORGANISM: Artificial Sequence
<220> FEATURE:
<223> OTHER INFORMATION: asiRNA

<400> SEQUENCE: 89
ggucaacugc aguguu                                                        16

<210> SEQ ID NO 90
<211> LENGTH: 16
<212> TYPE: RNA
<213> ORGANISM: Artificial Sequence
<220> FEATURE:
<223> OTHER INFORMATION: asiRNA

<400> SEQUENCE: 90
gccauugugc agucau                                                        16
```

<210> SEQ ID NO 91
<211> LENGTH: 16
<212> TYPE: RNA
<213> ORGANISM: Artificial Sequence
<220> FEATURE:
<223> OTHER INFORMATION: asiRNA

<400> SEQUENCE: 91
uguaagugga gaacuu                                                          16

<210> SEQ ID NO 92
<211> LENGTH: 16
<212> TYPE: RNA
<213> ORGANISM: Artificial Sequence
<220> FEATURE:
<223> OTHER INFORMATION: asiRNA

<400> SEQUENCE: 92
cucugccugu gugagu                                                          16

<210> SEQ ID NO 93
<211> LENGTH: 16
<212> TYPE: RNA
<213> ORGANISM: Artificial Sequence
<220> FEATURE:
<223> OTHER INFORMATION: asiRNA

<400> SEQUENCE: 93
accgugagcc aucaau                                                          16

<210> SEQ ID NO 94
<211> LENGTH: 16
<212> TYPE: RNA
<213> ORGANISM: Artificial Sequence
<220> FEATURE:
<223> OTHER INFORMATION: asiRNA

<400> SEQUENCE: 94
gguuucucuc ugucuu                                                          16

<210> SEQ ID NO 95
<211> LENGTH: 16
<212> TYPE: RNA
<213> ORGANISM: Artificial Sequence
<220> FEATURE:
<223> OTHER INFORMATION: asiRNA

<400> SEQUENCE: 95
uagucuagac cuaguu                                                          16

<210> SEQ ID NO 96
<211> LENGTH: 16
<212> TYPE: RNA
<213> ORGANISM: Artificial Sequence
<220> FEATURE:
<223> OTHER INFORMATION: asiRNA

<400> SEQUENCE: 96
uaguguaaag aaugau                                                          16

<210> SEQ ID NO 97
<211> LENGTH: 16
<212> TYPE: RNA
<213> ORGANISM: Artificial Sequence
<220> FEATURE:
<223> OTHER INFORMATION: asiRNA

```
<400> SEQUENCE: 97
cuguaccugu uaucaa                                                    16

<210> SEQ ID NO 98
<211> LENGTH: 16
<212> TYPE: RNA
<213> ORGANISM: Artificial Sequence
<220> FEATURE:
<223> OTHER INFORMATION: asiRNA

<400> SEQUENCE: 98
gaaugcuuca ugacuu                                                    16

<210> SEQ ID NO 99
<211> LENGTH: 16
<212> TYPE: RNA
<213> ORGANISM: Artificial Sequence
<220> FEATURE:
<223> OTHER INFORMATION: asiRNA

<400> SEQUENCE: 99
ugccuuauca ucucau                                                    16

<210> SEQ ID NO 100
<211> LENGTH: 16
<212> TYPE: RNA
<213> ORGANISM: Artificial Sequence
<220> FEATURE:
<223> OTHER INFORMATION: asiRNA

<400> SEQUENCE: 100
caucucaucu ggaguu                                                    16

<210> SEQ ID NO 101
<211> LENGTH: 21
<212> TYPE: RNA
<213> ORGANISM: Artificial Sequence
<220> FEATURE:
<223> OTHER INFORMATION: asiRNA

<400> SEQUENCE: 101
uggcucaagu aucugcuuug c                                              21

<210> SEQ ID NO 102
<211> LENGTH: 21
<212> TYPE: RNA
<213> ORGANISM: Artificial Sequence
<220> FEATURE:
<223> OTHER INFORMATION: asiRNA

<400> SEQUENCE: 102
gcucaaguau cugcuuugca a                                              21

<210> SEQ ID NO 103
<211> LENGTH: 21
<212> TYPE: RNA
<213> ORGANISM: Artificial Sequence
<220> FEATURE:
<223> OTHER INFORMATION: asiRNA

<400> SEQUENCE: 103
ucaaguaucu gcuuugcaaa u                                              21

<210> SEQ ID NO 104
```

```
<211> LENGTH: 21
<212> TYPE: RNA
<213> ORGANISM: Artificial Sequence
<220> FEATURE:
<223> OTHER INFORMATION: asiRNA

<400> SEQUENCE: 104
aaguaucugc uuugcaaaua g                                              21

<210> SEQ ID NO 105
<211> LENGTH: 21
<212> TYPE: RNA
<213> ORGANISM: Artificial Sequence
<220> FEATURE:
<223> OTHER INFORMATION: asiRNA

<400> SEQUENCE: 105
ucagcauaca cugcacaaug g                                              21

<210> SEQ ID NO 106
<211> LENGTH: 21
<212> TYPE: RNA
<213> ORGANISM: Artificial Sequence
<220> FEATURE:
<223> OTHER INFORMATION: asiRNA

<400> SEQUENCE: 106
agcauacacu gcacaauggc u                                              21

<210> SEQ ID NO 107
<211> LENGTH: 21
<212> TYPE: RNA
<213> ORGANISM: Artificial Sequence
<220> FEATURE:
<223> OTHER INFORMATION: asiRNA

<400> SEQUENCE: 107
cauacacugc acaauggcuc a                                              21

<210> SEQ ID NO 108
<211> LENGTH: 21
<212> TYPE: RNA
<213> ORGANISM: Artificial Sequence
<220> FEATURE:
<223> OTHER INFORMATION: asiRNA

<400> SEQUENCE: 108
uaaccacaag ccaaaaccua u                                              21

<210> SEQ ID NO 109
<211> LENGTH: 21
<212> TYPE: RNA
<213> ORGANISM: Artificial Sequence
<220> FEATURE:
<223> OTHER INFORMATION: asiRNA

<400> SEQUENCE: 109
uuuaucaaca ugcccguuaa c                                              21

<210> SEQ ID NO 110
<211> LENGTH: 21
<212> TYPE: RNA
<213> ORGANISM: Artificial Sequence
<220> FEATURE:
<223> OTHER INFORMATION: asiRNA

<400> SEQUENCE: 110
```
agauuccuua ggauaugauc u                                              21

<210> SEQ ID NO 111
<211> LENGTH: 21
<212> TYPE: RNA
<213> ORGANISM: Artificial Sequence
<220> FEATURE:
<223> OTHER INFORMATION: asiRNA

<400> SEQUENCE: 111
ccugguuuuc ugagauuccu u                                              21

<210> SEQ ID NO 112
<211> LENGTH: 21
<212> TYPE: RNA
<213> ORGANISM: Artificial Sequence
<220> FEATURE:
<223> OTHER INFORMATION: asiRNA

<400> SEQUENCE: 112
ugguuuucug agauuccuua g                                              21

<210> SEQ ID NO 113
<211> LENGTH: 21
<212> TYPE: RNA
<213> ORGANISM: Artificial Sequence
<220> FEATURE:
<223> OTHER INFORMATION: asiRNA

<400> SEQUENCE: 113 guuucugag auuccuuagg a                                               21

<210> SEQ ID NO 114
<211> LENGTH: 21
<212> TYPE: RNA
<213> ORGANISM: Artificial Sequence
<220> FEATURE:
<223> OTHER INFORMATION: asiRNA

<400> SEQUENCE: 114
gguauuuugu auccaguauc u                                              21

<210> SEQ ID NO 115
<211> LENGTH: 21
<212> TYPE: RNA
<213> ORGANISM: Artificial Sequence
<220> FEATURE:
<223> OTHER INFORMATION: asiRNA

<400> SEQUENCE: 115
uauuuuguau ccaguaucuc c                                              21

<210> SEQ ID NO 116
<211> LENGTH: 21
<212> TYPE: RNA
<213> ORGANISM: Artificial Sequence
<220> FEATURE:
<223> OTHER INFORMATION: asiRNA

<400> SEQUENCE: 116
uuuuguaucc aguaucccu g                                               21

<210> SEQ ID NO 117
<211> LENGTH: 21
<212> TYPE: RNA

<213> ORGANISM: Artificial Sequence
<220> FEATURE:
<223> OTHER INFORMATION: asiRNA

<400> SEQUENCE: 117
uuguauccag uaucuccugg u    21

<210> SEQ ID NO 118
<211> LENGTH: 21
<212> TYPE: RNA
<213> ORGANISM: Artificial Sequence
<220> FEATURE:
<223> OTHER INFORMATION: asiRNA

<400> SEQUENCE: 118
guauccagua ucuccugguu u    21

<210> SEQ ID NO 119
<211> LENGTH: 21
<212> TYPE: RNA
<213> ORGANISM: Artificial Sequence
<220> FEATURE:
<223> OTHER INFORMATION: asiRNA

<400> SEQUENCE: 119
auccaguauc uccugguuuu c    21

<210> SEQ ID NO 120
<211> LENGTH: 21
<212> TYPE: RNA
<213> ORGANISM: Artificial Sequence
<220> FEATURE:
<223> OTHER INFORMATION: asiRNA

<400> SEQUENCE: 120
gccuccccuu gguauuuugu a    21

<210> SEQ ID NO 121
<211> LENGTH: 21
<212> TYPE: RNA
<213> ORGANISM: Artificial Sequence
<220> FEATURE:
<223> OTHER INFORMATION: asiRNA

<400> SEQUENCE: 121 cucccccuugg uauuuuguau c    21

<210> SEQ ID NO 122
<211> LENGTH: 21
<212> TYPE: RNA
<213> ORGANISM: Artificial Sequence
<220> FEATURE:
<223> OTHER INFORMATION: asiRNA

<400> SEQUENCE: 122
uauucaaaua agccuccccu u    21

<210> SEQ ID NO 123
<211> LENGTH: 21
<212> TYPE: RNA
<213> ORGANISM: Artificial Sequence
<220> FEATURE:
<223> OTHER INFORMATION: asiRNA

<400> SEQUENCE: 123
ccaaaauagu uggcugcagu u    21

<210> SEQ ID NO 124
<211> LENGTH: 21
<212> TYPE: RNA
<213> ORGANISM: Artificial Sequence
<220> FEATURE:
<223> OTHER INFORMATION: asiRNA

<400> SEQUENCE: 124
aaaauaguug gcugcaguua c                                              21

<210> SEQ ID NO 125
<211> LENGTH: 21
<212> TYPE: RNA
<213> ORGANISM: Artificial Sequence
<220> FEATURE:
<223> OTHER INFORMATION: asiRNA

<400> SEQUENCE: 125
aauaguuggc ugcaguuacg u                                              21

<210> SEQ ID NO 126
<211> LENGTH: 21
<212> TYPE: RNA
<213> ORGANISM: Artificial Sequence
<220> FEATURE:
<223> OTHER INFORMATION: asiRNA

<400> SEQUENCE: 126
uaguuggcug caguuacgua u                                              21

<210> SEQ ID NO 127
<211> LENGTH: 21
<212> TYPE: RNA
<213> ORGANISM: Artificial Sequence
<220> FEATURE:
<223> OTHER INFORMATION: asiRNA

<400> SEQUENCE: 127
guuggcugca guuacguauu c                                              21

<210> SEQ ID NO 128
<211> LENGTH: 21
<212> TYPE: RNA
<213> ORGANISM: Artificial Sequence
<220> FEATURE:
<223> OTHER INFORMATION: asiRNA

<400> SEQUENCE: 128
agccacacca cuccaugauu u                                              21

<210> SEQ ID NO 129
<211> LENGTH: 21
<212> TYPE: RNA
<213> ORGANISM: Artificial Sequence
<220> FEATURE:
<223> OTHER INFORMATION: asiRNA

<400> SEQUENCE: 129
ccacaccacu ccaugauuuc u                                              21

<210> SEQ ID NO 130
<211> LENGTH: 21
<212> TYPE: RNA
<213> ORGANISM: Artificial Sequence
<220> FEATURE:

<223> OTHER INFORMATION: asiRNA

<400> SEQUENCE: 130
acaccacucc augauuucuc c                                      21

<210> SEQ ID NO 131
<211> LENGTH: 21
<212> TYPE: RNA
<213> ORGANISM: Artificial Sequence
<220> FEATURE:
<223> OTHER INFORMATION: asiRNA

<400> SEQUENCE: 131
accacuccau gauuucucca a                                      21

<210> SEQ ID NO 132
<211> LENGTH: 21
<212> TYPE: RNA
<213> ORGANISM: Artificial Sequence
<220> FEATURE:
<223> OTHER INFORMATION: asiRNA

<400> SEQUENCE: 132
cacuccauga uuucuccaaa a                                      21

<210> SEQ ID NO 133
<211> LENGTH: 21
<212> TYPE: RNA
<213> ORGANISM: Artificial Sequence
<220> FEATURE:
<223> OTHER INFORMATION: asiRNA

<400> SEQUENCE: 133
gaccagcugg ccagggcaua g                                      21

<210> SEQ ID NO 134
<211> LENGTH: 21
<212> TYPE: RNA
<213> ORGANISM: Artificial Sequence
<220> FEATURE:
<223> OTHER INFORMATION: asiRNA

<400> SEQUENCE: 134
agcuggccag ggcauagcca c                                      21

<210> SEQ ID NO 135
<211> LENGTH: 21
<212> TYPE: RNA
<213> ORGANISM: Artificial Sequence
<220> FEATURE:
<223> OTHER INFORMATION: asiRNA

<400> SEQUENCE: 135
cuggccaggg cauagccaca c                                      21

<210> SEQ ID NO 136
<211> LENGTH: 21
<212> TYPE: RNA
<213> ORGANISM: Artificial Sequence
<220> FEATURE:
<223> OTHER INFORMATION: asiRNA

<400> SEQUENCE: 136
gagguaccac ucaugaugcu c                                      21

```
<210> SEQ ID NO 137
<211> LENGTH: 21
<212> TYPE: RNA
<213> ORGANISM: Artificial Sequence
<220> FEATURE:
<223> OTHER INFORMATION: asiRNA

<400> SEQUENCE: 137
gguaccacuc augaugcucu u                                             21

<210> SEQ ID NO 138
<211> LENGTH: 21
<212> TYPE: RNA
<213> ORGANISM: Artificial Sequence
<220> FEATURE:
<223> OTHER INFORMATION: asiRNA

<400> SEQUENCE: 138
ucuucaaauu uccggaggua c                                             21

<210> SEQ ID NO 139
<211> LENGTH: 21
<212> TYPE: RNA
<213> ORGANISM: Artificial Sequence
<220> FEATURE:
<223> OTHER INFORMATION: asiRNA

<400> SEQUENCE: 139
ucaucagcau acacugcaca a                                             21

<210> SEQ ID NO 140
<211> LENGTH: 21
<212> TYPE: RNA
<213> ORGANISM: Artificial Sequence
<220> FEATURE:
<223> OTHER INFORMATION: asiRNA

<400> SEQUENCE: 140
auguuuauca acaugcccgu u                                             21

<210> SEQ ID NO 141
<211> LENGTH: 21
<212> TYPE: RNA
<213> ORGANISM: Artificial Sequence
<220> FEATURE:
<223> OTHER INFORMATION: asiRNA

<400> SEQUENCE: 141
gccagggcau agccacacca c                                             21

<210> SEQ ID NO 142
<211> LENGTH: 21
<212> TYPE: RNA
<213> ORGANISM: Artificial Sequence
<220> FEATURE:
<223> OTHER INFORMATION: asiRNA

<400> SEQUENCE: 142
cagggcauag ccacaccacu c                                             21

<210> SEQ ID NO 143
<211> LENGTH: 21
<212> TYPE: RNA
<213> ORGANISM: Artificial Sequence
<220> FEATURE:
<223> OTHER INFORMATION: asiRNA
```

<400> SEQUENCE: 143
gggcauagcc acaccacucc a                                                 21

<210> SEQ ID NO 144
<211> LENGTH: 21
<212> TYPE: RNA
<213> ORGANISM: Artificial Sequence
<220> FEATURE:
<223> OTHER INFORMATION: asiRNA

<400> SEQUENCE: 144
gcauagccac accacuccau g                                                 21

<210> SEQ ID NO 145
<211> LENGTH: 21
<212> TYPE: RNA
<213> ORGANISM: Artificial Sequence
<220> FEATURE:
<223> OTHER INFORMATION: asiRNA

<400> SEQUENCE: 145
aaacaaaacg ugaagaaagc a                                                 21

<210> SEQ ID NO 146
<211> LENGTH: 21
<212> TYPE: RNA
<213> ORGANISM: Artificial Sequence
<220> FEATURE:
<223> OTHER INFORMATION: asiRNA

<400> SEQUENCE: 146
aaaggguucu caagucaggc u                                                 21

<210> SEQ ID NO 147
<211> LENGTH: 21
<212> TYPE: RNA
<213> ORGANISM: Artificial Sequence
<220> FEATURE:
<223> OTHER INFORMATION: asiRNA

<400> SEQUENCE: 147
uuguacacgc caacaguggc a                                                 21

<210> SEQ ID NO 148
<211> LENGTH: 21
<212> TYPE: RNA
<213> ORGANISM: Artificial Sequence
<220> FEATURE:
<223> OTHER INFORMATION: asiRNA

<400> SEQUENCE: 148
uuacguauuc aaauaagccu c                                                 21

<210> SEQ ID NO 149
<211> LENGTH: 21
<212> TYPE: RNA
<213> ORGANISM: Artificial Sequence
<220> FEATURE:
<223> OTHER INFORMATION: asiRNA

<400> SEQUENCE: 149
agaagcgcca uuggaaagcu u                                                 21

<210> SEQ ID NO 150
<211> LENGTH: 21

```
<212> TYPE: RNA
<213> ORGANISM: Artificial Sequence
<220> FEATURE:
<223> OTHER INFORMATION: asiRNA

<400> SEQUENCE: 150
aaguccagau gccuuugccu c                                              21

<210> SEQ ID NO 151
<211> LENGTH: 21
<212> TYPE: RNA
<213> ORGANISM: Artificial Sequence
<220> FEATURE:
<223> OTHER INFORMATION: asiRNA

<400> SEQUENCE: 151
accagagcac auugauggcu c                                              21

<210> SEQ ID NO 152
<211> LENGTH: 21
<212> TYPE: RNA
<213> ORGANISM: Artificial Sequence
<220> FEATURE:
<223> OTHER INFORMATION: asiRNA

<400> SEQUENCE: 152
guuacagaaa gugaucauuc u                                              21

<210> SEQ ID NO 153
<211> LENGTH: 21
<212> TYPE: RNA
<213> ORGANISM: Artificial Sequence
<220> FEATURE:
<223> OTHER INFORMATION: asiRNA

<400> SEQUENCE: 153
cuauuagaag gaagauuagc u                                              21

<210> SEQ ID NO 154
<211> LENGTH: 21
<212> TYPE: RNA
<213> ORGANISM: Artificial Sequence
<220> FEATURE:
<223> OTHER INFORMATION: asiRNA

<400> SEQUENCE: 154
aaggcaaagc aaugccagau g                                              21

<210> SEQ ID NO 155
<211> LENGTH: 21
<212> TYPE: RNA
<213> ORGANISM: Artificial Sequence
<220> FEATURE:
<223> OTHER INFORMATION: asiRNA

<400> SEQUENCE: 155
uaaucgccau uguacacgcc a                                              21

<210> SEQ ID NO 156
<211> LENGTH: 21
<212> TYPE: RNA
<213> ORGANISM: Artificial Sequence
<220> FEATURE:
<223> OTHER INFORMATION: asiRNA

<400> SEQUENCE: 156
```
aaaguccaua gagaagcgcc a                                              21

<210> SEQ ID NO 157
<211> LENGTH: 21
<212> TYPE: RNA
<213> ORGANISM: Artificial Sequence
<220> FEATURE:
<223> OTHER INFORMATION: asiRNA

<400> SEQUENCE: 157
uugccucacc uuggaagggc c                                              21

<210> SEQ ID NO 158
<211> LENGTH: 21
<212> TYPE: RNA
<213> ORGANISM: Artificial Sequence
<220> FEATURE:
<223> OTHER INFORMATION: asiRNA

<400> SEQUENCE: 158
uuugccucac cuuggaaggg c                                              21

<210> SEQ ID NO 159
<211> LENGTH: 21
<212> TYPE: RNA
<213> ORGANISM: Artificial Sequence
<220> FEATURE:
<223> OTHER INFORMATION: asiRNA

<400> SEQUENCE: 159
uuacuccgua ugaaccacca c                                              21

<210> SEQ ID NO 160
<211> LENGTH: 21
<212> TYPE: RNA
<213> ORGANISM: Artificial Sequence
<220> FEATURE:
<223> OTHER INFORMATION: asiRNA

<400> SEQUENCE: 160
caacaaucuc uacuauaucc a                                              21

<210> SEQ ID NO 161
<211> LENGTH: 21
<212> TYPE: RNA
<213> ORGANISM: Artificial Sequence
<220> FEATURE:
<223> OTHER INFORMATION: asiRNA

<400> SEQUENCE: 161
aauuucacag acaacaaucu c                                              21

<210> SEQ ID NO 162
<211> LENGTH: 21
<212> TYPE: RNA
<213> ORGANISM: Artificial Sequence
<220> FEATURE:
<223> OTHER INFORMATION: asiRNA

<400> SEQUENCE: 162
uuacccagag cuugaaauuc u                                              21

<210> SEQ ID NO 163
<211> LENGTH: 21
<212> TYPE: RNA
<213> ORGANISM: Artificial Sequence

```
<220> FEATURE:
<223> OTHER INFORMATION: asiRNA

<400> SEQUENCE: 163
agguacuuau uagguagauu g                                              21

<210> SEQ ID NO 164
<211> LENGTH: 21
<212> TYPE: RNA
<213> ORGANISM: Artificial Sequence
<220> FEATURE:
<223> OTHER INFORMATION: asiRNA

<400> SEQUENCE: 164
uuucacagac aacaaucucu a                                              21

<210> SEQ ID NO 165
<211> LENGTH: 21
<212> TYPE: RNA
<213> ORGANISM: Artificial Sequence
<220> FEATURE:
<223> OTHER INFORMATION: asiRNA

<400> SEQUENCE: 165
ucaugaugcu cuuuugcucu a                                              21

<210> SEQ ID NO 166
<211> LENGTH: 21
<212> TYPE: RNA
<213> ORGANISM: Artificial Sequence
<220> FEATURE:
<223> OTHER INFORMATION: asiRNA

<400> SEQUENCE: 166
uuuacaaagu ccauagagaa g                                              21

<210> SEQ ID NO 167
<211> LENGTH: 21
<212> TYPE: RNA
<213> ORGANISM: Artificial Sequence
<220> FEATURE:
<223> OTHER INFORMATION: asiRNA

<400> SEQUENCE: 167
augccaucaa agacaguugu a                                              21

<210> SEQ ID NO 168
<211> LENGTH: 21
<212> TYPE: RNA
<213> ORGANISM: Artificial Sequence
<220> FEATURE:
<223> OTHER INFORMATION: asiRNA

<400> SEQUENCE: 168
guacuuauua gguagauugc a                                              21

<210> SEQ ID NO 169
<211> LENGTH: 21
<212> TYPE: RNA
<213> ORGANISM: Artificial Sequence
<220> FEATURE:
<223> OTHER INFORMATION: asiRNA

<400> SEQUENCE: 169
uuagaaggaa gauuagcuau g                                              21
```

```
<210> SEQ ID NO 170
<211> LENGTH: 21
<212> TYPE: RNA
<213> ORGANISM: Artificial Sequence
<220> FEATURE:
<223> OTHER INFORMATION: asiRNA

<400> SEQUENCE: 170
uauuguucug aaaaugccau c                                              21

<210> SEQ ID NO 171
<211> LENGTH: 21
<212> TYPE: RNA
<213> ORGANISM: Artificial Sequence
<220> FEATURE:
<223> OTHER INFORMATION: asiRNA

<400> SEQUENCE: 171
ugaccuugaa gagaucacug u                                              21

<210> SEQ ID NO 172
<211> LENGTH: 21
<212> TYPE: RNA
<213> ORGANISM: Artificial Sequence
<220> FEATURE:
<223> OTHER INFORMATION: asiRNA

<400> SEQUENCE: 172
ucacagacaa caaucucuac u                                              21

<210> SEQ ID NO 173
<211> LENGTH: 21
<212> TYPE: RNA
<213> ORGANISM: Artificial Sequence
<220> FEATURE:
<223> OTHER INFORMATION: asiRNA

<400> SEQUENCE: 173
acagacaaca aucucuacua u                                              21

<210> SEQ ID NO 174
<211> LENGTH: 21
<212> TYPE: RNA
<213> ORGANISM: Artificial Sequence
<220> FEATURE:
<223> OTHER INFORMATION: asiRNA

<400> SEQUENCE: 174
uacacugagu ucgucugacg a                                              21

<210> SEQ ID NO 175
<211> LENGTH: 21
<212> TYPE: RNA
<213> ORGANISM: Artificial Sequence
<220> FEATURE:
<223> OTHER INFORMATION: asiRNA

<400> SEQUENCE: 175
aacauggcca ggaggaugca g                                              21

<210> SEQ ID NO 176
<211> LENGTH: 21
<212> TYPE: RNA
<213> ORGANISM: Artificial Sequence
<220> FEATURE:
<223> OTHER INFORMATION: asiRNA
```

```
<400> SEQUENCE: 176
aaauggguaa auuaagcacc g                                              21

<210> SEQ ID NO 177
<211> LENGTH: 21
<212> TYPE: RNA
<213> ORGANISM: Artificial Sequence
<220> FEATURE:
<223> OTHER INFORMATION: asiRNA

<400> SEQUENCE: 177
uuuccuccuc gcaucagaaa u                                              21

<210> SEQ ID NO 178
<211> LENGTH: 21
<212> TYPE: RNA
<213> ORGANISM: Artificial Sequence
<220> FEATURE:
<223> OTHER INFORMATION: asiRNA

<400> SEQUENCE: 178
uuacagguac agaacauaau c                                              21

<210> SEQ ID NO 179
<211> LENGTH: 21
<212> TYPE: RNA
<213> ORGANISM: Artificial Sequence
<220> FEATURE:
<223> OTHER INFORMATION: asiRNA

<400> SEQUENCE: 179
aaauagccgu uacagguaca g                                              21

<210> SEQ ID NO 180
<211> LENGTH: 21
<212> TYPE: RNA
<213> ORGANISM: Artificial Sequence
<220> FEATURE:
<223> OTHER INFORMATION: .asiRNA

<400> SEQUENCE: 180
auacacugca caauggcuca a                                              21

<210> SEQ ID NO 181
<211> LENGTH: 21
<212> TYPE: RNA
<213> ORGANISM: Artificial Sequence
<220> FEATURE:
<223> OTHER INFORMATION: asiRNA

<400> SEQUENCE: 181
gaucugaaug gauguuuauc a                                              21

<210> SEQ ID NO 182
<211> LENGTH: 21
<212> TYPE: RNA
<213> ORGANISM: Artificial Sequence
<220> FEATURE:
<223> OTHER INFORMATION: asiRNA

<400> SEQUENCE: 182
uucugaacuu uggauacucu u                                              21

<210> SEQ ID NO 183
```

<211> LENGTH: 21
<212> TYPE: RNA
<213> ORGANISM: Artificial Sequence
<220> FEATURE:
<223> OTHER INFORMATION: asiRNA

<400> SEQUENCE: 183
uucagcguau uuagguacuu a                                              21

<210> SEQ ID NO 184
<211> LENGTH: 21
<212> TYPE: RNA
<213> ORGANISM: Artificial Sequence
<220> FEATURE:
<223> OTHER INFORMATION: asiRNA

<400> SEQUENCE: 184
aaccuccauu ucagcguauu u                                              21

<210> SEQ ID NO 185
<211> LENGTH: 21
<212> TYPE: RNA
<213> ORGANISM: Artificial Sequence
<220> FEATURE:
<223> OTHER INFORMATION: asiRNA

<400> SEQUENCE: 185
auauucaacc uccauuucag c                                              21

<210> SEQ ID NO 186
<211> LENGTH: 21
<212> TYPE: RNA
<213> ORGANISM: Artificial Sequence
<220> FEATURE:
<223> OTHER INFORMATION: asiRNA

<400> SEQUENCE: 186
uuacacagua ggauauucaa c                                              21

<210> SEQ ID NO 187
<211> LENGTH: 21
<212> TYPE: RNA
<213> ORGANISM: Artificial Sequence
<220> FEATURE:
<223> OTHER INFORMATION: asiRNA

<400> SEQUENCE: 187
aaagucuagu cucauacaca c                                              21

<210> SEQ ID NO 188
<211> LENGTH: 21
<212> TYPE: RNA
<213> ORGANISM: Artificial Sequence
<220> FEATURE:
<223> OTHER INFORMATION: asiRNA

<400> SEQUENCE: 188
aagggauugu gacauuuauu g                                              21

<210> SEQ ID NO 189
<211> LENGTH: 21
<212> TYPE: RNA
<213> ORGANISM: Artificial Sequence
<220> FEATURE:
<223> OTHER INFORMATION: asiRNA

<400> SEQUENCE: 189
aacacugcag uugaccuuga a         21

<210> SEQ ID NO 190
<211> LENGTH: 21
<212> TYPE: RNA
<213> ORGANISM: Artificial Sequence
<220> FEATURE:
<223> OTHER INFORMATION: asiRNA

<400> SEQUENCE: 190
augacugcac aauggcuacc c         21

<210> SEQ ID NO 191
<211> LENGTH: 21
<212> TYPE: RNA
<213> ORGANISM: Artificial Sequence
<220> FEATURE:
<223> OTHER INFORMATION: asiRNA

<400> SEQUENCE: 191
aaguucucca cuuacacaca g         21

<210> SEQ ID NO 192
<211> LENGTH: 21
<212> TYPE: RNA
<213> ORGANISM: Artificial Sequence
<220> FEATURE:
<223> OTHER INFORMATION: asiRNA

<400> SEQUENCE: 192
acucacacag gcagagcagc u         21

<210> SEQ ID NO 193
<211> LENGTH: 21
<212> TYPE: RNA
<213> ORGANISM: Artificial Sequence
<220> FEATURE:
<223> OTHER INFORMATION: asiRNA

<400> SEQUENCE: 193
auugauggcu cacggugagu g         21

<210> SEQ ID NO 194
<211> LENGTH: 21
<212> TYPE: RNA
<213> ORGANISM: Artificial Sequence
<220> FEATURE:
<223> OTHER INFORMATION: asiRNA

<400> SEQUENCE: 194
aagacagaga gaaaccaugu c         21

<210> SEQ ID NO 195
<211> LENGTH: 21
<212> TYPE: RNA
<213> ORGANISM: Artificial Sequence
<220> FEATURE:
<223> OTHER INFORMATION: asiRNA

<400> SEQUENCE: 195
aacuaggucu agacuagaag a         21

<210> SEQ ID NO 196
<211> LENGTH: 21
<212> TYPE: RNA

```
<213> ORGANISM: Artificial Sequence
<220> FEATURE:
<223> OTHER INFORMATION: asiRNA

<400> SEQUENCE: 196
aucauucuuu acacuacaag g                                              21

<210> SEQ ID NO 197
<211> LENGTH: 21
<212> TYPE: RNA
<213> ORGANISM: Artificial Sequence
<220> FEATURE:
<223> OTHER INFORMATION: asiRNA

<400> SEQUENCE: 197
uugauaacag guacaggcua u                                              21

<210> SEQ ID NO 198
<211> LENGTH: 21
<212> TYPE: RNA
<213> ORGANISM: Artificial Sequence
<220> FEATURE:
<223> OTHER INFORMATION: asiRNA

<400> SEQUENCE: 198
aagucaugaa gcauucaaca g                                              21

<210> SEQ ID NO 199
<211> LENGTH: 21
<212> TYPE: RNA
<213> ORGANISM: Artificial Sequence
<220> FEATURE:
<223> OTHER INFORMATION: asiRNA

<400> SEQUENCE: 199
augagaugau aaggcaaagc a                                              21

<210> SEQ ID NO 200
<211> LENGTH: 21
<212> TYPE: RNA
<213> ORGANISM: Artificial Sequence
<220> FEATURE:
<223> OTHER INFORMATION: asiRNA

<400> SEQUENCE: 200
aacuccagau gagaugauaa g                                              21

<210> SEQ ID NO 201
<211> LENGTH: 16
<212> TYPE: RNA
<213> ORGANISM: Artificial Sequence
<220> FEATURE:
<223> OTHER INFORMATION: asiRNA

<400> SEQUENCE: 201
guuccugcag gagcug                                                    16

<210> SEQ ID NO 202
<211> LENGTH: 16
<212> TYPE: RNA
<213> ORGANISM: Artificial Sequence
<220> FEATURE:
<223> OTHER INFORMATION: asiRNA

<400> SEQUENCE: 202
uuccugcagg agcugc                                                    16
```

```
<210> SEQ ID NO 203
<211> LENGTH: 16
<212> TYPE: RNA
<213> ORGANISM: Artificial Sequence
<220> FEATURE:
<223> OTHER INFORMATION: asiRNA

<400> SEQUENCE: 203
uccugcagga gcugcc                                                       16

<210> SEQ ID NO 204
<211> LENGTH: 16
<212> TYPE: RNA
<213> ORGANISM: Artificial Sequence
<220> FEATURE:
<223> OTHER INFORMATION: asiRNA

<400> SEQUENCE: 204
ccugcaggag cugccu                                                       16

<210> SEQ ID NO 205
<211> LENGTH: 16
<212> TYPE: RNA
<213> ORGANISM: Artificial Sequence
<220> FEATURE:
<223> OTHER INFORMATION: asiRNA

<400> SEQUENCE: 205
cugcaggagc ugccuu                                                       16

<210> SEQ ID NO 206
<211> LENGTH: 16
<212> TYPE: RNA
<213> ORGANISM: Artificial Sequence
<220> FEATURE:
<223> OTHER INFORMATION: asiRNA

<400> SEQUENCE: 206
ugcaggagcu gccuuc                                                       16

<210> SEQ ID NO 207
<211> LENGTH: 16
<212> TYPE: RNA
<213> ORGANISM: Artificial Sequence
<220> FEATURE:
<223> OTHER INFORMATION: asiRNA

<400> SEQUENCE: 207
gcaggagcug ccuucc                                                       16

<210> SEQ ID NO 208
<211> LENGTH: 16
<212> TYPE: RNA
<213> ORGANISM: Artificial Sequence
<220> FEATURE:
<223> OTHER INFORMATION: asiRNA

<400> SEQUENCE: 208
caggagcugc cuuccu                                                       16

<210> SEQ ID NO 209
<211> LENGTH: 16
<212> TYPE: RNA
<213> ORGANISM: Artificial Sequence
<220> FEATURE:
```

```
<223> OTHER INFORMATION: asiRNA

<400> SEQUENCE: 209
aggagcugcc uuccuu                                                   16

<210> SEQ ID NO 210
<211> LENGTH: 16
<212> TYPE: RNA
<213> ORGANISM: Artificial Sequence
<220> FEATURE:
<223> OTHER INFORMATION: asiRNA

<400> SEQUENCE: 210
acuuccacag gacauu                                                   16

<210> SEQ ID NO 211
<211> LENGTH: 16
<212> TYPE: RNA
<213> ORGANISM: Artificial Sequence
<220> FEATURE:
<223> OTHER INFORMATION: asiRNA

<400> SEQUENCE: 211
cuuccacagg acauuu                                                   16

<210> SEQ ID NO 212
<211> LENGTH: 16
<212> TYPE: RNA
<213> ORGANISM: Artificial Sequence
<220> FEATURE:
<223> OTHER INFORMATION: asiRNA

<400> SEQUENCE: 212
agguggcuug uuuacg                                                   16

<210> SEQ ID NO 213
<211> LENGTH: 16
<212> TYPE: RNA
<213> ORGANISM: Artificial Sequence
<220> FEATURE:
<223> OTHER INFORMATION: asiRNA

<400> SEQUENCE: 213
gguggcuugu uuacgu                                                   16

<210> SEQ ID NO 214
<211> LENGTH: 16
<212> TYPE: RNA
<213> ORGANISM: Artificial Sequence
<220> FEATURE:
<223> OTHER INFORMATION: asiRNA

<400> SEQUENCE: 214
guggcuuguu uacgua                                                   16

<210> SEQ ID NO 215
<211> LENGTH: 16
<212> TYPE: RNA
<213> ORGANISM: Artificial Sequence
<220> FEATURE:
<223> OTHER INFORMATION: asiRNA

<400> SEQUENCE: 215
uggcuuguuu acguau                                                   16
```

```
<210> SEQ ID NO 216
<211> LENGTH: 16
<212> TYPE: RNA
<213> ORGANISM: Artificial Sequence
<220> FEATURE:
<223> OTHER INFORMATION: asiRNA

<400> SEQUENCE: 216
ggcuuguuua cguaug                                                        16

<210> SEQ ID NO 217
<211> LENGTH: 16
<212> TYPE: RNA
<213> ORGANISM: Artificial Sequence
<220> FEATURE:
<223> OTHER INFORMATION: asiRNA

<400> SEQUENCE: 217
gcuuguuuac guaugu                                                        16

<210> SEQ ID NO 218
<211> LENGTH: 16
<212> TYPE: RNA
<213> ORGANISM: Artificial Sequence
<220> FEATURE:
<223> OTHER INFORMATION: asiRNA

<400> SEQUENCE: 218
cuaccucaag auguuu                                                        16

<210> SEQ ID NO 219
<211> LENGTH: 16
<212> TYPE: RNA
<213> ORGANISM: Artificial Sequence
<220> FEATURE:
<223> OTHER INFORMATION: asiRNA

<400> SEQUENCE: 219
gguuccugca ggagcu                                                        16

<210> SEQ ID NO 220
<211> LENGTH: 16
<212> TYPE: RNA
<213> ORGANISM: Artificial Sequence
<220> FEATURE:
<223> OTHER INFORMATION: asiRNA

<400> SEQUENCE: 220
uacuuccaca ggacau                                                        16

<210> SEQ ID NO 221
<211> LENGTH: 16
<212> TYPE: RNA
<213> ORGANISM: Artificial Sequence
<220> FEATURE:
<223> OTHER INFORMATION: asiRNA

<400> SEQUENCE: 221
agacauacgg uuuagc                                                        16

<210> SEQ ID NO 222
<211> LENGTH: 16
<212> TYPE: RNA
<213> ORGANISM: Artificial Sequence
<220> FEATURE:
<223> OTHER INFORMATION: asiRNA
```

```
<400> SEQUENCE: 222
cagacauacg guuuag                                                        16

<210> SEQ ID NO 223
<211> LENGTH: 16
<212> TYPE: RNA
<213> ORGANISM: Artificial Sequence
<220> FEATURE:
<223> OTHER INFORMATION: asiRNA

<400> SEQUENCE: 223
acagacauac gguuua                                                        16

<210> SEQ ID NO 224
<211> LENGTH: 16
<212> TYPE: RNA
<213> ORGANISM: Artificial Sequence
<220> FEATURE:
<223> OTHER INFORMATION: asiRNA

<400> SEQUENCE: 224
cacagacaua cgguuu                                                        16

<210> SEQ ID NO 225
<211> LENGTH: 16
<212> TYPE: RNA
<213> ORGANISM: Artificial Sequence
<220> FEATURE:
<223> OTHER INFORMATION: asiRNA

<400> SEQUENCE: 225
ggauuccaca aggugg                                                        16

<210> SEQ ID NO 226
<211> LENGTH: 16
<212> TYPE: RNA
<213> ORGANISM: Artificial Sequence
<220> FEATURE:
<223> OTHER INFORMATION: asiRNA

<400> SEQUENCE: 226
gauuccacaa gguggc                                                        16

<210> SEQ ID NO 227
<211> LENGTH: 16
<212> TYPE: RNA
<213> ORGANISM: Artificial Sequence
<220> FEATURE:
<223> OTHER INFORMATION: asiRNA

<400> SEQUENCE: 227
auuccacaag guggcu                                                        16

<210> SEQ ID NO 228
<211> LENGTH: 16
<212> TYPE: RNA
<213> ORGANISM: Artificial Sequence
<220> FEATURE:
<223> OTHER INFORMATION: asiRNA

<400> SEQUENCE: 228
uuccacaagg uggcuu                                                        16

<210> SEQ ID NO 229
<211> LENGTH: 16
```

```
<212> TYPE: RNA
<213> ORGANISM: Artificial Sequence
<220> FEATURE:
<223> OTHER INFORMATION: asiRNA

<400> SEQUENCE: 229
uccacaaggu ggcuug                                               16

<210> SEQ ID NO 230
<211> LENGTH: 16
<212> TYPE: RNA
<213> ORGANISM: Artificial Sequence
<220> FEATURE:
<223> OTHER INFORMATION: asiRNA

<400> SEQUENCE: 230
ccacaaggug gcuugu                                               16

<210> SEQ ID NO 231
<211> LENGTH: 16
<212> TYPE: RNA
<213> ORGANISM: Artificial Sequence
<220> FEATURE:
<223> OTHER INFORMATION: asiRNA

<400> SEQUENCE: 231
cacaaggugg cuuguu                                               16

<210> SEQ ID NO 232
<211> LENGTH: 16
<212> TYPE: RNA
<213> ORGANISM: Artificial Sequence
<220> FEATURE:
<223> OTHER INFORMATION: asiRNA

<400> SEQUENCE: 232
acaagguggc uuguuu                                               16

<210> SEQ ID NO 233
<211> LENGTH: 16
<212> TYPE: RNA
<213> ORGANISM: Artificial Sequence
<220> FEATURE:
<223> OTHER INFORMATION: asiRNA

<400> SEQUENCE: 233
caagguggcu uguuua                                               16

<210> SEQ ID NO 234
<211> LENGTH: 16
<212> TYPE: RNA
<213> ORGANISM: Artificial Sequence
<220> FEATURE:
<223> OTHER INFORMATION: asiRNA

<400> SEQUENCE: 234
aagguggcuu guuuac                                               16

<210> SEQ ID NO 235
<211> LENGTH: 16
<212> TYPE: RNA
<213> ORGANISM: Artificial Sequence
<220> FEATURE:
<223> OTHER INFORMATION: asiRNA

<400> SEQUENCE: 235
```
cuggagccaa uuuccu                                                     16

<210> SEQ ID NO 236
<211> LENGTH: 16
<212> TYPE: RNA
<213> ORGANISM: Artificial Sequence
<220> FEATURE:
<223> OTHER INFORMATION: asiRNA

<400> SEQUENCE: 236
ucuggagcca auuucc                                                     16

<210> SEQ ID NO 237
<211> LENGTH: 16
<212> TYPE: RNA
<213> ORGANISM: Artificial Sequence
<220> FEATURE:
<223> OTHER INFORMATION: asiRNA

<400> SEQUENCE: 237
uucuggagcc aauuuc                                                     16

<210> SEQ ID NO 238
<211> LENGTH: 16
<212> TYPE: RNA
<213> ORGANISM: Artificial Sequence
<220> FEATURE:
<223> OTHER INFORMATION: asiRNA

<400> SEQUENCE: 238
uuucuggagc caauuu                                                     16

<210> SEQ ID NO 239
<211> LENGTH: 16
<212> TYPE: RNA
<213> ORGANISM: Artificial Sequence
<220> FEATURE:
<223> OTHER INFORMATION: asiRNA

<400> SEQUENCE: 239
guuucuggag ccaauu                                                     16

<210> SEQ ID NO 240
<211> LENGTH: 16
<212> TYPE: RNA
<213> ORGANISM: Artificial Sequence
<220> FEATURE:
<223> OTHER INFORMATION: asiRNA

<400> SEQUENCE: 240
uguuucugga gccaau                                                     16

<210> SEQ ID NO 241
<211> LENGTH: 16
<212> TYPE: RNA
<213> ORGANISM: Artificial Sequence
<220> FEATURE:
<223> OTHER INFORMATION: asiRNA

<400> SEQUENCE: 241
auguuucugg agccaa                                                     16

<210> SEQ ID NO 242
<211> LENGTH: 16
<212> TYPE: RNA
<213> ORGANISM: Artificial Sequence

```
<220> FEATURE:
<223> OTHER INFORMATION: asiRNA

<400> SEQUENCE: 242
uauguuucug gagcca                                                        16

<210> SEQ ID NO 243
<211> LENGTH: 16
<212> TYPE: RNA
<213> ORGANISM: Artificial Sequence
<220> FEATURE:
<223> OTHER INFORMATION: asiRNA

<400> SEQUENCE: 243
guauguuucu ggagcc                                                        16

<210> SEQ ID NO 244
<211> LENGTH: 16
<212> TYPE: RNA
<213> ORGANISM: Artificial Sequence
<220> FEATURE:
<223> OTHER INFORMATION: asiRNA

<400> SEQUENCE: 244
gcuccagaaa cauacg                                                        16

<210> SEQ ID NO 245
<211> LENGTH: 16
<212> TYPE: RNA
<213> ORGANISM: Artificial Sequence
<220> FEATURE:
<223> OTHER INFORMATION: asiRNA

<400> SEQUENCE: 245
cauagguucu accuca                                                        16

<210> SEQ ID NO 246
<211> LENGTH: 16
<212> TYPE: RNA
<213> ORGANISM: Artificial Sequence
<220> FEATURE:
<223> OTHER INFORMATION: asiRNA

<400> SEQUENCE: 246
auagguucua ccucaa                                                        16

<210> SEQ ID NO 247
<211> LENGTH: 16
<212> TYPE: RNA
<213> ORGANISM: Artificial Sequence
<220> FEATURE:
<223> OTHER INFORMATION: asiRNA

<400> SEQUENCE: 247
uagguucuac cucaag                                                        16

<210> SEQ ID NO 248
<211> LENGTH: 16
<212> TYPE: RNA
<213> ORGANISM: Artificial Sequence
<220> FEATURE:
<223> OTHER INFORMATION: asiRNA

<400> SEQUENCE: 248
agguucuacc ucaaga                                                        16
```

```
<210> SEQ ID NO 249
<211> LENGTH: 16
<212> TYPE: RNA
<213> ORGANISM: Artificial Sequence
<220> FEATURE:
<223> OTHER INFORMATION: asiRNA

<400> SEQUENCE: 249
gguucuaccu caagau                                                        16

<210> SEQ ID NO 250
<211> LENGTH: 16
<212> TYPE: RNA
<213> ORGANISM: Artificial Sequence
<220> FEATURE:
<223> OTHER INFORMATION: asiRNA

<400> SEQUENCE: 250
guucuaccuc aagaug                                                        16

<210> SEQ ID NO 251
<211> LENGTH: 16
<212> TYPE: RNA
<213> ORGANISM: Artificial Sequence
<220> FEATURE:
<223> OTHER INFORMATION: asiRNA

<400> SEQUENCE: 251
uucuaccuca agaugu                                                        16

<210> SEQ ID NO 252
<211> LENGTH: 16
<212> TYPE: RNA
<213> ORGANISM: Artificial Sequence
<220> FEATURE:
<223> OTHER INFORMATION: asiRNA

<400> SEQUENCE: 252
ucuaccucaa gauguu                                                        16

<210> SEQ ID NO 253
<211> LENGTH: 16
<212> TYPE: RNA
<213> ORGANISM: Artificial Sequence
<220> FEATURE:
<223> OTHER INFORMATION: asiRNA

<400> SEQUENCE: 253
caaaucucgg aaagcc                                                        16

<210> SEQ ID NO 254
<211> LENGTH: 16
<212> TYPE: RNA
<213> ORGANISM: Artificial Sequence
<220> FEATURE:
<223> OTHER INFORMATION: asiRNA

<400> SEQUENCE: 254
aaaucucgga aagccc                                                        16

<210> SEQ ID NO 255
<211> LENGTH: 16
<212> TYPE: RNA
<213> ORGANISM: Artificial Sequence
<220> FEATURE:
<223> OTHER INFORMATION: asiRNA
```

```
<400> SEQUENCE: 255
aaucucggaa agcccu                                                      16

<210> SEQ ID NO 256
<211> LENGTH: 16
<212> TYPE: RNA
<213> ORGANISM: Artificial Sequence
<220> FEATURE:
<223> OTHER INFORMATION: asiRNA

<400> SEQUENCE: 256
gcccuuauuc cauuca                                                      16

<210> SEQ ID NO 257
<211> LENGTH: 16
<212> TYPE: RNA
<213> ORGANISM: Artificial Sequence
<220> FEATURE:
<223> OTHER INFORMATION: asiRNA

<400> SEQUENCE: 257
cccuuauucc auucau                                                      16

<210> SEQ ID NO 258
<211> LENGTH: 16
<212> TYPE: RNA
<213> ORGANISM: Artificial Sequence
<220> FEATURE:
<223> OTHER INFORMATION: asiRNA

<400> SEQUENCE: 258
ccuuauucca uucauc                                                      16

<210> SEQ ID NO 259
<211> LENGTH: 16
<212> TYPE: RNA
<213> ORGANISM: Artificial Sequence
<220> FEATURE:
<223> OTHER INFORMATION: asiRNA

<400> SEQUENCE: 259
cuuauuccau ucaucu                                                      16

<210> SEQ ID NO 260
<211> LENGTH: 16
<212> TYPE: RNA
<213> ORGANISM: Artificial Sequence
<220> FEATURE:
<223> OTHER INFORMATION: asiRNA

<400> SEQUENCE: 260
uuauuccauu caucuu                                                      16

<210> SEQ ID NO 261
<211> LENGTH: 16
<212> TYPE: RNA
<213> ORGANISM: Artificial Sequence
<220> FEATURE:
<223> OTHER INFORMATION: asiRNA

<400> SEQUENCE: 261
uauuccauuc aucuuu                                                      16

<210> SEQ ID NO 262
```

```
<211> LENGTH: 16
<212> TYPE: RNA
<213> ORGANISM: Artificial Sequence
<220> FEATURE:
<223> OTHER INFORMATION: asiRNA

<400> SEQUENCE: 262
auuccauuca ucuuuu                                                        16

<210> SEQ ID NO 263
<211> LENGTH: 16
<212> TYPE: RNA
<213> ORGANISM: Artificial Sequence
<220> FEATURE:
<223> OTHER INFORMATION: asiRNA

<400> SEQUENCE: 263
uuccauucau cuuuua                                                        16

<210> SEQ ID NO 264
<211> LENGTH: 16
<212> TYPE: RNA
<213> ORGANISM: Artificial Sequence
<220> FEATURE:
<223> OTHER INFORMATION: asiRNA

<400> SEQUENCE: 264
uccauucauc uuuuaa                                                        16

<210> SEQ ID NO 265
<211> LENGTH: 16
<212> TYPE: RNA
<213> ORGANISM: Artificial Sequence
<220> FEATURE:
<223> OTHER INFORMATION: asiRNA

<400> SEQUENCE: 265
ucucacuuug uuuccu                                                        16

<210> SEQ ID NO 266
<211> LENGTH: 16
<212> TYPE: RNA
<213> ORGANISM: Artificial Sequence
<220> FEATURE:
<223> OTHER INFORMATION: asiRNA

<400> SEQUENCE: 266
uucucacuuu guuucc                                                        16

<210> SEQ ID NO 267
<211> LENGTH: 16
<212> TYPE: RNA
<213> ORGANISM: Artificial Sequence
<220> FEATURE:
<223> OTHER INFORMATION: asiRNA

<400> SEQUENCE: 267
uuucucacuu uguuuc                                                        16

<210> SEQ ID NO 268
<211> LENGTH: 16
<212> TYPE: RNA
<213> ORGANISM: Artificial Sequence
<220> FEATURE:
<223> OTHER INFORMATION: asiRNA

<400> SEQUENCE: 268
```
uuuucucacu uuguuu                                           16

<210> SEQ ID NO 269
<211> LENGTH: 16
<212> TYPE: RNA
<213> ORGANISM: Artificial Sequence
<220> FEATURE:
<223> OTHER INFORMATION: asiRNA

<400> SEQUENCE: 269
uuuuucucac uuuguu                                           16

<210> SEQ ID NO 270
<211> LENGTH: 16
<212> TYPE: RNA
<213> ORGANISM: Artificial Sequence
<220> FEATURE:
<223> OTHER INFORMATION: asiRNA

<400> SEQUENCE: 270
auuuuucuca cuuugu                                           16

<210> SEQ ID NO 271
<211> LENGTH: 16
<212> TYPE: RNA
<213> ORGANISM: Artificial Sequence
<220> FEATURE:
<223> OTHER INFORMATION: asiRNA

<400> SEQUENCE: 271
uggcaggcag cgccac                                           16

<210> SEQ ID NO 272
<211> LENGTH: 16
<212> TYPE: RNA
<213> ORGANISM: Artificial Sequence
<220> FEATURE:
<223> OTHER INFORMATION: asiRNA

<400> SEQUENCE: 272
cuggcaggca gcgcca                                           16

<210> SEQ ID NO 273
<211> LENGTH: 16
<212> TYPE: RNA
<213> ORGANISM: Artificial Sequence
<220> FEATURE:
<223> OTHER INFORMATION: asiRNA

<400> SEQUENCE: 273
ggcaggcagc gccacu                                           16

<210> SEQ ID NO 274
<211> LENGTH: 16
<212> TYPE: RNA
<213> ORGANISM: Artificial Sequence
<220> FEATURE:
<223> OTHER INFORMATION: asiRNA

<400> SEQUENCE: 274
ugccagcccg cgccgc                                           16

<210> SEQ ID NO 275
<211> LENGTH: 16
<212> TYPE: RNA

```
<213> ORGANISM: Artificial Sequence
<220> FEATURE:
<223> OTHER INFORMATION: asiRNA

<400> SEQUENCE: 275
uuacuuccac aggaca                                                    16

<210> SEQ ID NO 276
<211> LENGTH: 16
<212> TYPE: RNA
<213> ORGANISM: Artificial Sequence
<220> FEATURE:
<223> OTHER INFORMATION: asiRNA

<400> SEQUENCE: 276
guggaaguaa uguagg                                                    16

<210> SEQ ID NO 277
<211> LENGTH: 16
<212> TYPE: RNA
<213> ORGANISM: Artificial Sequence
<220> FEATURE:
<223> OTHER INFORMATION: asiRNA

<400> SEQUENCE: 277
cccugauggg ugguac                                                    16

<210> SEQ ID NO 278
<211> LENGTH: 16
<212> TYPE: RNA
<213> ORGANISM: Artificial Sequence
<220> FEATURE:
<223> OTHER INFORMATION: asiRNA

<400> SEQUENCE: 278
ccugaugggu gguaca                                                    16

<210> SEQ ID NO 279
<211> LENGTH: 16
<212> TYPE: RNA
<213> ORGANISM: Artificial Sequence
<220> FEATURE:
<223> OTHER INFORMATION: asiRNA

<400> SEQUENCE: 279
cugaugggug guacac                                                    16

<210> SEQ ID NO 280
<211> LENGTH: 16
<212> TYPE: RNA
<213> ORGANISM: Artificial Sequence
<220> FEATURE:
<223> OTHER INFORMATION: asiRNA

<400> SEQUENCE: 280 ugauggugg uacaca                                                     16

<210> SEQ ID NO 281
<211> LENGTH: 16
<212> TYPE: RNA
<213> ORGANISM: Artificial Sequence
<220> FEATURE:
<223> OTHER INFORMATION: asiRNA

<400> SEQUENCE: 281
gauggguggu acacag                                                    16
```

```
<210> SEQ ID NO 282
<211> LENGTH: 16
<212> TYPE: RNA
<213> ORGANISM: Artificial Sequence
<220> FEATURE:
<223> OTHER INFORMATION: asiRNA

<400> SEQUENCE: 282 augggguggua cacaga                                                        16

<210> SEQ ID NO 283
<211> LENGTH: 16
<212> TYPE: RNA
<213> ORGANISM: Artificial Sequence
<220> FEATURE:
<223> OTHER INFORMATION: asiRNA

<400> SEQUENCE: 283
ugggugguac acagac                                                         16

<210> SEQ ID NO 284
<211> LENGTH: 16
<212> TYPE: RNA
<213> ORGANISM: Artificial Sequence
<220> FEATURE:
<223> OTHER INFORMATION: asiRNA

<400> SEQUENCE: 284 ggguggguaca cagaca                                                        16

<210> SEQ ID NO 285
<211> LENGTH: 16
<212> TYPE: RNA
<213> ORGANISM: Artificial Sequence
<220> FEATURE:
<223> OTHER INFORMATION: asiRNA

<400> SEQUENCE: 285
ggugguacac agacau                                                         16

<210> SEQ ID NO 286
<211> LENGTH: 16
<212> TYPE: RNA
<213> ORGANISM: Artificial Sequence
<220> FEATURE:
<223> OTHER INFORMATION: asiRNA

<400> SEQUENCE: 286
gacauacggu uuagcu                                                         16

<210> SEQ ID NO 287
<211> LENGTH: 16
<212> TYPE: RNA
<213> ORGANISM: Artificial Sequence
<220> FEATURE:
<223> OTHER INFORMATION: asiRNA

<400> SEQUENCE: 287
cuuggguguc uucuua                                                         16

<210> SEQ ID NO 288
<211> LENGTH: 16
<212> TYPE: RNA
<213> ORGANISM: Artificial Sequence
<220> FEATURE:
```

```
<223> OTHER INFORMATION: asiRNA

<400> SEQUENCE: 288
gcuugggugu cuucuu                                                    16

<210> SEQ ID NO 289
<211> LENGTH: 16
<212> TYPE: RNA
<213> ORGANISM: Artificial Sequence
<220> FEATURE:
<223> OTHER INFORMATION: asiRNA

<400> SEQUENCE: 289
agcuugggug ucuucu                                                    16

<210> SEQ ID NO 290
<211> LENGTH: 16
<212> TYPE: RNA
<213> ORGANISM: Artificial Sequence
<220> FEATURE:
<223> OTHER INFORMATION: asiRNA

<400> SEQUENCE: 290
uagcuugggu gucuuc                                                    16

<210> SEQ ID NO 291
<211> LENGTH: 16
<212> TYPE: RNA
<213> ORGANISM: Artificial Sequence
<220> FEATURE:
<223> OTHER INFORMATION: asiRNA

<400> SEQUENCE: 291
gccagcucag gaagcc                                                    16

<210> SEQ ID NO 292
<211> LENGTH: 16
<212> TYPE: RNA
<213> ORGANISM: Artificial Sequence
<220> FEATURE:
<223> OTHER INFORMATION: asiRNA

<400> SEQUENCE: 292
cgccagcuca ggaagc                                                    16

<210> SEQ ID NO 293
<211> LENGTH: 16
<212> TYPE: RNA
<213> ORGANISM: Artificial Sequence
<220> FEATURE:
<223> OTHER INFORMATION: asiRNA

<400> SEQUENCE: 293
gcgccagcuc aggaag                                                    16

<210> SEQ ID NO 294
<211> LENGTH: 16
<212> TYPE: RNA
<213> ORGANISM: Artificial Sequence
<220> FEATURE:
<223> OTHER INFORMATION: asiRNA

<400> SEQUENCE: 294
uggagccaau uuccuc                                                    16
```

```
<210> SEQ ID NO 295
<211> LENGTH: 16
<212> TYPE: RNA
<213> ORGANISM: Artificial Sequence
<220> FEATURE:
<223> OTHER INFORMATION: asiRNA

<400> SEQUENCE: 295
cucacuuugu uuccuu                                                     16

<210> SEQ ID NO 296
<211> LENGTH: 16
<212> TYPE: RNA
<213> ORGANISM: Artificial Sequence
<220> FEATURE:
<223> OTHER INFORMATION: asiRNA

<400> SEQUENCE: 296 cauuuucuc acuuug                                                      16

<210> SEQ ID NO 297
<211> LENGTH: 16
<212> TYPE: RNA
<213> ORGANISM: Artificial Sequence
<220> FEATURE:
<223> OTHER INFORMATION: asiRNA

<400> SEQUENCE: 297
ccauagguuc uaccuc                                                     16

<210> SEQ ID NO 298
<211> LENGTH: 16
<212> TYPE: RNA
<213> ORGANISM: Artificial Sequence
<220> FEATURE:
<223> OTHER INFORMATION: asiRNA

<400> SEQUENCE: 298
accauagguu cuaccu                                                     16

<210> SEQ ID NO 299
<211> LENGTH: 16
<212> TYPE: RNA
<213> ORGANISM: Artificial Sequence
<220> FEATURE:
<223> OTHER INFORMATION: asiRNA

<400> SEQUENCE: 299
caccauaggu ucuacc                                                     16

<210> SEQ ID NO 300
<211> LENGTH: 16
<212> TYPE: RNA
<213> ORGANISM: Artificial Sequence
<220> FEATURE:
<223> OTHER INFORMATION: asiRNA

<400> SEQUENCE: 300
ccaccauagg uucuac                                                     16

<210> SEQ ID NO 301
<211> LENGTH: 16
<212> TYPE: RNA
<213> ORGANISM: Artificial Sequence
<220> FEATURE:
<223> OTHER INFORMATION: asiRNA
```

```
<400> SEQUENCE: 301
accaccauag guucua                                               16

<210> SEQ ID NO 302
<211> LENGTH: 16
<212> TYPE: RNA
<213> ORGANISM: Artificial Sequence
<220> FEATURE:
<223> OTHER INFORMATION: asiRNA

<400> SEQUENCE: 302
caccaccaua gguucu                                               16

<210> SEQ ID NO 303
<211> LENGTH: 16
<212> TYPE: RNA
<213> ORGANISM: Artificial Sequence
<220> FEATURE:
<223> OTHER INFORMATION: asiRNA

<400> SEQUENCE: 303
ggacuacccc aaaucu                                               16

<210> SEQ ID NO 304
<211> LENGTH: 16
<212> TYPE: RNA
<213> ORGANISM: Artificial Sequence
<220> FEATURE:
<223> OTHER INFORMATION: asiRNA

<400> SEQUENCE: 304
aggacuaccc caaauc                                               16

<210> SEQ ID NO 305
<211> LENGTH: 16
<212> TYPE: RNA
<213> ORGANISM: Artificial Sequence
<220> FEATURE:
<223> OTHER INFORMATION: asiRNA

<400> SEQUENCE: 305
gaggacuacc ccaaau                                               16

<210> SEQ ID NO 306
<211> LENGTH: 16
<212> TYPE: RNA
<213> ORGANISM: Artificial Sequence
<220> FEATURE:
<223> OTHER INFORMATION: asiRNA

<400> SEQUENCE: 306
ugaggacuac cccaaa                                               16

<210> SEQ ID NO 307
<211> LENGTH: 16
<212> TYPE: RNA
<213> ORGANISM: Artificial Sequence
<220> FEATURE:
<223> OTHER INFORMATION: asiRNA

<400> SEQUENCE: 307
uugaggacua ccccaa                                               16

<210> SEQ ID NO 308
<211> LENGTH: 16
```

<212> TYPE: RNA
<213> ORGANISM: Artificial Sequence
<220> FEATURE:
<223> OTHER INFORMATION: asiRNA

<400> SEQUENCE: 308
uuugaggacu acccca                                                    16

<210> SEQ ID NO 309
<211> LENGTH: 16
<212> TYPE: RNA
<213> ORGANISM: Artificial Sequence
<220> FEATURE:
<223> OTHER INFORMATION: asiRNA

<400> SEQUENCE: 309
ccaaaucucg gaaagc                                                    16

<210> SEQ ID NO 310
<211> LENGTH: 16
<212> TYPE: RNA
<213> ORGANISM: Artificial Sequence
<220> FEATURE:
<223> OTHER INFORMATION: asiRNA

<400> SEQUENCE: 310
agcccuuauu ccauuc                                                    16

<210> SEQ ID NO 311
<211> LENGTH: 16
<212> TYPE: RNA
<213> ORGANISM: Artificial Sequence
<220> FEATURE:
<223> OTHER INFORMATION: asiRNA

<400> SEQUENCE: 311
aagcccuuau uccauu                                                    16

<210> SEQ ID NO 312
<211> LENGTH: 16
<212> TYPE: RNA
<213> ORGANISM: Artificial Sequence
<220> FEATURE:
<223> OTHER INFORMATION: asiRNA

<400> SEQUENCE: 312
ggcuaugccc uggcca                                                    16

<210> SEQ ID NO 313
<211> LENGTH: 21
<212> TYPE: RNA
<213> ORGANISM: Artificial Sequence
<220> FEATURE:
<223> OTHER INFORMATION: asiRNA

<400> SEQUENCE: 313
cagcuccugc aggaaccagg c                                              21

<210> SEQ ID NO 314
<211> LENGTH: 21
<212> TYPE: RNA
<213> ORGANISM: Artificial Sequence
<220> FEATURE:
<223> OTHER INFORMATION: asiRNA

<400> SEQUENCE: 314
gcagcuccug caggaaccag g 21

<210> SEQ ID NO 315
<211> LENGTH: 21
<212> TYPE: RNA
<213> ORGANISM: Artificial Sequence
<220> FEATURE:
<223> OTHER INFORMATION: asiRNA

<400> SEQUENCE: 315
ggcagcuccu gcaggaacca g 21

<210> SEQ ID NO 316
<211> LENGTH: 21
<212> TYPE: RNA
<213> ORGANISM: Artificial Sequence
<220> FEATURE:
<223> OTHER INFORMATION: asiRNA

<400> SEQUENCE: 316
aggcagcucc ugcaggaacc a 21

<210> SEQ ID NO 317
<211> LENGTH: 21
<212> TYPE: RNA
<213> ORGANISM: Artificial Sequence
<220> FEATURE:
<223> OTHER INFORMATION: asiRNA

<400> SEQUENCE: 317
aaggcagcuc cugcaggaac c 21

<210> SEQ ID NO 318
<211> LENGTH: 21
<212> TYPE: RNA
<213> ORGANISM: Artificial Sequence
<220> FEATURE:
<223> OTHER INFORMATION: asiRNA

<400> SEQUENCE: 318
gaaggcagcu ccugcaggaa c 21

<210> SEQ ID NO 319
<211> LENGTH: 21
<212> TYPE: RNA
<213> ORGANISM: Artificial Sequence
<220> FEATURE:
<223> OTHER INFORMATION: asiRNA

<400> SEQUENCE: 319
ggaaggcagc uccugcagga a 21

<210> SEQ ID NO 320
<211> LENGTH: 21
<212> TYPE: RNA
<213> ORGANISM: Artificial Sequence
<220> FEATURE:
<223> OTHER INFORMATION: asiRNA

<400> SEQUENCE: 320
aggaaggcag cuccugcagg a 21

<210> SEQ ID NO 321
<211> LENGTH: 21
<212> TYPE: RNA
<213> ORGANISM: Artificial Sequence

```
<220> FEATURE:
<223> OTHER INFORMATION: asiRNA

<400> SEQUENCE: 321
aaggaaggca gcuccugcag g                                              21

<210> SEQ ID NO 322
<211> LENGTH: 21
<212> TYPE: RNA
<213> ORGANISM: Artificial Sequence
<220> FEATURE:
<223> OTHER INFORMATION: asiRNA

<400> SEQUENCE: 322
aauguccugu ggaaguaaug u                                              21

<210> SEQ ID NO 323
<211> LENGTH: 21
<212> TYPE: RNA
<213> ORGANISM: Artificial Sequence
<220> FEATURE:
<223> OTHER INFORMATION: asiRNA

<400> SEQUENCE: 323
aaauguccug uggaaguaau g                                              21

<210> SEQ ID NO 324
<211> LENGTH: 21
<212> TYPE: RNA
<213> ORGANISM: Artificial Sequence
<220> FEATURE:
<223> OTHER INFORMATION: asiRNA

<400> SEQUENCE: 324
cguaaacaag ccaccuugug g                                              21

<210> SEQ ID NO 325
<211> LENGTH: 21
<212> TYPE: RNA
<213> ORGANISM: Artificial Sequence
<220> FEATURE:
<223> OTHER INFORMATION: asiRNA

<400> SEQUENCE: 325
acguaaacaa gccaccuugu g                                              21

<210> SEQ ID NO 326
<211> LENGTH: 21
<212> TYPE: RNA
<213> ORGANISM: Artificial Sequence
<220> FEATURE:
<223> OTHER INFORMATION: asiRNA

<400> SEQUENCE: 326
uacguaaaca agccaccuug u                                              21

<210> SEQ ID NO 327
<211> LENGTH: 21
<212> TYPE: RNA
<213> ORGANISM: Artificial Sequence
<220> FEATURE:
<223> OTHER INFORMATION: asiRNA

<400> SEQUENCE: 327
auacguaaac aagccaccuu g                                              21
```

<210> SEQ ID NO 328
<211> LENGTH: 21
<212> TYPE: RNA
<213> ORGANISM: Artificial Sequence
<220> FEATURE:
<223> OTHER INFORMATION: asiRNA

<400> SEQUENCE: 328
cauacguaaa caagccaccu u                                              21

<210> SEQ ID NO 329
<211> LENGTH: 21
<212> TYPE: RNA
<213> ORGANISM: Artificial Sequence
<220> FEATURE:
<223> OTHER INFORMATION: asiRNA

<400> SEQUENCE: 329
acauacguaa acaagccacc u                                              21

<210> SEQ ID NO 330
<211> LENGTH: 21
<212> TYPE: RNA
<213> ORGANISM: Artificial Sequence
<220> FEATURE:
<223> OTHER INFORMATION: asiRNA

<400> SEQUENCE: 330
aaacaucuug agguagaacc u                                              21

<210> SEQ ID NO 331
<211> LENGTH: 21
<212> TYPE: RNA
<213> ORGANISM: Artificial Sequence
<220> FEATURE:
<223> OTHER INFORMATION: asiRNA

<400> SEQUENCE: 331
agcuccugca ggaaccaggc g                                              21

<210> SEQ ID NO 332
<211> LENGTH: 21
<212> TYPE: RNA
<213> ORGANISM: Artificial Sequence
<220> FEATURE:
<223> OTHER INFORMATION: asiRNA

<400> SEQUENCE: 332
auguccugug gaaguaaugu a                                              21

<210> SEQ ID NO 333
<211> LENGTH: 21
<212> TYPE: RNA
<213> ORGANISM: Artificial Sequence
<220> FEATURE:
<223> OTHER INFORMATION: asiRNA

<400> SEQUENCE: 333
gcuaaaccgu augucugugu a                                              21

<210> SEQ ID NO 334
<211> LENGTH: 21
<212> TYPE: RNA
<213> ORGANISM: Artificial Sequence
<220> FEATURE:
<223> OTHER INFORMATION: asiRNA

```
<400> SEQUENCE: 334
cuaaaccgua ugucugugua c                                             21

<210> SEQ ID NO 335
<211> LENGTH: 21
<212> TYPE: RNA
<213> ORGANISM: Artificial Sequence
<220> FEATURE:
<223> OTHER INFORMATION: asiRNA

<400> SEQUENCE: 335
uaaaccguau gucuguguac c                                             21

<210> SEQ ID NO 336
<211> LENGTH: 21
<212> TYPE: RNA
<213> ORGANISM: Artificial Sequence
<220> FEATURE:
<223> OTHER INFORMATION: asiRNA

<400> SEQUENCE: 336
aaaccguaug ucuguguacc a                                             21

<210> SEQ ID NO 337
<211> LENGTH: 21
<212> TYPE: RNA
<213> ORGANISM: Artificial Sequence
<220> FEATURE:
<223> OTHER INFORMATION: asiRNA

<400> SEQUENCE: 337
ccaccuugug gaauccugua g                                             21

<210> SEQ ID NO 338
<211> LENGTH: 21
<212> TYPE: RNA
<213> ORGANISM: Artificial Sequence
<220> FEATURE:
<223> OTHER INFORMATION: asiRNA

<400> SEQUENCE: 338
gccaccuugu ggaauccugu a                                             21

<210> SEQ ID NO 339
<211> LENGTH: 21
<212> TYPE: RNA
<213> ORGANISM: Artificial Sequence
<220> FEATURE:
<223> OTHER INFORMATION: asiRNA

<400> SEQUENCE: 339
agccaccuug uggaauccug u                                             21

<210> SEQ ID NO 340
<211> LENGTH: 21
<212> TYPE: RNA
<213> ORGANISM: Artificial Sequence
<220> FEATURE:
<223> OTHER INFORMATION: asiRNA

<400> SEQUENCE: 340
aagccaccuu guggaauccu g                                             21

<210> SEQ ID NO 341
```

```
<211> LENGTH: 21
<212> TYPE: RNA
<213> ORGANISM: Artificial Sequence
<220> FEATURE:
<223> OTHER INFORMATION: asiRNA

<400> SEQUENCE: 341
caagccaccu uguggaaucc u                                              21

<210> SEQ ID NO 342
<211> LENGTH: 21
<212> TYPE: RNA
<213> ORGANISM: Artificial Sequence
<220> FEATURE:
<223> OTHER INFORMATION: asiRNA

<400> SEQUENCE: 342
acaagccacc uuguggaauc c                                              21

<210> SEQ ID NO 343
<211> LENGTH: 21
<212> TYPE: RNA
<213> ORGANISM: Artificial Sequence
<220> FEATURE:
<223> OTHER INFORMATION: asiRNA

<400> SEQUENCE: 343
aacaagccac cuuguggaau c                                              21

<210> SEQ ID NO 344
<211> LENGTH: 21
<212> TYPE: RNA
<213> ORGANISM: Artificial Sequence
<220> FEATURE:
<223> OTHER INFORMATION: asiRNA

<400> SEQUENCE: 344
aaacaagcca ccuuguggaa u                                              21

<210> SEQ ID NO 345
<211> LENGTH: 21
<212> TYPE: RNA
<213> ORGANISM: Artificial Sequence
<220> FEATURE:
<223> OTHER INFORMATION: asiRNA

<400> SEQUENCE: 345
uaaacaagcc accuugugga a                                              21

<210> SEQ ID NO 346
<211> LENGTH: 21
<212> TYPE: RNA
<213> ORGANISM: Artificial Sequence
<220> FEATURE:
<223> OTHER INFORMATION: asiRNA

<400> SEQUENCE: 346
guaaacaagc caccuugugg a                                              21

<210> SEQ ID NO 347
<211> LENGTH: 21
<212> TYPE: RNA
<213> ORGANISM: Artificial Sequence
<220> FEATURE:
<223> OTHER INFORMATION: asiRNA

<400> SEQUENCE: 347
```

```
aggaaauugg cuccagaaac a                                              21

<210> SEQ ID NO 348
<211> LENGTH: 21
<212> TYPE: RNA
<213> ORGANISM: Artificial Sequence
<220> FEATURE:
<223> OTHER INFORMATION: asiRNA

<400> SEQUENCE: 348
ggaaauuggc uccagaaaca u                                              21

<210> SEQ ID NO 349
<211> LENGTH: 21
<212> TYPE: RNA
<213> ORGANISM: Artificial Sequence
<220> FEATURE:
<223> OTHER INFORMATION: asiRNA

<400> SEQUENCE: 349
gaaauuggcu ccagaaacau a                                              21

<210> SEQ ID NO 350
<211> LENGTH: 21
<212> TYPE: RNA
<213> ORGANISM: Artificial Sequence
<220> FEATURE:
<223> OTHER INFORMATION: asiRNA

<400> SEQUENCE: 350
aaauuggcuc cagaaacaua c                                              21

<210> SEQ ID NO 351
<211> LENGTH: 21
<212> TYPE: RNA
<213> ORGANISM: Artificial Sequence
<220> FEATURE:
<223> OTHER INFORMATION: asiRNA

<400> SEQUENCE: 351
aauuggcucc agaaacauac g                                              21

<210> SEQ ID NO 352
<211> LENGTH: 21
<212> TYPE: RNA
<213> ORGANISM: Artificial Sequence
<220> FEATURE:
<223> OTHER INFORMATION: asiRNA

<400> SEQUENCE: 352
auuggcucca gaaacauacg u                                              21

<210> SEQ ID NO 353
<211> LENGTH: 21
<212> TYPE: RNA
<213> ORGANISM: Artificial Sequence
<220> FEATURE:
<223> OTHER INFORMATION: asiRNA

<400> SEQUENCE: 353
uuggcuccag aaacauacgu a                                              21

<210> SEQ ID NO 354
<211> LENGTH: 21
<212> TYPE: RNA
```

```
<213> ORGANISM: Artificial Sequence
<220> FEATURE:
<223> OTHER INFORMATION: asiRNA

<400> SEQUENCE: 354
uggcuccaga aacauacgua a                                              21

<210> SEQ ID NO 355
<211> LENGTH: 21
<212> TYPE: RNA
<213> ORGANISM: Artificial Sequence
<220> FEATURE:
<223> OTHER INFORMATION: asiRNA

<400> SEQUENCE: 355
ggcuccagaa acauacguaa a                                              21

<210> SEQ ID NO 356
<211> LENGTH: 21
<212> TYPE: RNA
<213> ORGANISM: Artificial Sequence
<220> FEATURE:
<223> OTHER INFORMATION: asiRNA

<400> SEQUENCE: 356
gcuccagaaa cauacguaaa c                                              21

<210> SEQ ID NO 357
<211> LENGTH: 21
<212> TYPE: RNA
<213> ORGANISM: Artificial Sequence
<220> FEATURE:
<223> OTHER INFORMATION: asiRNA

<400> SEQUENCE: 357
ugagguagaa ccuauggugg u                                              21

<210> SEQ ID NO 358
<211> LENGTH: 21
<212> TYPE: RNA
<213> ORGANISM: Artificial Sequence
<220> FEATURE:
<223> OTHER INFORMATION: asiRNA

<400> SEQUENCE: 358
uugagguaga accuauggug g                                              21

<210> SEQ ID NO 359
<211> LENGTH: 21
<212> TYPE: RNA
<213> ORGANISM: Artificial Sequence
<220> FEATURE:
<223> OTHER INFORMATION: asiRNA

<400> SEQUENCE: 359
cuugagguag aaccuauggu g                                              21

<210> SEQ ID NO 360
<211> LENGTH: 21
<212> TYPE: RNA
<213> ORGANISM: Artificial Sequence
<220> FEATURE:
<223> OTHER INFORMATION: asiRNA

<400> SEQUENCE: 360
ucuugaggua gaaccuaugg u                                              21
```

<210> SEQ ID NO 361
<211> LENGTH: 21
<212> TYPE: RNA
<213> ORGANISM: Artificial Sequence
<220> FEATURE:
<223> OTHER INFORMATION: asiRNA

<400> SEQUENCE: 361
aucuugaggu agaaccuaug g                                              21

<210> SEQ ID NO 362
<211> LENGTH: 21
<212> TYPE: RNA
<213> ORGANISM: Artificial Sequence
<220> FEATURE:
<223> OTHER INFORMATION: asiRNA

<400> SEQUENCE: 362
caucuugagg uagaaccuau g                                              21

<210> SEQ ID NO 363
<211> LENGTH: 21
<212> TYPE: RNA
<213> ORGANISM: Artificial Sequence
<220> FEATURE:
<223> OTHER INFORMATION: asiRNA

<400> SEQUENCE: 363
acaucuugag guagaaccua u                                              21

<210> SEQ ID NO 364
<211> LENGTH: 21
<212> TYPE: RNA
<213> ORGANISM: Artificial Sequence
<220> FEATURE:
<223> OTHER INFORMATION: asiRNA

<400> SEQUENCE: 364
aacaucuuga gguagaaccu a                                              21

<210> SEQ ID NO 365
<211> LENGTH: 21
<212> TYPE: RNA
<213> ORGANISM: Artificial Sequence
<220> FEATURE:
<223> OTHER INFORMATION: asiRNA

<400> SEQUENCE: 365
ggcuuuccga gauuuggggu a                                              21

<210> SEQ ID NO 366
<211> LENGTH: 21
<212> TYPE: RNA
<213> ORGANISM: Artificial Sequence
<220> FEATURE:
<223> OTHER INFORMATION: asiRNA

<400> SEQUENCE: 366
gggcuuuccg agauuugggg u                                              21

<210> SEQ ID NO 367
<211> LENGTH: 21
<212> TYPE: RNA
<213> ORGANISM: Artificial Sequence
<220> FEATURE:

```
<223> OTHER INFORMATION: asiRNA

<400> SEQUENCE: 367
agggcuuucc gagauuuggg g                                               21

<210> SEQ ID NO 368
<211> LENGTH: 21
<212> TYPE: RNA
<213> ORGANISM: Artificial Sequence
<220> FEATURE:
<223> OTHER INFORMATION: asiRNA

<400> SEQUENCE: 368
ugaauggaau aagggcuuuc c                                               21

<210> SEQ ID NO 369
<211> LENGTH: 21
<212> TYPE: RNA
<213> ORGANISM: Artificial Sequence
<220> FEATURE:
<223> OTHER INFORMATION: asiRNA

<400> SEQUENCE: 369
augaauggaa uaagggcuuu c                                               21

<210> SEQ ID NO 370
<211> LENGTH: 21
<212> TYPE: RNA
<213> ORGANISM: Artificial Sequence
<220> FEATURE:
<223> OTHER INFORMATION: asiRNA

<400> SEQUENCE: 370
gaugaaugga auaagggcuu u                                               21

<210> SEQ ID NO 371
<211> LENGTH: 21
<212> TYPE: RNA
<213> ORGANISM: Artificial Sequence
<220> FEATURE:
<223> OTHER INFORMATION: asiRNA

<400> SEQUENCE: 371
agaugaaugg aauaagggcu u                                               21

<210> SEQ ID NO 372
<211> LENGTH: 21
<212> TYPE: RNA
<213> ORGANISM: Artificial Sequence
<220> FEATURE:
<223> OTHER INFORMATION: asiRNA

<400> SEQUENCE: 372
aagaugaaug gaauaagggc u                                               21

<210> SEQ ID NO 373
<211> LENGTH: 21
<212> TYPE: RNA
<213> ORGANISM: Artificial Sequence
<220> FEATURE:
<223> OTHER INFORMATION: asiRNA

<400> SEQUENCE: 373
aaagaugaau ggaauaaggg c                                               21
```

```
<210> SEQ ID NO 374
<211> LENGTH: 21
<212> TYPE: RNA
<213> ORGANISM: Artificial Sequence
<220> FEATURE:
<223> OTHER INFORMATION: asiRNA

<400> SEQUENCE: 374
aaaagaugaa uggaauaagg g                                         21

<210> SEQ ID NO 375
<211> LENGTH: 21
<212> TYPE: RNA
<213> ORGANISM: Artificial Sequence
<220> FEATURE:
<223> OTHER INFORMATION: asiRNA

<400> SEQUENCE: 375
uaaaagauga auggaauaag g                                         21

<210> SEQ ID NO 376
<211> LENGTH: 21
<212> TYPE: RNA
<213> ORGANISM: Artificial Sequence
<220> FEATURE:
<223> OTHER INFORMATION: asiRNA

<400> SEQUENCE: 376
uuaaaagaug aauggaauaa g                                         21

<210> SEQ ID NO 377
<211> LENGTH: 21
<212> TYPE: RNA
<213> ORGANISM: Artificial Sequence
<220> FEATURE:
<223> OTHER INFORMATION: asiRNA

<400> SEQUENCE: 377
aggaaacaaa gugagaaaaa u                                         21

<210> SEQ ID NO 378
<211> LENGTH: 21
<212> TYPE: RNA
<213> ORGANISM: Artificial Sequence
<220> FEATURE:
<223> OTHER INFORMATION: asiRNA

<400> SEQUENCE: 378
ggaaacaaag ugagaaaaau g                                         21

<210> SEQ ID NO 379
<211> LENGTH: 21
<212> TYPE: RNA
<213> ORGANISM: Artificial Sequence
<220> FEATURE:
<223> OTHER INFORMATION: asiRNA

<400> SEQUENCE: 379
gaaacaaagu gagaaaaaug c                                         21

<210> SEQ ID NO 380
<211> LENGTH: 21
<212> TYPE: RNA
<213> ORGANISM: Artificial Sequence
<220> FEATURE:
<223> OTHER INFORMATION: asiRNA
```

<400> SEQUENCE: 380
aaacaaagug agaaaaaugc a                                              21

<210> SEQ ID NO 381
<211> LENGTH: 21
<212> TYPE: RNA
<213> ORGANISM: Artificial Sequence
<220> FEATURE:
<223> OTHER INFORMATION: asiRNA

<400> SEQUENCE: 381
aacaaaguga gaaaaaugca a                                              21

<210> SEQ ID NO 382
<211> LENGTH: 21
<212> TYPE: RNA
<213> ORGANISM: Artificial Sequence
<220> FEATURE:
<223> OTHER INFORMATION: asiRNA

<400> SEQUENCE: 382
acaaagugag aaaaaugcaa a                                              21

<210> SEQ ID NO 383
<211> LENGTH: 21
<212> TYPE: RNA
<213> ORGANISM: Artificial Sequence
<220> FEATURE:
<223> OTHER INFORMATION: asiRNA

<400> SEQUENCE: 383
guggcgcugc cugccagcac u                                              21

<210> SEQ ID NO 384
<211> LENGTH: 21
<212> TYPE: RNA
<213> ORGANISM: Artificial Sequence
<220> FEATURE:
<223> OTHER INFORMATION: asiRNA

<400> SEQUENCE: 384
uggcgcugcc ugccagcacu g                                              21

<210> SEQ ID NO 385
<211> LENGTH: 21
<212> TYPE: RNA
<213> ORGANISM: Artificial Sequence
<220> FEATURE:
<223> OTHER INFORMATION: asiRNA

<400> SEQUENCE: 385
aguggcgcug ccugccagca c                                              21

<210> SEQ ID NO 386
<211> LENGTH: 21
<212> TYPE: RNA
<213> ORGANISM: Artificial Sequence
<220> FEATURE:
<223> OTHER INFORMATION: asiRNA

<400> SEQUENCE: 386
gcggcgcggg cuggcaggcg g                                              21

<210> SEQ ID NO 387
<211> LENGTH: 21

```
<212> TYPE: RNA
<213> ORGANISM: Artificial Sequence
<220> FEATURE:
<223> OTHER INFORMATION: asiRNA

<400> SEQUENCE: 387
uguccugugg aaguaaugua g                                              21

<210> SEQ ID NO 388
<211> LENGTH: 21
<212> TYPE: RNA
<213> ORGANISM: Artificial Sequence
<220> FEATURE:
<223> OTHER INFORMATION: asiRNA

<400> SEQUENCE: 388
ccuacauuac uuccacagga c                                              21

<210> SEQ ID NO 389
<211> LENGTH: 21
<212> TYPE: RNA
<213> ORGANISM: Artificial Sequence
<220> FEATURE:
<223> OTHER INFORMATION: asiRNA

<400> SEQUENCE: 389
guaccaccca ucaggguauu c                                              21

<210> SEQ ID NO 390
<211> LENGTH: 21
<212> TYPE: RNA
<213> ORGANISM: Artificial Sequence
<220> FEATURE:
<223> OTHER INFORMATION: asiRNA

<400> SEQUENCE: 390
uguaccaccc aucaggguau u                                              21

<210> SEQ ID NO 391
<211> LENGTH: 21
<212> TYPE: RNA
<213> ORGANISM: Artificial Sequence
<220> FEATURE:
<223> OTHER INFORMATION: asiRNA

<400> SEQUENCE: 391
guguaccacc caucagggua u                                              21

<210> SEQ ID NO 392
<211> LENGTH: 21
<212> TYPE: RNA
<213> ORGANISM: Artificial Sequence
<220> FEATURE:
<223> OTHER INFORMATION: asiRNA

<400> SEQUENCE: 392
uguguaccac ccaucagggu a                                              21

<210> SEQ ID NO 393
<211> LENGTH: 21
<212> TYPE: RNA
<213> ORGANISM: Artificial Sequence
<220> FEATURE:
<223> OTHER INFORMATION: asiRNA

<400> SEQUENCE: 393
```
cuguguacca cccaucaggg u                                              21

<210> SEQ ID NO 394
<211> LENGTH: 21
<212> TYPE: RNA
<213> ORGANISM: Artificial Sequence
<220> FEATURE:
<223> OTHER INFORMATION: asiRNA

<400> SEQUENCE: 394
ucuguguacc acccaucagg g                                              21

<210> SEQ ID NO 395
<211> LENGTH: 21
<212> TYPE: RNA
<213> ORGANISM: Artificial Sequence
<220> FEATURE:
<223> OTHER INFORMATION: asiRNA

<400> SEQUENCE: 395
gucuguguac cacccaucag g                                              21

<210> SEQ ID NO 396
<211> LENGTH: 21
<212> TYPE: RNA
<213> ORGANISM: Artificial Sequence
<220> FEATURE:
<223> OTHER INFORMATION: asiRNA

<400> SEQUENCE: 396
ugucugugua ccacccauca g                                              21

<210> SEQ ID NO 397
<211> LENGTH: 21
<212> TYPE: RNA
<213> ORGANISM: Artificial Sequence
<220> FEATURE:
<223> OTHER INFORMATION: asiRNA

<400> SEQUENCE: 397
augucugugu accacccauc a                                              21

<210> SEQ ID NO 398
<211> LENGTH: 21
<212> TYPE: RNA
<213> ORGANISM: Artificial Sequence
<220> FEATURE:
<223> OTHER INFORMATION: asiRNA

<400> SEQUENCE: 398
agcuaaaccg uaugucugug u                                              21

<210> SEQ ID NO 399
<211> LENGTH: 21
<212> TYPE: RNA
<213> ORGANISM: Artificial Sequence
<220> FEATURE:
<223> OTHER INFORMATION: asiRNA

<400> SEQUENCE: 399
uaagaagaca cccaagcuaa a                                              21

<210> SEQ ID NO 400
<211> LENGTH: 21
<212> TYPE: RNA
<213> ORGANISM: Artificial Sequence

```
<220> FEATURE:
<223> OTHER INFORMATION: asiRNA

<400> SEQUENCE: 400
aagaagacac ccaagcuaaa c                                              21

<210> SEQ ID NO 401
<211> LENGTH: 21
<212> TYPE: RNA
<213> ORGANISM: Artificial Sequence
<220> FEATURE:
<223> OTHER INFORMATION: asiRNA

<400> SEQUENCE: 401
agaagacacc caagcuaaac c                                              21

<210> SEQ ID NO 402
<211> LENGTH: 21
<212> TYPE: RNA
<213> ORGANISM: Artificial Sequence
<220> FEATURE:
<223> OTHER INFORMATION: asiRNA

<400> SEQUENCE: 402
gaagacaccc aagcuaaacc g                                              21

<210> SEQ ID NO 403
<211> LENGTH: 21
<212> TYPE: RNA
<213> ORGANISM: Artificial Sequence
<220> FEATURE:
<223> OTHER INFORMATION: asiRNA

<400> SEQUENCE: 403
ggcuuccuga gcuggcgcaa u                                              21

<210> SEQ ID NO 404
<211> LENGTH: 21
<212> TYPE: RNA
<213> ORGANISM: Artificial Sequence
<220> FEATURE:
<223> OTHER INFORMATION: asiRNA

<400> SEQUENCE: 404
gcuuccugag cuggcgcaau a                                              21

<210> SEQ ID NO 405
<211> LENGTH: 21
<212> TYPE: RNA
<213> ORGANISM: Artificial Sequence
<220> FEATURE:
<223> OTHER INFORMATION: asiRNA

<400> SEQUENCE: 405
cuuccugagc uggcgcaaua u                                              21

<210> SEQ ID NO 406
<211> LENGTH: 21
<212> TYPE: RNA
<213> ORGANISM: Artificial Sequence
<220> FEATURE:
<223> OTHER INFORMATION: asiRNA

<400> SEQUENCE: 406
gaggaaauug gcuccagaaa c                                              21
```

```
<210> SEQ ID NO 407
<211> LENGTH: 21
<212> TYPE: RNA
<213> ORGANISM: Artificial Sequence
<220> FEATURE:
<223> OTHER INFORMATION: asiRNA

<400> SEQUENCE: 407
aaggaaacaa agugagaaaa a                                              21

<210> SEQ ID NO 408
<211> LENGTH: 21
<212> TYPE: RNA
<213> ORGANISM: Artificial Sequence
<220> FEATURE:
<223> OTHER INFORMATION: asiRNA

<400> SEQUENCE: 408
caaagugaga aaaugcaaa u                                               21

<210> SEQ ID NO 409
<211> LENGTH: 21
<212> TYPE: RNA
<213> ORGANISM: Artificial Sequence
<220> FEATURE:
<223> OTHER INFORMATION: asiRNA

<400> SEQUENCE: 409
gagguagaac cuaugguggu g                                              21

<210> SEQ ID NO 410
<211> LENGTH: 21
<212> TYPE: RNA
<213> ORGANISM: Artificial Sequence
<220> FEATURE:
<223> OTHER INFORMATION: asiRNA

<400> SEQUENCE: 410
agguagaacc uaugguggug a                                              21

<210> SEQ ID NO 411
<211> LENGTH: 21
<212> TYPE: RNA
<213> ORGANISM: Artificial Sequence
<220> FEATURE:
<223> OTHER INFORMATION: asiRNA

<400> SEQUENCE: 411
gguagaaccu auggugguga a                                              21

<210> SEQ ID NO 412
<211> LENGTH: 21
<212> TYPE: RNA
<213> ORGANISM: Artificial Sequence
<220> FEATURE:
<223> OTHER INFORMATION: asiRNA

<400> SEQUENCE: 412
guagaaccua uggugguga a                                               21

<210> SEQ ID NO 413
<211> LENGTH: 21
<212> TYPE: RNA
<213> ORGANISM: Artificial Sequence
<220> FEATURE:
<223> OTHER INFORMATION: asiRNA
```

```
<400> SEQUENCE: 413
uagaaccuau gguggugaaa a                                            21

<210> SEQ ID NO 414
<211> LENGTH: 21
<212> TYPE: RNA
<213> ORGANISM: Artificial Sequence
<220> FEATURE:
<223> OTHER INFORMATION: asiRNA

<400> SEQUENCE: 414
agaaccuaug guggugaaaa g                                            21

<210> SEQ ID NO 415
<211> LENGTH: 21
<212> TYPE: RNA
<213> ORGANISM: Artificial Sequence
<220> FEATURE:
<223> OTHER INFORMATION: asiRNA

<400> SEQUENCE: 415
agauuugggg uaguccucaa a                                            21

<210> SEQ ID NO 416
<211> LENGTH: 21
<212> TYPE: RNA
<213> ORGANISM: Artificial Sequence
<220> FEATURE:
<223> OTHER INFORMATION: asiRNA

<400> SEQUENCE: 416
gauuuggggu aguccucaaa c                                            21

<210> SEQ ID NO 417
<211> LENGTH: 21
<212> TYPE: RNA
<213> ORGANISM: Artificial Sequence
<220> FEATURE:
<223> OTHER INFORMATION: asiRNA

<400> SEQUENCE: 417
auuugggguA guccucaaac a                                            21

<210> SEQ ID NO 418
<211> LENGTH: 21
<212> TYPE: RNA
<213> ORGANISM: Artificial Sequence
<220> FEATURE:
<223> OTHER INFORMATION: asiRNA

<400> SEQUENCE: 418
uuuggggUAG uccucaaaca u                                            21

<210> SEQ ID NO 419
<211> LENGTH: 21
<212> TYPE: RNA
<213> ORGANISM: Artificial Sequence
<220> FEATURE:
<223> OTHER INFORMATION: asiRNA

<400> SEQUENCE: 419
uuggggUAGU ccucaaacau c                                            21

<210> SEQ ID NO 420
```

```
<211> LENGTH: 21
<212> TYPE: RNA
<213> ORGANISM: Artificial Sequence
<220> FEATURE:
<223> OTHER INFORMATION: asiRNA

<400> SEQUENCE: 420 uggggulaguc cucaaacauc u                                              21

<210> SEQ ID NO 421
<211> LENGTH: 21
<212> TYPE: RNA
<213> ORGANISM: Artificial Sequence
<220> FEATURE:
<223> OTHER INFORMATION: asiRNA

<400> SEQUENCE: 421 gcuuccgag auuggggua g                                                 21

<210> SEQ ID NO 422
<211> LENGTH: 21
<212> TYPE: RNA
<213> ORGANISM: Artificial Sequence
<220> FEATURE:
<223> OTHER INFORMATION: asiRNA

<400> SEQUENCE: 422
gaauggaaua agggcuuucc g                                               21

<210> SEQ ID NO 423
<211> LENGTH: 21
<212> TYPE: RNA
<213> ORGANISM: Artificial Sequence
<220> FEATURE:
<223> OTHER INFORMATION: asiRNA

<400> SEQUENCE: 423
aauggaauaa gggcuuuccg a                                               21

<210> SEQ ID NO 424
<211> LENGTH: 21
<212> TYPE: RNA
<213> ORGANISM: Artificial Sequence
<220> FEATURE:
<223> OTHER INFORMATION: asiRNA

<400> SEQUENCE: 424
uggccagggc auagccgauc c                                               21

<210> SEQ ID NO 425
<211> LENGTH: 20
<212> TYPE: DNA
<213> ORGANISM: Artificial Sequence
<220> FEATURE:
<223> OTHER INFORMATION: Primer

<400> SEQUENCE: 425
gagtcaacgg atttggtcgt                                                 20

<210> SEQ ID NO 426
<211> LENGTH: 20
<212> TYPE: DNA
<213> ORGANISM: Artificial Sequence
<220> FEATURE:
<223> OTHER INFORMATION: Primer

<400> SEQUENCE: 426
```
gacaagcttc ccgttctcag                                              20

<210> SEQ ID NO 427
<211> LENGTH: 20
<212> TYPE: DNA
<213> ORGANISM: Artificial Sequence
<220> FEATURE:
<223> OTHER INFORMATION: Primer

<400> SEQUENCE: 427
tgaacctggg tggcttatga                                              20

<210> SEQ ID NO 428
<211> LENGTH: 19
<212> TYPE: DNA
<213> ORGANISM: Artificial Sequence
<220> FEATURE:
<223> OTHER INFORMATION: Primer

<400> SEQUENCE: 428
gaaaggaaag ttgcttggg                                               19

<210> SEQ ID NO 429
<211> LENGTH: 16
<212> TYPE: RNA
<213> ORGANISM: Artificial Sequence
<220> FEATURE:
<223> OTHER INFORMATION: asiRNA

<400> SEQUENCE: 429
gagaugaagc uucugg                                                  16

<210> SEQ ID NO 430
<211> LENGTH: 16
<212> TYPE: RNA
<213> ORGANISM: Artificial Sequence
<220> FEATURE:
<223> OTHER INFORMATION: asiRNA

<400> SEQUENCE: 430
ggagaugaag cuucug                                                  16

<210> SEQ ID NO 431
<211> LENGTH: 16
<212> TYPE: RNA
<213> ORGANISM: Artificial Sequence
<220> FEATURE:
<223> OTHER INFORMATION: asiRNA

<400> SEQUENCE: 431
guggagauga agcuuc                                                  16

<210> SEQ ID NO 432
<211> LENGTH: 16
<212> TYPE: RNA
<213> ORGANISM: Artificial Sequence
<220> FEATURE:
<223> OTHER INFORMATION: asiRNA

<400> SEQUENCE: 432
uguggagaug aagcuu                                                  16

<210> SEQ ID NO 433
<211> LENGTH: 16
<212> TYPE: RNA

```
<213> ORGANISM: Artificial Sequence
<220> FEATURE:
<223> OTHER INFORMATION: asiRNA

<400> SEQUENCE: 433
ucuguggaga ugaagc                                                16

<210> SEQ ID NO 434
<211> LENGTH: 16
<212> TYPE: RNA
<213> ORGANISM: Artificial Sequence
<220> FEATURE:
<223> OTHER INFORMATION: asiRNA

<400> SEQUENCE: 434
ugaucugugg agauga                                                16

<210> SEQ ID NO 435
<211> LENGTH: 16
<212> TYPE: RNA
<213> ORGANISM: Artificial Sequence
<220> FEATURE:
<223> OTHER INFORMATION: asiRNA

<400> SEQUENCE: 435
cugaucugug gagaug                                                16

<210> SEQ ID NO 436
<211> LENGTH: 16
<212> TYPE: RNA
<213> ORGANISM: Artificial Sequence
<220> FEATURE:
<223> OTHER INFORMATION: asiRNA

<400> SEQUENCE: 436
aagaccugcc ugaucu                                                16

<210> SEQ ID NO 437
<211> LENGTH: 16
<212> TYPE: RNA
<213> ORGANISM: Artificial Sequence
<220> FEATURE:
<223> OTHER INFORMATION: asiRNA

<400> SEQUENCE: 437
uuuccacccc agaaga                                                16

<210> SEQ ID NO 438
<211> LENGTH: 16
<212> TYPE: RNA
<213> ORGANISM: Artificial Sequence
<220> FEATURE:
<223> OTHER INFORMATION: asiRNA

<400> SEQUENCE: 438 acuuccacc ccagaa                                                 16

<210> SEQ ID NO 439
<211> LENGTH: 16
<212> TYPE: RNA
<213> ORGANISM: Artificial Sequence
<220> FEATURE:
<223> OTHER INFORMATION: asiRNA

<400> SEQUENCE: 439
aagggaaaca gaagua                                                16
```

```
<210> SEQ ID NO 440
<211> LENGTH: 16
<212> TYPE: RNA
<213> ORGANISM: Artificial Sequence
<220> FEATURE:
<223> OTHER INFORMATION: asiRNA

<400> SEQUENCE: 440
gaagggaaac agaagu                                                      16

<210> SEQ ID NO 441
<211> LENGTH: 16
<212> TYPE: RNA
<213> ORGANISM: Artificial Sequence
<220> FEATURE:
<223> OTHER INFORMATION: asiRNA

<400> SEQUENCE: 441
cugaagggaa acagaa                                                      16

<210> SEQ ID NO 442
<211> LENGTH: 16
<212> TYPE: RNA
<213> ORGANISM: Artificial Sequence
<220> FEATURE:
<223> OTHER INFORMATION: asiRNA

<400> SEQUENCE: 442
caaaagagcc gcugaa                                                      16

<210> SEQ ID NO 443
<211> LENGTH: 16
<212> TYPE: RNA
<213> ORGANISM: Artificial Sequence
<220> FEATURE:
<223> OTHER INFORMATION: asiRNA

<400> SEQUENCE: 443
ucaaaagagc cgcuga                                                      16

<210> SEQ ID NO 444
<211> LENGTH: 16
<212> TYPE: RNA
<213> ORGANISM: Artificial Sequence
<220> FEATURE:
<223> OTHER INFORMATION: asiRNA

<400> SEQUENCE: 444
cuucaaaaga gccgcu                                                      16

<210> SEQ ID NO 445
<211> LENGTH: 16
<212> TYPE: RNA
<213> ORGANISM: Artificial Sequence
<220> FEATURE:
<223> OTHER INFORMATION: asiRNA

<400> SEQUENCE: 445
cuucuucaaa agagcc                                                      16

<210> SEQ ID NO 446
<211> LENGTH: 16
<212> TYPE: RNA
<213> ORGANISM: Artificial Sequence
<220> FEATURE:
```

```
<223> OTHER INFORMATION: asiRNA

<400> SEQUENCE: 446
ucuucuucaa aagagc                                                        16

<210> SEQ ID NO 447
<211> LENGTH: 16
<212> TYPE: RNA
<213> ORGANISM: Artificial Sequence
<220> FEATURE:
<223> OTHER INFORMATION: asiRNA

<400> SEQUENCE: 447
aggucuucuu caaaag                                                        16

<210> SEQ ID NO 448
<211> LENGTH: 16
<212> TYPE: RNA
<213> ORGANISM: Artificial Sequence
<220> FEATURE:
<223> OTHER INFORMATION: asiRNA

<400> SEQUENCE: 448
aagcagggau gacucu                                                        16

<210> SEQ ID NO 449
<211> LENGTH: 16
<212> TYPE: RNA
<213> ORGANISM: Artificial Sequence
<220> FEATURE:
<223> OTHER INFORMATION: asiRNA

<400> SEQUENCE: 449
ugaagcaggg augacu                                                        16

<210> SEQ ID NO 450
<211> LENGTH: 16
<212> TYPE: RNA
<213> ORGANISM: Artificial Sequence
<220> FEATURE:
<223> OTHER INFORMATION: asiRNA

<400> SEQUENCE: 450
uuaugaagca gggaug                                                        16

<210> SEQ ID NO 451
<211> LENGTH: 16
<212> TYPE: RNA
<213> ORGANISM: Artificial Sequence
<220> FEATURE:
<223> OTHER INFORMATION: asiRNA

<400> SEQUENCE: 451
uguuaugaag caggga                                                        16

<210> SEQ ID NO 452
<211> LENGTH: 16
<212> TYPE: RNA
<213> ORGANISM: Artificial Sequence
<220> FEATURE:
<223> OTHER INFORMATION: asiRNA

<400> SEQUENCE: 452
auguuaugaa gcaggg                                                        16
```

```
<210> SEQ ID NO 453
<211> LENGTH: 16
<212> TYPE: RNA
<213> ORGANISM: Artificial Sequence
<220> FEATURE:
<223> OTHER INFORMATION: asiRNA

<400> SEQUENCE: 453
gcuaugaaug ucagcc                                                     16

<210> SEQ ID NO 454
<211> LENGTH: 16
<212> TYPE: RNA
<213> ORGANISM: Artificial Sequence
<220> FEATURE:
<223> OTHER INFORMATION: asiRNA

<400> SEQUENCE: 454
ggcuaugaau gucagc                                                     16

<210> SEQ ID NO 455
<211> LENGTH: 16
<212> TYPE: RNA
<213> ORGANISM: Artificial Sequence
<220> FEATURE:
<223> OTHER INFORMATION: asiRNA

<400> SEQUENCE: 455
gaaggcuaug aauguc                                                     16

<210> SEQ ID NO 456
<211> LENGTH: 16
<212> TYPE: RNA
<213> ORGANISM: Artificial Sequence
<220> FEATURE:
<223> OTHER INFORMATION: asiRNA

<400> SEQUENCE: 456
uugaaggcua ugaaug                                                     16

<210> SEQ ID NO 457
<211> LENGTH: 16
<212> TYPE: RNA
<213> ORGANISM: Artificial Sequence
<220> FEATURE:
<223> OTHER INFORMATION: asiRNA

<400> SEQUENCE: 457
gaagccauug agccag                                                     16

<210> SEQ ID NO 458
<211> LENGTH: 16
<212> TYPE: RNA
<213> ORGANISM: Artificial Sequence
<220> FEATURE:
<223> OTHER INFORMATION: asiRNA

<400> SEQUENCE: 458
cuggcuuccg caacuu                                                     16

<210> SEQ ID NO 459
<211> LENGTH: 16
<212> TYPE: RNA
<213> ORGANISM: Artificial Sequence
<220> FEATURE:
<223> OTHER INFORMATION: asiRNA
```

```
<400> SEQUENCE: 459
ugccuggcuu ccgcaa                                              16

<210> SEQ ID NO 460
<211> LENGTH: 16
<212> TYPE: RNA
<213> ORGANISM: Artificial Sequence
<220> FEATURE:
<223> OTHER INFORMATION: asiRNA

<400> SEQUENCE: 460
agugggccaa ggccuu                                              16

<210> SEQ ID NO 461
<211> LENGTH: 16
<212> TYPE: RNA
<213> ORGANISM: Artificial Sequence
<220> FEATURE:
<223> OTHER INFORMATION: asiRNA

<400> SEQUENCE: 461
ccaggaugcu cuacuu                                              16

<210> SEQ ID NO 462
<211> LENGTH: 16
<212> TYPE: RNA
<213> ORGANISM: Artificial Sequence
<220> FEATURE:
<223> OTHER INFORMATION: asiRNA

<400> SEQUENCE: 462
uccaggaugc ucuacu                                              16

<210> SEQ ID NO 463
<211> LENGTH: 16
<212> TYPE: RNA
<213> ORGANISM: Artificial Sequence
<220> FEATURE:
<223> OTHER INFORMATION: asiRNA

<400> SEQUENCE: 463
aacuccagga ugcucu                                              16

<210> SEQ ID NO 464
<211> LENGTH: 16
<212> TYPE: RNA
<213> ORGANISM: Artificial Sequence
<220> FEATURE:
<223> OTHER INFORMATION: asiRNA

<400> SEQUENCE: 464
uaccgcaugc acaagu                                              16

<210> SEQ ID NO 465
<211> LENGTH: 16
<212> TYPE: RNA
<213> ORGANISM: Artificial Sequence
<220> FEATURE:
<223> OTHER INFORMATION: asiRNA

<400> SEQUENCE: 465
aguaccgcau gcacaa                                              16

<210> SEQ ID NO 466
<211> LENGTH: 16
```

```
<212> TYPE: RNA
<213> ORGANISM: Artificial Sequence
<220> FEATURE:
<223> OTHER INFORMATION: asiRNA

<400> SEQUENCE: 466
caaugaguac cgcaug                                                    16

<210> SEQ ID NO 467
<211> LENGTH: 16
<212> TYPE: RNA
<213> ORGANISM: Artificial Sequence
<220> FEATURE:
<223> OTHER INFORMATION: asiRNA

<400> SEQUENCE: 467
ucaaugagua ccgcau                                                    16

<210> SEQ ID NO 468
<211> LENGTH: 16
<212> TYPE: RNA
<213> ORGANISM: Artificial Sequence
<220> FEATURE:
<223> OTHER INFORMATION: asiRNA

<400> SEQUENCE: 468
uucaaugagu accgca                                                    16

<210> SEQ ID NO 469
<211> LENGTH: 16
<212> TYPE: RNA
<213> ORGANISM: Artificial Sequence
<220> FEATURE:
<223> OTHER INFORMATION: asiRNA

<400> SEQUENCE: 469
uuggauggcu ccaaau                                                    16

<210> SEQ ID NO 470
<211> LENGTH: 16
<212> TYPE: RNA
<213> ORGANISM: Artificial Sequence
<220> FEATURE:
<223> OTHER INFORMATION: asiRNA

<400> SEQUENCE: 470
aguuuggaug gcucca                                                    16

<210> SEQ ID NO 471
<211> LENGTH: 16
<212> TYPE: RNA
<213> ORGANISM: Artificial Sequence
<220> FEATURE:
<223> OTHER INFORMATION: asiRNA

<400> SEQUENCE: 471
agaguuugga uggcuc                                                    16

<210> SEQ ID NO 472
<211> LENGTH: 16
<212> TYPE: RNA
<213> ORGANISM: Artificial Sequence
<220> FEATURE:
<223> OTHER INFORMATION: asiRNA

<400> SEQUENCE: 472
```
ucaaggaacu cgaucg                                                          16

<210> SEQ ID NO 473
<211> LENGTH: 16
<212> TYPE: RNA
<213> ORGANISM: Artificial Sequence
<220> FEATURE:
<223> OTHER INFORMATION: asiRNA

<400> SEQUENCE: 473
caucaaggaa cucgau                                                          16

<210> SEQ ID NO 474
<211> LENGTH: 16
<212> TYPE: RNA
<213> ORGANISM: Artificial Sequence
<220> FEATURE:
<223> OTHER INFORMATION: asiRNA

<400> SEQUENCE: 474
cuacaucaag gaacuc                                                          16

<210> SEQ ID NO 475
<211> LENGTH: 16
<212> TYPE: RNA
<213> ORGANISM: Artificial Sequence
<220> FEATURE:
<223> OTHER INFORMATION: asiRNA

<400> SEQUENCE: 475
gaacuacauc aaggaa                                                          16

<210> SEQ ID NO 476
<211> LENGTH: 16
<212> TYPE: RNA
<213> ORGANISM: Artificial Sequence
<220> FEATURE:
<223> OTHER INFORMATION: asiRNA

<400> SEQUENCE: 476
cuucgaauga acuaca                                                          16

<210> SEQ ID NO 477
<211> LENGTH: 16
<212> TYPE: RNA
<213> ORGANISM: Artificial Sequence
<220> FEATURE:
<223> OTHER INFORMATION: asiRNA

<400> SEQUENCE: 477
ugaacuucga augaac                                                          16

<210> SEQ ID NO 478
<211> LENGTH: 16
<212> TYPE: RNA
<213> ORGANISM: Artificial Sequence
<220> FEATURE:
<223> OTHER INFORMATION: asiRNA

<400> SEQUENCE: 478
ugaugaacuu cgaaug                                                          16

<210> SEQ ID NO 479
<211> LENGTH: 16
<212> TYPE: RNA
<213> ORGANISM: Artificial Sequence

```
<220> FEATURE:
<223> OTHER INFORMATION: asiRNA

<400> SEQUENCE: 479
gggcugaaaa aucaaa                                                    16

<210> SEQ ID NO 480
<211> LENGTH: 16
<212> TYPE: RNA
<213> ORGANISM: Artificial Sequence
<220> FEATURE:
<223> OTHER INFORMATION: asiRNA

<400> SEQUENCE: 480
gaugggcuga aaauc                                                     16

<210> SEQ ID NO 481
<211> LENGTH: 16
<212> TYPE: RNA
<213> ORGANISM: Artificial Sequence
<220> FEATURE:
<223> OTHER INFORMATION: asiRNA

<400> SEQUENCE: 481
uauuccagug gauggg                                                    16

<210> SEQ ID NO 482
<211> LENGTH: 16
<212> TYPE: RNA
<213> ORGANISM: Artificial Sequence
<220> FEATURE:
<223> OTHER INFORMATION: asiRNA

<400> SEQUENCE: 482
cauuauucca guggau                                                    16

<210> SEQ ID NO 483
<211> LENGTH: 16
<212> TYPE: RNA
<213> ORGANISM: Artificial Sequence
<220> FEATURE:
<223> OTHER INFORMATION: asiRNA

<400> SEQUENCE: 483
agcauuauuc cagugg                                                    16

<210> SEQ ID NO 484
<211> LENGTH: 16
<212> TYPE: RNA
<213> ORGANISM: Artificial Sequence
<220> FEATURE:
<223> OTHER INFORMATION: asiRNA

<400> SEQUENCE: 484
uucagcauua uuccag                                                    16

<210> SEQ ID NO 485
<211> LENGTH: 16
<212> TYPE: RNA
<213> ORGANISM: Artificial Sequence
<220> FEATURE:
<223> OTHER INFORMATION: asiRNA

<400> SEQUENCE: 485
cucuucagca uuauuc                                                    16
```

<210> SEQ ID NO 486
<211> LENGTH: 16
<212> TYPE: RNA
<213> ORGANISM: Artificial Sequence
<220> FEATURE:
<223> OTHER INFORMATION: asiRNA

<400> SEQUENCE: 486
cugcucucuu cagcau                                               16

<210> SEQ ID NO 487
<211> LENGTH: 16
<212> TYPE: RNA
<213> ORGANISM: Artificial Sequence
<220> FEATURE:
<223> OTHER INFORMATION: asiRNA

<400> SEQUENCE: 487
aagcacugcu cucuuc                                               16

<210> SEQ ID NO 488
<211> LENGTH: 16
<212> TYPE: RNA
<213> ORGANISM: Artificial Sequence
<220> FEATURE:
<223> OTHER INFORMATION: asiRNA

<400> SEQUENCE: 488
gaaagcacug cucucu                                               16

<210> SEQ ID NO 489
<211> LENGTH: 16
<212> TYPE: RNA
<213> ORGANISM: Artificial Sequence
<220> FEATURE:
<223> OTHER INFORMATION: asiRNA

<400> SEQUENCE: 489
caugaaagca cugcuc                                               16

<210> SEQ ID NO 490
<211> LENGTH: 16
<212> TYPE: RNA
<213> ORGANISM: Artificial Sequence
<220> FEATURE:
<223> OTHER INFORMATION: asiRNA

<400> SEQUENCE: 490
gugcaugaaa gcacug                                               16

<210> SEQ ID NO 491
<211> LENGTH: 16
<212> TYPE: RNA
<213> ORGANISM: Artificial Sequence
<220> FEATURE:
<223> OTHER INFORMATION: asiRNA

<400> SEQUENCE: 491
uuccugugca ugaaag                                               16

<210> SEQ ID NO 492
<211> LENGTH: 16
<212> TYPE: RNA
<213> ORGANISM: Artificial Sequence
<220> FEATURE:
<223> OTHER INFORMATION: asiRNA

```
<400> SEQUENCE: 492
gaauuccugu gcauga                                                    16

<210> SEQ ID NO 493
<211> LENGTH: 16
<212> TYPE: RNA
<213> ORGANISM: Artificial Sequence
<220> FEATURE:
<223> OTHER INFORMATION: asiRNA

<400> SEQUENCE: 493
aggaauuccu gugcau                                                    16

<210> SEQ ID NO 494
<211> LENGTH: 16
<212> TYPE: RNA
<213> ORGANISM: Artificial Sequence
<220> FEATURE:
<223> OTHER INFORMATION: asiRNA

<400> SEQUENCE: 494
ucaccaagcu ccugga                                                    16

<210> SEQ ID NO 495
<211> LENGTH: 16
<212> TYPE: RNA
<213> ORGANISM: Artificial Sequence
<220> FEATURE:
<223> OTHER INFORMATION: asiRNA

<400> SEQUENCE: 495
accagcucac caagcu                                                    16

<210> SEQ ID NO 496
<211> LENGTH: 16
<212> TYPE: RNA
<213> ORGANISM: Artificial Sequence
<220> FEATURE:
<223> OTHER INFORMATION: asiRNA

<400> SEQUENCE: 496
cuaccagcuc accaag                                                    16

<210> SEQ ID NO 497
<211> LENGTH: 16
<212> TYPE: RNA
<213> ORGANISM: Artificial Sequence
<220> FEATURE:
<223> OTHER INFORMATION: asiRNA

<400> SEQUENCE: 497
accugcuaau caaguc                                                    16

<210> SEQ ID NO 498
<211> LENGTH: 16
<212> TYPE: RNA
<213> ORGANISM: Artificial Sequence
<220> FEATURE:
<223> OTHER INFORMATION: asiRNA

<400> SEQUENCE: 498
gaccugcuaa ucaagu                                                    16

<210> SEQ ID NO 499
```

```
<211> LENGTH: 16
<212> TYPE: RNA
<213> ORGANISM: Artificial Sequence
<220> FEATURE:
<223> OTHER INFORMATION: asiRNA

<400> SEQUENCE: 499
uuugaccugc uaauca                                                      16

<210> SEQ ID NO 500
<211> LENGTH: 16
<212> TYPE: RNA
<213> ORGANISM: Artificial Sequence
<220> FEATURE:
<223> OTHER INFORMATION: asiRNA

<400> SEQUENCE: 500 cuuugaccu gcuaau                                                       16

<210> SEQ ID NO 501
<211> LENGTH: 16
<212> TYPE: RNA
<213> ORGANISM: Artificial Sequence
<220> FEATURE:
<223> OTHER INFORMATION: asiRNA

<400> SEQUENCE: 501
ucacuuuuga ccugcu                                                      16

<210> SEQ ID NO 502
<211> LENGTH: 16
<212> TYPE: RNA
<213> ORGANISM: Artificial Sequence
<220> FEATURE:
<223> OTHER INFORMATION: asiRNA

<400> SEQUENCE: 502
uucacuuuug accugc                                                      16

<210> SEQ ID NO 503
<211> LENGTH: 16
<212> TYPE: RNA
<213> ORGANISM: Artificial Sequence
<220> FEATURE:
<223> OTHER INFORMATION: asiRNA

<400> SEQUENCE: 503
caguucacuu uugacc                                                      16

<210> SEQ ID NO 504
<211> LENGTH: 16
<212> TYPE: RNA
<213> ORGANISM: Artificial Sequence
<220> FEATURE:
<223> OTHER INFORMATION: asiRNA

<400> SEQUENCE: 504
caucaguuca cuuuug                                                      16

<210> SEQ ID NO 505
<211> LENGTH: 16
<212> TYPE: RNA
<213> ORGANISM: Artificial Sequence
<220> FEATURE:
<223> OTHER INFORMATION: asiRNA

<400> SEQUENCE: 505
```
cugcaucagu ucacuu                                                         16

<210> SEQ ID NO 506
<211> LENGTH: 16
<212> TYPE: RNA
<213> ORGANISM: Artificial Sequence
<220> FEATURE:
<223> OTHER INFORMATION: asiRNA

<400> SEQUENCE: 506
gcugcaucag uucacu                                                         16

<210> SEQ ID NO 507
<211> LENGTH: 16
<212> TYPE: RNA
<213> ORGANISM: Artificial Sequence
<220> FEATURE:
<223> OTHER INFORMATION: asiRNA

<400> SEQUENCE: 507
ccaucuauuu ccacac                                                         16

<210> SEQ ID NO 508
<211> LENGTH: 16
<212> TYPE: RNA
<213> ORGANISM: Artificial Sequence
<220> FEATURE:
<223> OTHER INFORMATION: asiRNA

<400> SEQUENCE: 508
cccaucuauu uccaca                                                         16

<210> SEQ ID NO 509
<211> LENGTH: 16
<212> TYPE: RNA
<213> ORGANISM: Artificial Sequence
<220> FEATURE:
<223> OTHER INFORMATION: asiRNA

<400> SEQUENCE: 509
agcccaucua uuucca                                                         16

<210> SEQ ID NO 510
<211> LENGTH: 16
<212> TYPE: RNA
<213> ORGANISM: Artificial Sequence
<220> FEATURE:
<223> OTHER INFORMATION: asiRNA

<400> SEQUENCE: 510
ucaagcccau cuauuu                                                         16

<210> SEQ ID NO 511
<211> LENGTH: 16
<212> TYPE: RNA
<213> ORGANISM: Artificial Sequence
<220> FEATURE:
<223> OTHER INFORMATION: asiRNA

<400> SEQUENCE: 511
ggaaagucaa gcccau                                                         16

<210> SEQ ID NO 512
<211> LENGTH: 16
<212> TYPE: RNA

```
<213> ORGANISM: Artificial Sequence
<220> FEATURE:
<223> OTHER INFORMATION: asiRNA

<400> SEQUENCE: 512
cugggaaagu caagcc                                                         16

<210> SEQ ID NO 513
<211> LENGTH: 16
<212> TYPE: RNA
<213> ORGANISM: Artificial Sequence
<220> FEATURE:
<223> OTHER INFORMATION: asiRNA

<400> SEQUENCE: 513 uuucuggaa agucaa                                                          16

<210> SEQ ID NO 514
<211> LENGTH: 16
<212> TYPE: RNA
<213> ORGANISM: Artificial Sequence
<220> FEATURE:
<223> OTHER INFORMATION: asiRNA

<400> SEQUENCE: 514
uccuuucugg gaaagu                                                         16

<210> SEQ ID NO 515
<211> LENGTH: 16
<212> TYPE: RNA
<213> ORGANISM: Artificial Sequence
<220> FEATURE:
<223> OTHER INFORMATION: asiRNA

<400> SEQUENCE: 515
ccaagauccu uucugg                                                         16

<210> SEQ ID NO 516
<211> LENGTH: 16
<212> TYPE: RNA
<213> ORGANISM: Artificial Sequence
<220> FEATURE:
<223> OTHER INFORMATION: asiRNA

<400> SEQUENCE: 516
ugcccaagau ccuuuc                                                         16

<210> SEQ ID NO 517
<211> LENGTH: 16
<212> TYPE: RNA
<213> ORGANISM: Artificial Sequence
<220> FEATURE:
<223> OTHER INFORMATION: asiRNA

<400> SEQUENCE: 517
aagugcccaa gauccu                                                         16

<210> SEQ ID NO 518
<211> LENGTH: 16
<212> TYPE: RNA
<213> ORGANISM: Artificial Sequence
<220> FEATURE:
<223> OTHER INFORMATION: asiRNA

<400> SEQUENCE: 518
ugcaagugcc caagau                                                         16
```

```
<210> SEQ ID NO 519
<211> LENGTH: 16
<212> TYPE: RNA
<213> ORGANISM: Artificial Sequence
<220> FEATURE:
<223> OTHER INFORMATION: asiRNA

<400> SEQUENCE: 519
ucucugugca agugcc                                                         16

<210> SEQ ID NO 520
<211> LENGTH: 16
<212> TYPE: RNA
<213> ORGANISM: Artificial Sequence
<220> FEATURE:
<223> OTHER INFORMATION: asiRNA

<400> SEQUENCE: 520
ucaucucugu gcaagu                                                         16

<210> SEQ ID NO 521
<211> LENGTH: 16
<212> TYPE: RNA
<213> ORGANISM: Artificial Sequence
<220> FEATURE:
<223> OTHER INFORMATION: asiRNA

<400> SEQUENCE: 521
agaucaucuc ugugca                                                         16

<210> SEQ ID NO 522
<211> LENGTH: 16
<212> TYPE: RNA
<213> ORGANISM: Artificial Sequence
<220> FEATURE:
<223> OTHER INFORMATION: asiRNA

<400> SEQUENCE: 522
cagagaucau cucugu                                                         16

<210> SEQ ID NO 523
<211> LENGTH: 16
<212> TYPE: RNA
<213> ORGANISM: Artificial Sequence
<220> FEATURE:
<223> OTHER INFORMATION: asiRNA

<400> SEQUENCE: 523
cacuggcacu aaaaaa                                                         16

<210> SEQ ID NO 524
<211> LENGTH: 16
<212> TYPE: RNA
<213> ORGANISM: Artificial Sequence
<220> FEATURE:
<223> OTHER INFORMATION: asiRNA

<400> SEQUENCE: 524
ucacuggcac uaaaaa                                                         16

<210> SEQ ID NO 525
<211> LENGTH: 16
<212> TYPE: RNA
<213> ORGANISM: Artificial Sequence
<220> FEATURE:
```

```
<223> OTHER INFORMATION: asiRNA

<400> SEQUENCE: 525
guucacuggc acuaaa                                                          16

<210> SEQ ID NO 526
<211> LENGTH: 16
<212> TYPE: RNA
<213> ORGANISM: Artificial Sequence
<220> FEATURE:
<223> OTHER INFORMATION: asiRNA

<400> SEQUENCE: 526
uauguucacu ggcacu                                                          16

<210> SEQ ID NO 527
<211> LENGTH: 16
<212> TYPE: RNA
<213> ORGANISM: Artificial Sequence
<220> FEATURE:
<223> OTHER INFORMATION: asiRNA

<400> SEQUENCE: 527
uguauguuca cuggca                                                          16

<210> SEQ ID NO 528
<211> LENGTH: 16
<212> TYPE: RNA
<213> ORGANISM: Artificial Sequence
<220> FEATURE:
<223> OTHER INFORMATION: asiRNA

<400> SEQUENCE: 528
uauguauguu cacugg                                                          16

<210> SEQ ID NO 529
<211> LENGTH: 16
<212> TYPE: RNA
<213> ORGANISM: Artificial Sequence
<220> FEATURE:
<223> OTHER INFORMATION: asiRNA

<400> SEQUENCE: 529
ggguaguugc ugaggu                                                          16

<210> SEQ ID NO 530
<211> LENGTH: 16
<212> TYPE: RNA
<213> ORGANISM: Artificial Sequence
<220> FEATURE:
<223> OTHER INFORMATION: asiRNA

<400> SEQUENCE: 530
uggguaguug cugagg                                                          16

<210> SEQ ID NO 531
<211> LENGTH: 16
<212> TYPE: RNA
<213> ORGANISM: Artificial Sequence
<220> FEATURE:
<223> OTHER INFORMATION: asiRNA

<400> SEQUENCE: 531
cuuuggguag uugcug                                                          16
```

```
<210> SEQ ID NO 532
<211> LENGTH: 16
<212> TYPE: RNA
<213> ORGANISM: Artificial Sequence
<220> FEATURE:
<223> OTHER INFORMATION: asiRNA

<400> SEQUENCE: 532
ccuuugggua guugcu                                                         16

<210> SEQ ID NO 533
<211> LENGTH: 16
<212> TYPE: RNA
<213> ORGANISM: Artificial Sequence
<220> FEATURE:
<223> OTHER INFORMATION: asiRNA

<400> SEQUENCE: 533
ccaccaucca caugau                                                         16

<210> SEQ ID NO 534
<211> LENGTH: 16
<212> TYPE: RNA
<213> ORGANISM: Artificial Sequence
<220> FEATURE:
<223> OTHER INFORMATION: asiRNA

<400> SEQUENCE: 534
cauuagugcc ucuuug                                                         16

<210> SEQ ID NO 535
<211> LENGTH: 16
<212> TYPE: RNA
<213> ORGANISM: Artificial Sequence
<220> FEATURE:
<223> OTHER INFORMATION: asiRNA

<400> SEQUENCE: 535
gcauuagugc cucuuu                                                         16

<210> SEQ ID NO 536
<211> LENGTH: 16
<212> TYPE: RNA
<213> ORGANISM: Artificial Sequence
<220> FEATURE:
<223> OTHER INFORMATION: asiRNA

<400> SEQUENCE: 536
agcauuagug ccucuu                                                         16

<210> SEQ ID NO 537
<211> LENGTH: 16
<212> TYPE: RNA
<213> ORGANISM: Artificial Sequence
<220> FEATURE:
<223> OTHER INFORMATION: asiRNA

<400> SEQUENCE: 537
aagcauuagu gccucu                                                         16

<210> SEQ ID NO 538
<211> LENGTH: 16
<212> TYPE: RNA
<213> ORGANISM: Artificial Sequence
<220> FEATURE:
<223> OTHER INFORMATION: asiRNA
```

-continued

```
<400> SEQUENCE: 538
gcccauguua gcuuau                                                    16

<210> SEQ ID NO 539
<211> LENGTH: 16
<212> TYPE: RNA
<213> ORGANISM: Artificial Sequence
<220> FEATURE:
<223> OTHER INFORMATION: asiRNA

<400> SEQUENCE: 539
gaaacuuguu uguugg                                                    16

<210> SEQ ID NO 540
<211> LENGTH: 16
<212> TYPE: RNA
<213> ORGANISM: Artificial Sequence
<220> FEATURE:
<223> OTHER INFORMATION: asiRNA

<400> SEQUENCE: 540
gcagaaacuu guugu                                                     16

<210> SEQ ID NO 541
<211> LENGTH: 16
<212> TYPE: RNA
<213> ORGANISM: Artificial Sequence
<220> FEATURE:
<223> OTHER INFORMATION: asiRNA

<400> SEQUENCE: 541
auggcagaaa cuuguu                                                    16

<210> SEQ ID NO 542
<211> LENGTH: 16
<212> TYPE: RNA
<213> ORGANISM: Artificial Sequence
<220> FEATURE:
<223> OTHER INFORMATION: asiRNA

<400> SEQUENCE: 542
aauggcagaa acugu                                                     16

<210> SEQ ID NO 543
<211> LENGTH: 16
<212> TYPE: RNA
<213> ORGANISM: Artificial Sequence
<220> FEATURE:
<223> OTHER INFORMATION: asiRNA

<400> SEQUENCE: 543
ggaaucuuuu guugcu                                                    16

<210> SEQ ID NO 544
<211> LENGTH: 16
<212> TYPE: RNA
<213> ORGANISM: Artificial Sequence
<220> FEATURE:
<223> OTHER INFORMATION: asiRNA

<400> SEQUENCE: 544
uggaaucuuu uguugc                                                    16

<210> SEQ ID NO 545
<211> LENGTH: 16
```

```
<212> TYPE: RNA
<213> ORGANISM: Artificial Sequence
<220> FEATURE:
<223> OTHER INFORMATION: asiRNA

<400> SEQUENCE: 545
uaguguucug uucucu                                                       16

<210> SEQ ID NO 546
<211> LENGTH: 16
<212> TYPE: RNA
<213> ORGANISM: Artificial Sequence
<220> FEATURE:
<223> OTHER INFORMATION: asiRNA

<400> SEQUENCE: 546
cuaguguucu guucuc                                                       16

<210> SEQ ID NO 547
<211> LENGTH: 21
<212> TYPE: RNA
<213> ORGANISM: Artificial Sequence
<220> FEATURE:
<223> OTHER INFORMATION: asiRNA

<400> SEQUENCE: 547
ccagaagcuu caucuccaca g                                                 21

<210> SEQ ID NO 548
<211> LENGTH: 21
<212> TYPE: RNA
<213> ORGANISM: Artificial Sequence
<220> FEATURE:
<223> OTHER INFORMATION: asiRNA

<400> SEQUENCE: 548
cagaagcuuc aucuccacag a                                                 21

<210> SEQ ID NO 549
<211> LENGTH: 21
<212> TYPE: RNA
<213> ORGANISM: Artificial Sequence
<220> FEATURE:
<223> OTHER INFORMATION: asiRNA

<400> SEQUENCE: 549
gaagcuucau cuccacagau c                                                 21

<210> SEQ ID NO 550
<211> LENGTH: 21
<212> TYPE: RNA
<213> ORGANISM: Artificial Sequence
<220> FEATURE:
<223> OTHER INFORMATION: asiRNA

<400> SEQUENCE: 550
aagcuucauc uccacagauc a                                                 21

<210> SEQ ID NO 551
<211> LENGTH: 21
<212> TYPE: RNA
<213> ORGANISM: Artificial Sequence
<220> FEATURE:
<223> OTHER INFORMATION: asiRNA

<400> SEQUENCE: 551
```
gcuucaucuc cacagaucag g    21

<210> SEQ ID NO 552
<211> LENGTH: 21
<212> TYPE: RNA
<213> ORGANISM: Artificial Sequence
<220> FEATURE:
<223> OTHER INFORMATION: asiRNA

<400> SEQUENCE: 552
ucaucuccac agaucaggca g    21

<210> SEQ ID NO 553
<211> LENGTH: 21
<212> TYPE: RNA
<213> ORGANISM: Artificial Sequence
<220> FEATURE:
<223> OTHER INFORMATION: asiRNA

<400> SEQUENCE: 553
caucuccaca gaucaggcag g    21

<210> SEQ ID NO 554
<211> LENGTH: 21
<212> TYPE: RNA
<213> ORGANISM: Artificial Sequence
<220> FEATURE:
<223> OTHER INFORMATION: asiRNA

<400> SEQUENCE: 554
agaucaggca ggucuucugg g    21

<210> SEQ ID NO 555
<211> LENGTH: 21
<212> TYPE: RNA
<213> ORGANISM: Artificial Sequence
<220> FEATURE:
<223> OTHER INFORMATION: asiRNA

<400> SEQUENCE: 555
ucuucugggg uggaaaguaa u    21

<210> SEQ ID NO 556
<211> LENGTH: 21
<212> TYPE: RNA
<213> ORGANISM: Artificial Sequence
<220> FEATURE:
<223> OTHER INFORMATION: asiRNA

<400> SEQUENCE: 556
uucuggggug gaaaguaaua g    21

<210> SEQ ID NO 557
<211> LENGTH: 21
<212> TYPE: RNA
<213> ORGANISM: Artificial Sequence
<220> FEATURE:
<223> OTHER INFORMATION: asiRNA

<400> SEQUENCE: 557
uacuucuguu ucccuucagc g    21

<210> SEQ ID NO 558
<211> LENGTH: 21
<212> TYPE: RNA
<213> ORGANISM: Artificial Sequence

```
<220> FEATURE:
<223> OTHER INFORMATION: asiRNA

<400> SEQUENCE: 558
acuucuguuu cccuucagcg g                                              21

<210> SEQ ID NO 559
<211> LENGTH: 21
<212> TYPE: RNA
<213> ORGANISM: Artificial Sequence
<220> FEATURE:
<223> OTHER INFORMATION: asiRNA

<400> SEQUENCE: 559
uucuguuucc cuucagcggc u                                              21

<210> SEQ ID NO 560
<211> LENGTH: 21
<212> TYPE: RNA
<213> ORGANISM: Artificial Sequence
<220> FEATURE:
<223> OTHER INFORMATION: asiRNA

<400> SEQUENCE: 560
uucagcggcu cuuugaaga a                                               21

<210> SEQ ID NO 561
<211> LENGTH: 21
<212> TYPE: RNA
<213> ORGANISM: Artificial Sequence
<220> FEATURE:
<223> OTHER INFORMATION: asiRNA

<400> SEQUENCE: 561
ucagcggcuc uuugaagaa g                                               21

<210> SEQ ID NO 562
<211> LENGTH: 21
<212> TYPE: RNA
<213> ORGANISM: Artificial Sequence
<220> FEATURE:
<223> OTHER INFORMATION: asiRNA

<400> SEQUENCE: 562
agcggcucuu uugaagaaga c                                              21

<210> SEQ ID NO 563
<211> LENGTH: 21
<212> TYPE: RNA
<213> ORGANISM: Artificial Sequence
<220> FEATURE:
<223> OTHER INFORMATION: asiRNA

<400> SEQUENCE: 563
ggcucuuuug aagaagaccu u                                              21

<210> SEQ ID NO 564
<211> LENGTH: 21
<212> TYPE: RNA
<213> ORGANISM: Artificial Sequence
<220> FEATURE:
<223> OTHER INFORMATION: asiRNA

<400> SEQUENCE: 564
gcucuuuuga agaagaccuu g                                              21
```

```
<210> SEQ ID NO 565
<211> LENGTH: 21
<212> TYPE: RNA
<213> ORGANISM: Artificial Sequence
<220> FEATURE:
<223> OTHER INFORMATION: asiRNA

<400> SEQUENCE: 565
cuuuugaaga agaccuugca g                                              21

<210> SEQ ID NO 566
<211> LENGTH: 21
<212> TYPE: RNA
<213> ORGANISM: Artificial Sequence
<220> FEATURE:
<223> OTHER INFORMATION: asiRNA

<400> SEQUENCE: 566
agagucaucc cugcuucaua a                                              21

<210> SEQ ID NO 567
<211> LENGTH: 21
<212> TYPE: RNA
<213> ORGANISM: Artificial Sequence
<220> FEATURE:
<223> OTHER INFORMATION: asiRNA

<400> SEQUENCE: 567
agucaucccu gcuucauaac a                                              21

<210> SEQ ID NO 568
<211> LENGTH: 21
<212> TYPE: RNA
<213> ORGANISM: Artificial Sequence
<220> FEATURE:
<223> OTHER INFORMATION: asiRNA

<400> SEQUENCE: 568
caucccugcu ucauaacauu u                                              21

<210> SEQ ID NO 569
<211> LENGTH: 21
<212> TYPE: RNA
<213> ORGANISM: Artificial Sequence
<220> FEATURE:
<223> OTHER INFORMATION: asiRNA

<400> SEQUENCE: 569
ucccugcuuc auaacauuuc c                                              21

<210> SEQ ID NO 570
<211> LENGTH: 21
<212> TYPE: RNA
<213> ORGANISM: Artificial Sequence
<220> FEATURE:
<223> OTHER INFORMATION: asiRNA

<400> SEQUENCE: 570
cccugcuuca uaacauuucc g                                              21

<210> SEQ ID NO 571
<211> LENGTH: 21
<212> TYPE: RNA
<213> ORGANISM: Artificial Sequence
<220> FEATURE:
<223> OTHER INFORMATION: asiRNA
```

```
<400> SEQUENCE: 571
ggcugacauu cauagccuuc a                                              21

<210> SEQ ID NO 572
<211> LENGTH: 21
<212> TYPE: RNA
<213> ORGANISM: Artificial Sequence
<220> FEATURE:
<223> OTHER INFORMATION: asiRNA

<400> SEQUENCE: 572
gcugacauuc auagccuuca a                                              21

<210> SEQ ID NO 573
<211> LENGTH: 21
<212> TYPE: RNA
<213> ORGANISM: Artificial Sequence
<220> FEATURE:
<223> OTHER INFORMATION: asiRNA

<400> SEQUENCE: 573
gacauucaua gccuucaaug u                                              21

<210> SEQ ID NO 574
<211> LENGTH: 21
<212> TYPE: RNA
<213> ORGANISM: Artificial Sequence
<220> FEATURE:
<223> OTHER INFORMATION: asiRNA

<400> SEQUENCE: 574
cauucauagc cuucaaugug u                                              21

<210> SEQ ID NO 575
<211> LENGTH: 21
<212> TYPE: RNA
<213> ORGANISM: Artificial Sequence
<220> FEATURE:
<223> OTHER INFORMATION: asiRNA

<400> SEQUENCE: 575
cuggcucaau ggcuuccagg a                                              21

<210> SEQ ID NO 576
<211> LENGTH: 21
<212> TYPE: RNA
<213> ORGANISM: Artificial Sequence
<220> FEATURE:
<223> OTHER INFORMATION: asiRNA

<400> SEQUENCE: 576
aaguugcgga agccaggcaa g                                              21

<210> SEQ ID NO 577
<211> LENGTH: 21
<212> TYPE: RNA
<213> ORGANISM: Artificial Sequence
<220> FEATURE:
<223> OTHER INFORMATION: asiRNA

<400> SEQUENCE: 577
uugcggaagc caggcaaggc c                                              21

<210> SEQ ID NO 578
```

```
<211> LENGTH: 21
<212> TYPE: RNA
<213> ORGANISM: Artificial Sequence
<220> FEATURE:
<223> OTHER INFORMATION: asiRNA

<400> SEQUENCE: 578
aaggccuugg cccacuugac c                                                    21

<210> SEQ ID NO 579
<211> LENGTH: 21
<212> TYPE: RNA
<213> ORGANISM: Artificial Sequence
<220> FEATURE:
<223> OTHER INFORMATION: asiRNA

<400> SEQUENCE: 579
aaguagagca uccuggaguu g                                                    21

<210> SEQ ID NO 580
<211> LENGTH: 21
<212> TYPE: RNA
<213> ORGANISM: Artificial Sequence
<220> FEATURE:
<223> OTHER INFORMATION: asiRNA

<400> SEQUENCE: 580
aguagagcau ccuggaguug a                                                    21

<210> SEQ ID NO 581
<211> LENGTH: 21
<212> TYPE: RNA
<213> ORGANISM: Artificial Sequence
<220> FEATURE:
<223> OTHER INFORMATION: asiRNA

<400> SEQUENCE: 581
agagcauccu ggaguugaca u                                                    21

<210> SEQ ID NO 582
<211> LENGTH: 21
<212> TYPE: RNA
<213> ORGANISM: Artificial Sequence
<220> FEATURE:
<223> OTHER INFORMATION: asiRNA

<400> SEQUENCE: 582
acuugugcau gcgguacuca u                                                    21

<210> SEQ ID NO 583
<211> LENGTH: 21
<212> TYPE: RNA
<213> ORGANISM: Artificial Sequence
<220> FEATURE:
<223> OTHER INFORMATION: asiRNA

<400> SEQUENCE: 583
uugugcaugc gguacucauu g                                                    21

<210> SEQ ID NO 584
<211> LENGTH: 21
<212> TYPE: RNA
<213> ORGANISM: Artificial Sequence
<220> FEATURE:
<223> OTHER INFORMATION: asiRNA

<400> SEQUENCE: 584
```

```
caugcgguac ucauugaaaa c                                              21

<210> SEQ ID NO 585
<211> LENGTH: 21
<212> TYPE: RNA
<213> ORGANISM: Artificial Sequence
<220> FEATURE:
<223> OTHER INFORMATION: asiRNA

<400> SEQUENCE: 585
augcgguacu cauugaaaac c                                              21

<210> SEQ ID NO 586
<211> LENGTH: 21
<212> TYPE: RNA
<213> ORGANISM: Artificial Sequence
<220> FEATURE:
<223> OTHER INFORMATION: asiRNA

<400> SEQUENCE: 586
ugcgguacuc auugaaaacc a                                              21

<210> SEQ ID NO 587
<211> LENGTH: 21
<212> TYPE: RNA
<213> ORGANISM: Artificial Sequence
<220> FEATURE:
<223> OTHER INFORMATION: asiRNA

<400> SEQUENCE: 587
auuuggagcc auccaaacuc u                                              21

<210> SEQ ID NO 588
<211> LENGTH: 21
<212> TYPE: RNA
<213> ORGANISM: Artificial Sequence
<220> FEATURE:
<223> OTHER INFORMATION: asiRNA

<400> SEQUENCE: 588
uggagccauc caaacucuug a                                              21

<210> SEQ ID NO 589
<211> LENGTH: 21
<212> TYPE: RNA
<213> ORGANISM: Artificial Sequence
<220> FEATURE:
<223> OTHER INFORMATION: asiRNA

<400> SEQUENCE: 589
gagccaucca aacucuugag a                                              21

<210> SEQ ID NO 590
<211> LENGTH: 21
<212> TYPE: RNA
<213> ORGANISM: Artificial Sequence
<220> FEATURE:
<223> OTHER INFORMATION: asiRNA

<400> SEQUENCE: 590
cgaucgaguu ccuugaugua g                                              21

<210> SEQ ID NO 591
<211> LENGTH: 21
<212> TYPE: RNA
```

```
<213> ORGANISM: Artificial Sequence
<220> FEATURE:
<223> OTHER INFORMATION: asiRNA

<400> SEQUENCE: 591
aucgaguucc uugauguagu u                                              21

<210> SEQ ID NO 592
<211> LENGTH: 21
<212> TYPE: RNA
<213> ORGANISM: Artificial Sequence
<220> FEATURE:
<223> OTHER INFORMATION: asiRNA

<400> SEQUENCE: 592 gaguccuug auguaguuca u                                               21

<210> SEQ ID NO 593
<211> LENGTH: 21
<212> TYPE: RNA
<213> ORGANISM: Artificial Sequence
<220> FEATURE:
<223> OTHER INFORMATION: asiRNA

<400> SEQUENCE: 593
uuccuugaug uaguucauuc g                                              21

<210> SEQ ID NO 594
<211> LENGTH: 21
<212> TYPE: RNA
<213> ORGANISM: Artificial Sequence
<220> FEATURE:
<223> OTHER INFORMATION: asiRNA

<400> SEQUENCE: 594
uguaguucau ucgaaguuca u                                              21

<210> SEQ ID NO 595
<211> LENGTH: 21
<212> TYPE: RNA
<213> ORGANISM: Artificial Sequence
<220> FEATURE:
<223> OTHER INFORMATION: asiRNA

<400> SEQUENCE: 595
guucauucga aguucaucaa a                                              21

<210> SEQ ID NO 596
<211> LENGTH: 21
<212> TYPE: RNA
<213> ORGANISM: Artificial Sequence
<220> FEATURE:
<223> OTHER INFORMATION: asiRNA

<400> SEQUENCE: 596
cauucgaagu ucaucaaaga a                                              21

<210> SEQ ID NO 597
<211> LENGTH: 21
<212> TYPE: RNA
<213> ORGANISM: Artificial Sequence
<220> FEATURE:
<223> OTHER INFORMATION: asiRNA

<400> SEQUENCE: 597
uuugauuuuu cagcccaucc a                                              21
```

<210> SEQ ID NO 598
<211> LENGTH: 21
<212> TYPE: RNA
<213> ORGANISM: Artificial Sequence
<220> FEATURE:
<223> OTHER INFORMATION: asiRNA

<400> SEQUENCE: 598 gauuuucag cccauccacu g                                          21

<210> SEQ ID NO 599
<211> LENGTH: 21
<212> TYPE: RNA
<213> ORGANISM: Artificial Sequence
<220> FEATURE:
<223> OTHER INFORMATION: asiRNA

<400> SEQUENCE: 599
cccauccacu ggauaaugc u                                          21

<210> SEQ ID NO 600
<211> LENGTH: 21
<212> TYPE: RNA
<213> ORGANISM: Artificial Sequence
<220> FEATURE:
<223> OTHER INFORMATION: asiRNA

<400> SEQUENCE: 600
auccacugga auaaugcuga a                                         21

<210> SEQ ID NO 601
<211> LENGTH: 21
<212> TYPE: RNA
<213> ORGANISM: Artificial Sequence
<220> FEATURE:
<223> OTHER INFORMATION: asiRNA

<400> SEQUENCE: 601
ccacuggaau aaugcugaag a                                         21

<210> SEQ ID NO 602
<211> LENGTH: 21
<212> TYPE: RNA
<213> ORGANISM: Artificial Sequence
<220> FEATURE:
<223> OTHER INFORMATION: asiRNA

<400> SEQUENCE: 602
cuggaauaau gcugaagaga g                                         21

<210> SEQ ID NO 603
<211> LENGTH: 21
<212> TYPE: RNA
<213> ORGANISM: Artificial Sequence
<220> FEATURE:
<223> OTHER INFORMATION: asiRNA

<400> SEQUENCE: 603
gaauaaugcu gaagagagca g                                         21

<210> SEQ ID NO 604
<211> LENGTH: 21
<212> TYPE: RNA
<213> ORGANISM: Artificial Sequence
<220> FEATURE:

```
<223> OTHER INFORMATION: asiRNA

<400> SEQUENCE: 604
augcugaaga gagcagugcu u                                              21

<210> SEQ ID NO 605
<211> LENGTH: 21
<212> TYPE: RNA
<213> ORGANISM: Artificial Sequence
<220> FEATURE:
<223> OTHER INFORMATION: asiRNA

<400> SEQUENCE: 605
gaagagagca gugcuuucau g                                              21

<210> SEQ ID NO 606
<211> LENGTH: 21
<212> TYPE: RNA
<213> ORGANISM: Artificial Sequence
<220> FEATURE:
<223> OTHER INFORMATION: asiRNA

<400> SEQUENCE: 606
agagagcagu gcuuucaugc a                                              21

<210> SEQ ID NO 607
<211> LENGTH: 21
<212> TYPE: RNA
<213> ORGANISM: Artificial Sequence
<220> FEATURE:
<223> OTHER INFORMATION: asiRNA

<400> SEQUENCE: 607
gagcagugcu uucaugcaca g                                              21

<210> SEQ ID NO 608
<211> LENGTH: 21
<212> TYPE: RNA
<213> ORGANISM: Artificial Sequence
<220> FEATURE:
<223> OTHER INFORMATION: asiRNA

<400> SEQUENCE: 608
cagugcuuuc augcacagga a                                              21

<210> SEQ ID NO 609
<211> LENGTH: 21
<212> TYPE: RNA
<213> ORGANISM: Artificial Sequence
<220> FEATURE:
<223> OTHER INFORMATION: asiRNA

<400> SEQUENCE: 609
cuuucaugca caggaauucc u                                              21

<210> SEQ ID NO 610
<211> LENGTH: 21
<212> TYPE: RNA
<213> ORGANISM: Artificial Sequence
<220> FEATURE:
<223> OTHER INFORMATION: asiRNA

<400> SEQUENCE: 610
ucaugcacag gaauuccugg g                                              21
```

```
<210> SEQ ID NO 611
<211> LENGTH: 21
<212> TYPE: RNA
<213> ORGANISM: Artificial Sequence
<220> FEATURE:
<223> OTHER INFORMATION: asiRNA

<400> SEQUENCE: 611
augcacagga auuccugggg g                                              21

<210> SEQ ID NO 612
<211> LENGTH: 21
<212> TYPE: RNA
<213> ORGANISM: Artificial Sequence
<220> FEATURE:
<223> OTHER INFORMATION: asiRNA

<400> SEQUENCE: 612
uccaggagcu uggugagcug g                                              21

<210> SEQ ID NO 613
<211> LENGTH: 21
<212> TYPE: RNA
<213> ORGANISM: Artificial Sequence
<220> FEATURE:
<223> OTHER INFORMATION: asiRNA

<400> SEQUENCE: 613
agcuggguga gcugguagaa g                                              21

<210> SEQ ID NO 614
<211> LENGTH: 21
<212> TYPE: RNA
<213> ORGANISM: Artificial Sequence
<220> FEATURE:
<223> OTHER INFORMATION: asiRNA

<400> SEQUENCE: 614
cuuggugagc ugguagaagc g                                              21

<210> SEQ ID NO 615
<211> LENGTH: 21
<212> TYPE: RNA
<213> ORGANISM: Artificial Sequence
<220> FEATURE:
<223> OTHER INFORMATION: asiRNA

<400> SEQUENCE: 615
gacuugauua gcaggucaaa a                                              21

<210> SEQ ID NO 616
<211> LENGTH: 21
<212> TYPE: RNA
<213> ORGANISM: Artificial Sequence
<220> FEATURE:
<223> OTHER INFORMATION: asiRNA

<400> SEQUENCE: 616
acuugauuag caggucaaaa g                                              21

<210> SEQ ID NO 617
<211> LENGTH: 21
<212> TYPE: RNA
<213> ORGANISM: Artificial Sequence
<220> FEATURE:
<223> OTHER INFORMATION: asiRNA
```

```
<400> SEQUENCE: 617
ugauuagcag gucaaaagug a                                              21

<210> SEQ ID NO 618
<211> LENGTH: 21
<212> TYPE: RNA
<213> ORGANISM: Artificial Sequence
<220> FEATURE:
<223> OTHER INFORMATION: asiRNA

<400> SEQUENCE: 618
auuagcaggu caaaagugaa c                                              21

<210> SEQ ID NO 619
<211> LENGTH: 21
<212> TYPE: RNA
<213> ORGANISM: Artificial Sequence
<220> FEATURE:
<223> OTHER INFORMATION: asiRNA

<400> SEQUENCE: 619
agcaggucaa aagugaacug a                                              21

<210> SEQ ID NO 620
<211> LENGTH: 21
<212> TYPE: RNA
<213> ORGANISM: Artificial Sequence
<220> FEATURE:
<223> OTHER INFORMATION: asiRNA

<400> SEQUENCE: 620
gcaggucaaa agugaacuga u                                              21

<210> SEQ ID NO 621
<211> LENGTH: 21
<212> TYPE: RNA
<213> ORGANISM: Artificial Sequence
<220> FEATURE:
<223> OTHER INFORMATION: asiRNA

<400> SEQUENCE: 621
ggucaaaagu gaacugaugc a                                              21

<210> SEQ ID NO 622
<211> LENGTH: 21
<212> TYPE: RNA
<213> ORGANISM: Artificial Sequence
<220> FEATURE:
<223> OTHER INFORMATION: asiRNA

<400> SEQUENCE: 622
caaaagugaa cugaugcagc u                                              21

<210> SEQ ID NO 623
<211> LENGTH: 21
<212> TYPE: RNA
<213> ORGANISM: Artificial Sequence
<220> FEATURE:
<223> OTHER INFORMATION: asiRNA

<400> SEQUENCE: 623
aagugaacug augcagcucu c                                              21

<210> SEQ ID NO 624
<211> LENGTH: 21
```

```
<212> TYPE: RNA
<213> ORGANISM: Artificial Sequence
<220> FEATURE:
<223> OTHER INFORMATION: asiRNA

<400> SEQUENCE: 624
agugaacuga ugcagcucuc u                                              21

<210> SEQ ID NO 625
<211> LENGTH: 21
<212> TYPE: RNA
<213> ORGANISM: Artificial Sequence
<220> FEATURE:
<223> OTHER INFORMATION: asiRNA

<400> SEQUENCE: 625
guguggaaau agaugggcuu g                                              21

<210> SEQ ID NO 626
<211> LENGTH: 21
<212> TYPE: RNA
<213> ORGANISM: Artificial Sequence
<220> FEATURE:
<223> OTHER INFORMATION: asiRNA

<400> SEQUENCE: 626
uguggaaaua gaugggcuug a                                              21

<210> SEQ ID NO 627
<211> LENGTH: 21
<212> TYPE: RNA
<213> ORGANISM: Artificial Sequence
<220> FEATURE:
<223> OTHER INFORMATION: asiRNA

<400> SEQUENCE: 627
uggaaauaga ugggcuugac u                                              21

<210> SEQ ID NO 628
<211> LENGTH: 21
<212> TYPE: RNA
<213> ORGANISM: Artificial Sequence
<220> FEATURE:
<223> OTHER INFORMATION: asiRNA

<400> SEQUENCE: 628
aaauagaugg gcuugacuuu c                                              21

<210> SEQ ID NO 629
<211> LENGTH: 21
<212> TYPE: RNA
<213> ORGANISM: Artificial Sequence
<220> FEATURE:
<223> OTHER INFORMATION: asiRNA

<400> SEQUENCE: 629
augggcuuga cuuucccaga a                                              21

<210> SEQ ID NO 630
<211> LENGTH: 21
<212> TYPE: RNA
<213> ORGANISM: Artificial Sequence
<220> FEATURE:
<223> OTHER INFORMATION: asiRNA

<400> SEQUENCE: 630
```
ggcuugacuu ucccagaaag g                    21

<210> SEQ ID NO 631
<211> LENGTH: 21
<212> TYPE: RNA
<213> ORGANISM: Artificial Sequence
<220> FEATURE:
<223> OTHER INFORMATION: asiRNA

<400> SEQUENCE: 631
uugacuuucc cagaaaggau c                    21

<210> SEQ ID NO 632
<211> LENGTH: 21
<212> TYPE: RNA
<213> ORGANISM: Artificial Sequence
<220> FEATURE:
<223> OTHER INFORMATION: asiRNA

<400> SEQUENCE: 632 acuucccag aaaggaucuu g                     21

<210> SEQ ID NO 633
<211> LENGTH: 21
<212> TYPE: RNA
<213> ORGANISM: Artificial Sequence
<220> FEATURE:
<223> OTHER INFORMATION: asiRNA

<400> SEQUENCE: 633
ccagaaagga ucuugggcac u                    21

<210> SEQ ID NO 634
<211> LENGTH: 21
<212> TYPE: RNA
<213> ORGANISM: Artificial Sequence
<220> FEATURE:
<223> OTHER INFORMATION: asiRNA

<400> SEQUENCE: 634
gaaaggaucu ugggcacuug c                    21

<210> SEQ ID NO 635
<211> LENGTH: 21
<212> TYPE: RNA
<213> ORGANISM: Artificial Sequence
<220> FEATURE:
<223> OTHER INFORMATION: asiRNA

<400> SEQUENCE: 635
aggaucuugg gcacuugcac a                    21

<210> SEQ ID NO 636
<211> LENGTH: 21
<212> TYPE: RNA
<213> ORGANISM: Artificial Sequence
<220> FEATURE:
<223> OTHER INFORMATION: asiRNA

<400> SEQUENCE: 636
aucuggggca cuugcacaga g                    21

<210> SEQ ID NO 637
<211> LENGTH: 21
<212> TYPE: RNA
<213> ORGANISM: Artificial Sequence

```
<220> FEATURE:
<223> OTHER INFORMATION: asiRNA

<400> SEQUENCE: 637
ggcacuugca cagagaugau c                                              21

<210> SEQ ID NO 638
<211> LENGTH: 21
<212> TYPE: RNA
<213> ORGANISM: Artificial Sequence
<220> FEATURE:
<223> OTHER INFORMATION: asiRNA

<400> SEQUENCE: 638
acuugcacag agaugaucuc u                                              21

<210> SEQ ID NO 639
<211> LENGTH: 21
<212> TYPE: RNA
<213> ORGANISM: Artificial Sequence
<220> FEATURE:
<223> OTHER INFORMATION: asiRNA

<400> SEQUENCE: 639
ugcacagaga ugaucucugc c                                              21

<210> SEQ ID NO 640
<211> LENGTH: 21
<212> TYPE: RNA
<213> ORGANISM: Artificial Sequence
<220> FEATURE:
<223> OTHER INFORMATION: asiRNA

<400> SEQUENCE: 640
acagagauga ucucugccau c                                              21

<210> SEQ ID NO 641
<211> LENGTH: 21
<212> TYPE: RNA
<213> ORGANISM: Artificial Sequence
<220> FEATURE:
<223> OTHER INFORMATION: asiRNA

<400> SEQUENCE: 641
uuuuuuagug ccagugaaca u                                              21

<210> SEQ ID NO 642
<211> LENGTH: 21
<212> TYPE: RNA
<213> ORGANISM: Artificial Sequence
<220> FEATURE:
<223> OTHER INFORMATION: asiRNA

<400> SEQUENCE: 642
uuuuuagugc cagugaacau a                                              21

<210> SEQ ID NO 643
<211> LENGTH: 21
<212> TYPE: RNA
<213> ORGANISM: Artificial Sequence
<220> FEATURE:
<223> OTHER INFORMATION: asiRNA

<400> SEQUENCE: 643
uuuagugcca gugaacauac a                                              21
```

```
<210> SEQ ID NO 644
<211> LENGTH: 21
<212> TYPE: RNA
<213> ORGANISM: Artificial Sequence
<220> FEATURE:
<223> OTHER INFORMATION: asiRNA

<400> SEQUENCE: 644
agugccagug aacauacaua a                                              21

<210> SEQ ID NO 645
<211> LENGTH: 21
<212> TYPE: RNA
<213> ORGANISM: Artificial Sequence
<220> FEATURE:
<223> OTHER INFORMATION: asiRNA

<400> SEQUENCE: 645
ugccagugaa cauacauaaa a                                              21

<210> SEQ ID NO 646
<211> LENGTH: 21
<212> TYPE: RNA
<213> ORGANISM: Artificial Sequence
<220> FEATURE:
<223> OTHER INFORMATION: asiRNA

<400> SEQUENCE: 646
ccagugaaca uacauaaaaa u                                              21

<210> SEQ ID NO 647
<211> LENGTH: 21
<212> TYPE: RNA
<213> ORGANISM: Artificial Sequence
<220> FEATURE:
<223> OTHER INFORMATION: asiRNA

<400> SEQUENCE: 647
accucagcaa cuacccaaag g                                              21

<210> SEQ ID NO 648
<211> LENGTH: 21
<212> TYPE: RNA
<213> ORGANISM: Artificial Sequence
<220> FEATURE:
<223> OTHER INFORMATION: asiRNA

<400> SEQUENCE: 648
ccucagcaac uacccaaagg a                                              21

<210> SEQ ID NO 649
<211> LENGTH: 21
<212> TYPE: RNA
<213> ORGANISM: Artificial Sequence
<220> FEATURE:
<223> OTHER INFORMATION: asiRNA

<400> SEQUENCE: 649
cagcaacuac ccaaaggaca g                                              21

<210> SEQ ID NO 650
<211> LENGTH: 21
<212> TYPE: RNA
<213> ORGANISM: Artificial Sequence
<220> FEATURE:
<223> OTHER INFORMATION: asiRNA
```

```
<400> SEQUENCE: 650
agcaacuacc caaaggacag a                                              21

<210> SEQ ID NO 651
<211> LENGTH: 21
<212> TYPE: RNA
<213> ORGANISM: Artificial Sequence
<220> FEATURE:
<223> OTHER INFORMATION: asiRNA

<400> SEQUENCE: 651
aucaugugga ugguggacau a                                              21

<210> SEQ ID NO 652
<211> LENGTH: 21
<212> TYPE: RNA
<213> ORGANISM: Artificial Sequence
<220> FEATURE:
<223> OTHER INFORMATION: asiRNA

<400> SEQUENCE: 652
caaagaggca cuaaugcuug c                                              21

<210> SEQ ID NO 653
<211> LENGTH: 21
<212> TYPE: RNA
<213> ORGANISM: Artificial Sequence
<220> FEATURE:
<223> OTHER INFORMATION: asiRNA

<400> SEQUENCE: 653
aaagaggcac uaaugcuugc u                                              21

<210> SEQ ID NO 654
<211> LENGTH: 21
<212> TYPE: RNA
<213> ORGANISM: Artificial Sequence
<220> FEATURE:
<223> OTHER INFORMATION: asiRNA

<400> SEQUENCE: 654
aagaggcacu aaugcuugcu c                                              21

<210> SEQ ID NO 655
<211> LENGTH: 21
<212> TYPE: RNA
<213> ORGANISM: Artificial Sequence
<220> FEATURE:
<223> OTHER INFORMATION: asiRNA

<400> SEQUENCE: 655
agaggcacua augcuugcuc c                                              21

<210> SEQ ID NO 656
<211> LENGTH: 21
<212> TYPE: RNA
<213> ORGANISM: Artificial Sequence
<220> FEATURE:
<223> OTHER INFORMATION: asiRNA

<400> SEQUENCE: 656
auaagcuaac augggcacua g                                              21

<210> SEQ ID NO 657
```

```
<211> LENGTH: 21
<212> TYPE: RNA
<213> ORGANISM: Artificial Sequence
<220> FEATURE:
<223> OTHER INFORMATION: asiRNA

<400> SEQUENCE: 657
ccaacaaaca aguuucugcc a                                              21

<210> SEQ ID NO 658
<211> LENGTH: 21
<212> TYPE: RNA
<213> ORGANISM: Artificial Sequence
<220> FEATURE:
<223> OTHER INFORMATION: asiRNA

<400> SEQUENCE: 658
acaaacaagu uucugccauu u                                              21

<210> SEQ ID NO 659
<211> LENGTH: 21
<212> TYPE: RNA
<213> ORGANISM: Artificial Sequence
<220> FEATURE:
<223> OTHER INFORMATION: asiRNA

<400> SEQUENCE: 659
aacaaguuuc ugccauuuuu a                                              21

<210> SEQ ID NO 660
<211> LENGTH: 21
<212> TYPE: RNA
<213> ORGANISM: Artificial Sequence
<220> FEATURE:
<223> OTHER INFORMATION: asiRNA

<400> SEQUENCE: 660
acaaguuucu gccauuuuua a                                              21

<210> SEQ ID NO 661
<211> LENGTH: 21
<212> TYPE: RNA
<213> ORGANISM: Artificial Sequence
<220> FEATURE:
<223> OTHER INFORMATION: asiRNA

<400> SEQUENCE: 661
agcaacaaaa gauuccaaga u                                              21

<210> SEQ ID NO 662
<211> LENGTH: 21
<212> TYPE: RNA
<213> ORGANISM: Artificial Sequence
<220> FEATURE:
<223> OTHER INFORMATION: asiRNA

<400> SEQUENCE: 662
gcaacaaaag auuccaagau u                                              21

<210> SEQ ID NO 663
<211> LENGTH: 21
<212> TYPE: RNA
<213> ORGANISM: Artificial Sequence
<220> FEATURE:
<223> OTHER INFORMATION: asiRNA

<400> SEQUENCE: 663
```
agagaacaga acacuagcgc u                                          21

<210> SEQ ID NO 664
<211> LENGTH: 21
<212> TYPE: RNA
<213> ORGANISM: Artificial Sequence
<220> FEATURE:
<223> OTHER INFORMATION: asiRNA

<400> SEQUENCE: 664
gagaacagaa cacuagcgcu u                                          21

<210> SEQ ID NO 665
<211> LENGTH: 20
<212> TYPE: DNA
<213> ORGANISM: Artificial Sequence
<220> FEATURE:
<223> OTHER INFORMATION: Primer

<400> SEQUENCE: 665
gagtcaacgg atttggtcgt                                            20

<210> SEQ ID NO 666
<211> LENGTH: 20
<212> TYPE: DNA
<213> ORGANISM: Artificial Sequence
<220> FEATURE:
<223> OTHER INFORMATION: Primer

<400> SEQUENCE: 666
gacaagcttc ccgttctcag                                            20

<210> SEQ ID NO 667
<211> LENGTH: 20
<212> TYPE: DNA
<213> ORGANISM: Artificial Sequence
<220> FEATURE:
<223> OTHER INFORMATION: Primer

<400> SEQUENCE: 667
ggggctagac tgctcaactg                                            20

<210> SEQ ID NO 668
<211> LENGTH: 20
<212> TYPE: DNA
<213> ORGANISM: Artificial Sequence
<220> FEATURE:
<223> OTHER INFORMATION: Primer

<400> SEQUENCE: 668
gccaagtttt ggctgaagag                                            20

<210> SEQ ID NO 669
<211> LENGTH: 2350
<212> TYPE: DNA
<213> ORGANISM: Artificial Sequence
<220> FEATURE:
<223> OTHER INFORMATION: NCBI Reference Sequence NM_001047.3

<400> SEQUENCE: 669
ttactgcggc cccggcgtgg gtggggcgct tgcaggtccc tccccgcgca agtgctcgcc    60
ccgcccccgg ggccgcaccc acagcccggg ctaccccgga gaagcctgac ttgagaaccc   120
tttctgcaga gtcccggcag tgcgggactc cggtagccgc ccctccggta gccgcccctc   180

```
ctgccccgc gccgccgccc tatatgttgc ccgccgcggc ctctggggca tggagcacgc    240
tgcccagccc tggcgatggc aacggcgacg ggggtggcgg aggagcgcct gctggccgcg    300
ctcgcctacc tgcagtgcgc cgtgggctgc gcggtcttcg cgcgcaatcg tcagacgaac    360
tcagtgtacg gccgccacgc gctgcccagc cacaggctcc gagtgccggc gcgggccgcc    420
tgggtggtgc aggagctgcc ctcgctggcc ctgccgctct accagtacgc cagcgagtcc    480
gccccgcgtc tccgcagcgc gcccaactgc atcctcctgg ccatgttcct cgtccactac    540
gggcatcggt gcttaattta cccatttctg atgcgaggag gaaagcctat gccactgttg    600
gcgtgtacaa tggcgattat gttctgtacc tgtaacggct atttgcaaag cagatacttg    660
agccattgtg cagtgtatgc tgatgactgg gtaacagatc cccgttttct aataggtttt    720
ggcttgtggt taacgggcat gttgataaac atccattcag atcatatcct aaggaatctc    780
agaaaaccag agatactgga atacaaaata ccaaggggag gcttatttga atacgtaact    840
gcagccaact attttggaga atcatggagt ggtgtggct atgccctggc cagctggtct    900
gtccaaggcg cggcttttgc tttcttcacg ttttgttttt tatctggtag agcaaaagag    960
catcatgagt ggtacctccg gaaatttgaa gagtatccaa agttcagaaa aattataatt    1020
ccattttgt tttaagtgcg tttttcatga aattatcttc aacttgaagc tttccaatgg    1080
cgcttctcta tggactttgt aaataagtta tatctttgta attttcctgc tactttatca    1140
ttttcaagat gtcctctagg aattttttt ctagtaattt tgcaatctac ctaataagta    1200
cctaaatacg ctgaaatgga ggttgaatat cctactgtgt aacaggtcag aatttcaagc    1260
tctgggtaat aactgctgat atttttcta atttcaaatt taccctcttt ggctatgtct    1320
tgccaagtgt gtatgagact agactttaca actgtctttg atggcatttt cagaacaata    1380
aatgtcacaa tcccttctat agcccctac agtgatctct tcaaggtcaa ctgcagtgtt    1440
gcttccctcc ccctataggg ctggaatctg tctaggagcc ctctctcgga ggccacagag    1500
gctgggggta gccattgtgc agtcatggcc cggggaaac ttgccaacct tcgtgtcagg    1560
tgctgtgtgt aagtggagaa cttggggata gaggaggaag ctcctcgtgg cccttccaag    1620
gtgaggcaaa ggcatctgga cttgttccag cccagcccac cgggtgacat caccgggcag    1680
ggaggggtgc tggtggtggt tcatacggag taagctgctc tgcctgtgtg agtggctcct    1740
gggccctaaa caggcacctt taggccatgg gtcactcacc gtgagccatc aatgtgctct    1800
ggtctgacat ggtttctctc tgtcttctag tctagaccta gttttttgt tctgttcccc    1860
acgtatggat atagtagaga ttgttgtctg tgaaatttct cttttgtaga ttttgagttt    1920
tcccttgtag tgtaaagaat gatcactttc tgtaacaata acaagaccac tttttaagat    1980
ttatcctgtt tgttctttgt tgattgaaac ataataattg ttaaaattct ctacagcctt    2040
ctttttcttc catagctaat cttccttcta atagttttg ctttctgttt tgctgttgtt    2100
gctttgcaaa gctttcccct catagcctgt acctgttatc aatataaaat aatcttcctg    2160
ttgaatgctt catgacttga attctacttt gataaaaaca ttgccatact gctttttatc    2220
ttgatgaatt catctggcat tgctttgcct tatcatctca tctggagttt ttaaatgcca    2280
tttgtttcag ttgtctttaa caacataata aatagacttt gccatttaaa aaaaaaaaa    2340
aaaaaaaaaa                                                          2350
```

<210> SEQ ID NO 670
<211> LENGTH: 2183
<212> TYPE: DNA
<213> ORGANISM: Artificial Sequence
<220> FEATURE:
<223> OTHER INFORMATION: NCBI Reference Sequence NM_001324322.1

<400> SEQUENCE: 670

| | | | | | |
|---|---|---|---|---|---|
| ttactgcggc | cccggcgtgg | gtggggcgct | tgcaggtccc | tccccgcgca | agtgctcgcc | 60 |
| ccgcccccgg | ggccgcaccc | acagcccggg | ctacccccgga | gaagcctgac | ttgagaaccc | 120 |
| tttctgcaga | gtcccggcag | tgcgggactc | cggtagccgc | ccctccggta | gccgcccctc | 180 |
| ctgccccgc | gccgccgccc | tatatgttgc | ccgccgcgcc | ctctgggca | tggagcacgc | 240 |
| tgcccagccc | tggcgatggc | aacggcgacg | ggggtggcgg | aggagcgcct | gctggccgcg | 300 |
| ctcgcctacc | tgcagtgcgc | cgtgggctgc | gcggtcttcg | cgcgcaatcg | tcagacgaac | 360 |
| tcagtgtacg | gccgccacgc | gctgcccagc | cacaggctcc | gagtgccggc | gcgggccgcc | 420 |
| tgggtggtgc | aggagctgcc | ctcgctggcc | ctgccgctct | accagtacgc | cagcgagtcc | 480 |
| gccccgcgtc | tccgcagcgc | gcccaactgc | atcctcctgg | ccatgttcct | cgtccactac | 540 |
| gggcatcggt | tttggcttgt | ggttaacggg | catgttgata | aacatccatt | cagatcatat | 600 |
| cctaaggaat | ctcagaaaac | caggagatac | tggatacaaa | ataccaaggg | gaggcttatt | 660 |
| tgaatacgta | actgcagcca | actatttttgg | agaaatcatg | gagtggtgtg | gctatgccct | 720 |
| ggccagctgg | tctgtccaag | gcgcggcttt | tgctttcttc | acgttttgtt | ttttatctgg | 780 |
| tagagcaaaa | gagcatcatg | agtggtacct | ccggaaattt | gaagagtatc | caaagttcag | 840 |
| aaaaattata | attccatttt | tgttttaagt | gcgttttca | tgaaattatc | ttcaacttga | 900 |
| agctttccaa | tggcgcttct | ctatggactt | tgtaaataag | ttatatcttt | gtaattttcc | 960 |
| tgctacttta | tcattttcaa | gatgtcctct | aggaattttt | tttctagtaa | ttttgcaatc | 1020 |
| tacctaataa | gtacctaaat | acgctgaaat | ggaggttgaa | tatcctactg | tgtaacaggt | 1080 |
| cagaatttca | agctctgggt | aataactgct | gatatttttt | ctaatttcaa | atttacctct | 1140 |
| tttggctatg | tcttgccaag | tgtgtatgag | actagacttt | acaactgtct | ttgatggcat | 1200 |
| tttcagaaca | ataaatgtca | caatcccttc | tatagccccc | tacagtgatc | tcttcaaggt | 1260 |
| caactgcagt | gttgcttccc | tccccctata | gggctggaat | ctgtctagga | gccctctctc | 1320 |
| ggaggccaca | gaggctgggg | gtagccattg | tgcagtcatg | gccgggggga | aacttgccaa | 1380 |
| ccttcgtgtc | aggtgctgtg | tgtaagtgga | gaacttgggg | atagaggagg | aagctcctcg | 1440 |
| tggcccttcc | aaggtgaggc | aaaggcatct | ggacttgttc | cagcccagcc | caccgggtga | 1500 |
| catcaccggg | cagggagggg | tgctggtggt | ggttcatacg | gagtaagctg | ctctgcctgt | 1560 |
| gtgagtggct | cctgggccct | aaacaggcac | ctttaggcca | tgggtcactc | accgtgagcc | 1620 |
| atcaatgtgc | tctggtctga | catggtttct | ctctgtcttc | tagtctagac | ctagttttttt | 1680 |
| tgttctgttc | cccacgtatg | gatatagtag | agattgttgt | ctgtgaaatt | tctcttttgt | 1740 |
| agatttttgag | ttttcccttg | tagtgtaaag | aatgatcact | ttctgtaaca | ataacaagac | 1800 |
| cacttttttaa | gatttatcct | gtttgttctt | tgttgattga | aacataataa | ttgttaaaat | 1860 |
| tctctacagc | cttctttttc | ttccatagct | aatcttcctt | ctaatagttt | ttgctttctg | 1920 |
| ttttgctgtt | gttgctttgc | aaagctttcc | cctcatagcc | tgtacctgtt | atcaatataa | 1980 |
| aataatcttc | ctgttgaatg | cttcatgact | tgaattctac | tttgataaaa | acattgccat | 2040 |
| actgcttttt | atcttgatga | attcatctgg | cattgctttg | ccttatcatc | tcatctggag | 2100 |
| tttttaaatg | ccatttgttt | cagttgtctt | taacaacata | ataaatagac | tttgccattt | 2160 |
| aaaaaaaaaa | aaaaaaaaa | aaa | | | | 2183 |

<210> SEQ ID NO 671
<211> LENGTH: 2852
<212> TYPE: DNA
<213> ORGANISM: Artificial Sequence
<220> FEATURE:
<223> OTHER INFORMATION: NCBI Reference Sequence NM_001324323.1

<400> SEQUENCE: 671

| | | | | | |
|---|---|---|---|---|---|
| ttactgcggc | cccggcgtgg | gtggggcgct | tgcaggtccc | tccccgcgca | agtgctcgcc | 60 |
| ccgcccccgg | ggccgcaccc | acagcccggg | ctaccccgga | gaagcctgac | ttgagaaccc | 120 |
| tttctgcaga | gtcccggcag | tgcgggactc | cggtagccgc | ccctccggta | gccgcccctc | 180 |
| ctgccccccgc | gccgccgccc | tatatgttgc | ccgccgcggc | ctctggggca | tggagcacgc | 240 |
| tgcccagccc | tggcgatggc | aacgcgacgg | ggggtggcgg | aggagcgcct | gctgccgcg | 300 |
| ctcgcctacc | tgcagtgcgc | cgtgggctgc | gcggtcttcg | cgcgcaatcg | tcagacgaac | 360 |
| tcagtgtacg | gccgccacgc | gctgcccagc | cacaggctcc | gagtgccggc | gcgggccgcc | 420 |
| tgggtggtgc | aggagctgcc | ctcgctggcc | ctgccgctct | accagtacgc | cagcgagtcc | 480 |
| gccccgcgtc | tccgcagcgc | gcccaactgc | atcctcctgg | ccatgttcct | cgtccactac | 540 |
| gggcatcgga | aatgttggta | tgcaagcact | tgcagtgtgc | ctacatccca | aatgccagcc | 600 |
| catggtaccc | attgtctgcc | cggatctgaa | tcatgattcc | aagacgcaga | gagaaattgc | 660 |
| tgggattcgt | tgttcttatt | cattgcttgg | caacactgca | gcttccagga | gaatacccac | 720 |
| ctcactgatg | acacaacatc | tgaatgcaca | cttactggcc | aacacgtgct | ttgctgtaaa | 780 |
| tcagtatgaa | gtcttcctag | gggtcctggc | ctgaatgaga | tgagaacctt | ggaggctgct | 840 |
| tttgactcat | gtgaatgtct | tccccaggag | ttaagtggga | gtgctgggga | gagagtggct | 900 |
| tgaggatgca | cagccagcat | gacactacta | ttatgtgatt | actgtcgacg | ttcataacca | 960 |
| taactaatga | ctaattatga | ctttaccctg | gcgcacatgg | tcagaatgga | aacaaataac | 1020 |
| aagctttaca | gttttcctg | ctctattaag | gtgcttaatt | tacccatttc | tgatgcgagg | 1080 |
| aggaaagcct | atgccactgt | tggcgtgtac | aatggcgatt | atgttctgta | cctgtaacgg | 1140 |
| ctatttgcaa | agcagatact | tgagccattg | tgcagtgtat | gctgatgact | gggtaacaga | 1200 |
| tccccgtttt | ctaataggtt | ttggcttgtg | gttaacgggc | atgttgataa | acatccattc | 1260 |
| agatcatatc | ctaaggaatc | tcagaaaacc | aggagatact | ggatacaaaa | taccaagggg | 1320 |
| aggcttattt | gaatacgtaa | ctgcagccaa | ctattttgga | gaaatcatgg | agtggtgtgg | 1380 |
| ctatgccctg | gccagctggt | ctgtccaagg | cgcggctttt | gctttcttca | cgttttgttt | 1440 |
| tttatctggt | agagcaaaag | agcatcatga | gtggtacctc | cggaaatttg | aagagtatcc | 1500 |
| aaagttcaga | aaaattataa | ttccattttt | gttttaagtg | cgttttcat | gaaattatct | 1560 |
| tcaacttgaa | gctttccaat | ggcgcttctc | tatggacttt | gtaaataagt | tatatctttg | 1620 |
| taattttcct | gctactttat | cattttcaag | atgtcctcta | ggaatttttt | ttctagtaat | 1680 |
| tttgcaatct | acctaataag | tacctaaata | cgctgaaatg | gaggttgaat | atcctactgt | 1740 |
| gtaacaggtc | agaatttcaa | gctctgggta | ataactgctg | atattttttc | taatttcaaa | 1800 |
| tttacctctt | ttggctatgt | cttgccaagt | gtgtatgaga | ctagacttta | caactgtctt | 1860 |
| tgatggcatt | ttcagaacaa | taaatgtcac | aatcccttct | atagccccct | acagtgatct | 1920 |
| cttcaaggtc | aactgcagtg | ttgcttccct | cccctatag | ggctggaatc | tgtctaggag | 1980 |
| ccctctctcg | gaggccacag | aggctggggg | tagccattgt | gcagtcatgg | cccgggggaa | 2040 |
| acttgccaac | cttcgtgtca | ggtgctgtgt | gtaagtggag | aacttgggga | tagaggagga | 2100 |

```
agctcctcgt ggcccttcca aggtgaggca aaggcatctg gacttgttcc agcccagccc    2160
accgggtgac atcaccgggc agggaggggt gctggtggtg gttcatacgg agtaagctgc    2220
tctgcctgtg tgagtggctc ctgggcccta aacaggcacc tttaggccat gggtcactca    2280
ccgtgagcca tcaatgtgct ctggtctgac atggtttctc tctgtcttct agtctagacc    2340
tagttttttt gttctgttcc ccacgtatgg atatagtaga gattgttgtc tgtgaaattt    2400
ctcttttgta gattttgagt tttcccttgt agtgtaaaga atgatcactt tctgtaacaa    2460
taacaagacc acttttttaag atttatcctg tttgttcttt gttgattgaa acataataat    2520
tgttaaaatt ctctacagcc ttcttttcct tccatagcta atcttcctc taatagtttt    2580 tgctttctgt tttgctgttg ttgctttgca aagctttccc ctcatagcct gtacctgtta    2640
tcaatataaa ataatcttcc tgttgaatgc ttcatgactt gaattctact ttgataaaaa    2700
cattgccata ctgcttttta tcttgatgaa ttcatctggc attgctttgc cttatcatct    2760
catctggagt ttttaaatgc catttgtttc agttgtcttt aacaacataa taaatagact    2820
ttgccattta aaaaaaaaaa aaaaaaaaaa aa                                   2852
```

<210> SEQ ID NO 672
<211> LENGTH: 2446
<212> TYPE: DNA
<213> ORGANISM: Artificial Sequence
<220> FEATURE:
<223> OTHER INFORMATION: NCBI Reference Sequence NM_000348.3

<400> SEQUENCE: 672

```
tccataaagg ggttgcgggg gccgcgctct cttctgggag ggcagcggcc accggcgagg      60
aacacggcgc gatgcaggtt cagtgccagc agagcccagt gctggcaggc agcgccactt    120
tggtcgccct tggggcactg gccttgtacg tcgcgaagcc ctccggctac gggaagcaca    180
cggagagcct gaagccggcg gctacccgcc tgccagcccg cgccgcctgg ttcctgcagg    240
agctgccttc cttcgcggtg cccgcgggga tcctcgcccg gcagcccctc tccctcttcg    300
ggccacctgg gacggtactt ctgggcctct tctgcctaca ttacttccac aggacatttg    360
tgtactcact gctcaatcga gggaggcctt atccagctat actcattctc agaggcactg    420
ccttctgcac tggaaatgga gtccttcaag gctactatct gatttactgt gctgaatacc    480
ctgatgggtg gtacacagac atacggttta gcttgggtgt cttcttattt attttgggaa    540
tgggaataaa cattcatagt gactatatat gcgccagct caggaagcct ggagaaatca    600
gctacaggat tccacaaggt ggcttgttta cgtatgtttc tggagccaat ttcctcggtg    660
agatcattga atggatcggc tatgccctgg ccacttggtc cctcccagca cttgcatttg    720
catttttctc actttgtttc cttgggctgc gagcttttca ccaccatagg ttctacctca    780
agatgtttga ggactacccc aaatctcgga agcccttat tccattcatc ttttaaagga    840
accaaattaa aaaggagcag agctcccaca atgctgatga aaactgtcaa gctgctgaaa    900
ctgtaatttt catgatataa tagtcccgta tatatgtaat agtaggtctc ctggcgttct    960
gccagctggc ctggggattc tgagtggtgt ctgcttagag tttactccta cccttccagg    1020 gaccccctatc ctgatcccca actgaagctt caaaaagcca cttttccaaa tggcgacagt    1080
tgcttcttag ctattgctct gagaaagtac aaacttctcc tatgtctttc accgggcaat    1140
ccaagtacat gtggcttcat acccactccc tgtcaatgca ggacaactct gtaatcaaga    1200 atttttttgac ttgaaggcag tacttataga ccttattaaa ggtatgcatt ttatacatgt    1260
```

| | | |
|---|---|---|
| aacagagtag cagaaattta aactctgaag ccacaaagac ccagagcaaa cccactccca | 1320 |
| aatgaaaacc ccagtcatgg cttccttttt cttggttaat taggaaagat gagaaattat | 1380 |
| taggtagacc ttgaatacag gagccctctc ctcatagtgc tgaaaagata ctgatgcatt | 1440 |
| gacctcattt caaatttgtg cagtgtctta gttgatgagt gcctctgttt tccagaagat | 1500 |
| ttcacaatcc ccggaaaact ggtatggcta ttcttgaagg ccaggtttta ataaccacaa | 1560 |
| acaaaaaggc atgaacctgg gtggcttatg agagagtaga gaacaacatg accctggatg | 1620 |
| gctactaaga ggatagagaa cagttttaca atagacattg caaactctca tgttttttgga | 1680 |
| aactagtggc aatatccaaa taatgagtag tgtaaaacaa agagaattaa tgatgaggtt | 1740 |
| acatgctgct tgcctccacc agatgtccac aacaatatga agtacagcag aagccccaag | 1800 |
| caactttcct ttcctggagc ttcttccttg tagttctcag gacctgttca agaaggtgtc | 1860 |
| tcctagggc agcctgaatg cctccctcaa aggacctgca ggcagagact gaaaattgca | 1920 |
| gacagagggg cacgtctggg cagaaaacct gttttgtttg gctcagacat atagttttt | 1980 |
| tttttttac aaagtttcaa aaacttaaaa atcaggagat tccttcataa aactctagca | 2040 |
| ttctagtttc atttaaaaag ttggaggatc tgaacataca gagcccacat ttccacacca | 2100 |
| gaactggaac tacgtagcta gtaagcattt gagtttgcaa actcttgtga aggggtcacc | 2160 |
| ccagcatgag tgctgagata tggactctct aaggaagggg ccgaacgctt gtaattggaa | 2220 |
| tacatggaaa tatttgtctt ctcaggccta tgtttgcgga atgcattgtc aatatttagc | 2280 |
| aaactgtttt gacaaatgag caccagtggt actaagcaca gaaactcact atataagtca | 2340 |
| cataggaaac ttgaaaggtc tgaggatgat gtagattact gaaaaatgca aattgcaatc | 2400 |
| atataaataa gtgtttttgt tgttcattaa ataccttaa atcatg | 2446 |

<210> SEQ ID NO 673
<211> LENGTH: 8112
<212> TYPE: DNA
<213> ORGANISM: Artificial Sequence
<220> FEATURE:
<223> OTHER INFORMATION: NCBI Reference Sequence NM_001011645.2 669

<400> SEQUENCE: 673

| | | |
|---|---|---|
| gctgcgagca gagagggatt cctcggaggt catctgttcc atcttcttgc ctatgcaaat | 60 |
| gcctgcctga agctgctgga ggctggcttt gtaccggact ttgtacaggg aaccagggaa | 120 |
| acgaatgcag agtgctcctg acattgcctg tcactttttc ccatgatact ctggcttcac | 180 |
| agtttggaga ctgccaggga ccatgttttg cccattgact attactttcc accccagaag | 240 |
| acctgcctga tctgtggaga tgaagcttct gggtgtcact atggagctct cacatgtgga | 300 |
| agctgcaagg tcttcttcaa aagagccgct gaagggaaac agaagtacct gtgcgccagc | 360 |
| agaaatgatt gcactattga taaattccga aggaaaaatt gtccatcttg tcgtcttcgg | 420 |
| aaatgttatg aagcagggat gactctggga gcccggaagc tgaagaaact tggtaatctg | 480 |
| aaactacagg aggaaggaga ggcttccagc accaccagcc ccactgagga gacaacccag | 540 |
| aagctgacag tgtcacacat tgaaggctat gaatgtcagc ccatctttct gaatgtcctg | 600 |
| gaagccattg agccaggtgt agtgtgtgct ggacacgaca caaccagcc cgactccttt | 660 |
| gcagccttgc tctctagcct caatgaactg ggagagagac agcttgtaca cgtggtcaag | 720 |
| tgggccaagg ccttgcctgg cttccgcaac ttacacgtgg acgaccagat ggctgtcatt | 780 |
| cagtactcct ggatggggct catggtgttt gccatgggct ggcgatcctt caccaatgtc | 840 |
| aactccagga tgctctactt cgcccctgat ctggttttca atgagtaccg catgcacaag | 900 |

```
tcccggatgt acagccagtg tgtccgaatg aggcacctct ctcaagagtt tggatggctc    960
caaatcaccc cccaggaatt cctgtgcatg aaagcactgc tactcttcag cattattcca   1020
gtggatgggc tgaaaaatca aaaattcttt gatgaacttc gaatgaacta catcaaggaa   1080
ctcgatcgta tcattgcatg caaaagaaaa aatcccacat cctgctcaag acgcttctac   1140
cagctcacca agctcctgga ctccgtgcag cctattgcga gagagctgca tcagttcact   1200
tttgacctgc taatcaagtc acacatggtg agcgtggact ttccggaaat gatggcagag   1260
atcatctctg tgcaagtgcc caagatcctt tctgggaaag tcaagcccat ctatttccac   1320
acccagtgaa gcattggaaa ccctatttcc caccccagc tcatgccccc tttcagatgt   1380
cttctgcctg ttataactct gcactactcc tctgcagtgc cttggggaat tcctctatt   1440 gatgtacagt ctgtcatgaa catgttcctg aattctattt gctgggcttt tttttctct   1500 ttctctcctt tcttttctt cttccctccc tatctaaccc tcccatggca ccttcagact   1560 tgcttccca ttgtggctcc tatctgtgtt ttgaatggtg ttgtatgcct ttaaatctgt   1620
gatgatcctc atatggccca gtgtcaagtt gtgcttgttt acagcactac tctgtgccag   1680
ccacacaaac gtttacttat cttatgccac gggaagttta gagagctaag attatctggg   1740
gaaatcaaaa caaaacaag caaacaaaaa aaaaagcaa aacaaaaca aaaataagc   1800 caaaaaacct tgctagtgtt ttttcctcaa aaataaataa ataaataaat aaatacgtac   1860
atacatacac acatacatac aaacatatag aaatccccaa agaggccaat agtgacgaga   1920
aggtgaaaat tgcaggccca tggggagtta ctgattttt catctcctcc ctccacggga   1980
gactttattt tctgccaatg ctattgcca ttagagggca gagtgacccc agagctgagt   2040
tgggcagggg ggtggacaga gaggagagga caaggagggc aatggagcat cagtacctgc   2100
ccacagcctt ggtccctggg ggctagactg ctcaactgtg gagcaattca ttatactgaa   2160
aatgtgcttg ttgttgaaaa tttgtctgca tgttaatgcc tcaccccaa accctttct   2220 ctctcactct ctgcctccaa cttcagattg actttcaata gtttttctaa gacctttgaa   2280
ctgaatgttc tcttcagcca aaacttggcg acttccacag aaaagtctga ccactgagaa   2340
gaaggagagc agagatttaa ccctttgtaa ggccccattt ggatccaggt ctgctttctc   2400
atgtgtgagt cagggaggag ctggagccag aggagaagaa aatgatagct tggctgttct   2460
cctgcttagg acactgactg aatagttaaa ctctcactgc cactaccttt tccccaccctt   2520 taaaagacct gaatgaagtt ttctgccaaa ctccgtgaag ccacaagcac cttatgtcct   2580
cccttcagtg ttttgtgggc ctgaatttca tcacactgca tttcagccat ggtcatcaag   2640
cctgtttgct tcttttgggc atgttcacag attctctgtt aagagccccc accaccaaga   2700
aggttagcag gccaacagct ctgacatcta tctgtagatg ccagtagtca caagatttc   2760 ttaccaactc tcagatcgct ggagccctta gacaaactgg aaagaaggca tcaaagggat   2820
caggcaagct gggcgtcttg cccttgtccc ccagagatga taccctccca gcaagtggag   2880
aagttctcac ttccttcttt agagcagcta aaggggctac ccagatcagg gttgaagaga   2940
aaactcaatt accagggtgg gaagaatgaa ggcactagaa ccagaaaccc tgcaaatgct   3000
cttcttgtca cccagcatat ccacctgcag aagtcatgag aagagagaag gaacaaagag   3060
gagactctga ctactgaatt aaaatcttca gcggcaaagc ctaaagccag atggacacca   3120
tctggtgagt ttactcatca tcctcctctg ctgctgattc tgggctctga cattgcccat   3180
actcactcag attccccacc tttgttgctg cctcttagtc agagggaggc caaaccattg   3240
```

```
agactttcta cagaaccatg gcttctttcg gaaaggtctg gttggtgtgg ctccaatact    3300
ttgccaccca tgaactcagg gtgtgccctg ggacactggt tttatatagt cttttggcac    3360
acctgtgttc tgttgacttc gttcttcaag cccaagtgca agggaaaatg tccacctact    3420
ttctcatctt ggcctctgcc tccttactta gctcttaatc tcatctgttg aactcaagaa    3480
atcaagggcc agtcatcaag ctgcccattt taattgattc actctgtttg ttgagaggat    3540
agtttctgag tgacatgata tgatccacaa gggtttcctt ccctgatttc tgcattgata    3600
ttaatagcca aacgaacttc aaaacagctt taaataacaa gggagagggg aacctaagat    3660
gagtaatatg ccaatccaag actgctggag aaaactaaag ctgacaggtt cccttttgg     3720
ggtgggatag acatgttctg gttttcttta ttattacaca atctggctca tgtacaggat    3780
cacttttagc tgtttaaac  agaaaaaaat atccaccact cttttcagtt acactaggtt    3840
acatttaat  aggtccttta catctgtttt ggaatgattt tcatcttttg tgatacacag    3900
attgaattat atcattttca tatctctcct tgtaaatact agaagctctc ctttacattt    3960
ctctatcaaa tttttcatct ttatgggttt cccaattgtg actcttgtct tcatgaatat    4020
atgttttca  tttgcaaaag ccaaaaatca gtgaaacagc agtgtaatta aaagcaacaa    4080
ctggattact ccaaatttcc aaatgacaaa actagggaaa aatagcctac acaagccttt    4140
aggcctactc tttctgtgct tgggtttgag tgaacaaagg agattttagc ttggctctgt    4200
tctcccatgg atgaaggag  gaggattttt tttttctttt ggccattgat gttctagcca    4260
atgtaattga cagaagtctc attttgcatg cgctctgctc tacaaacaga gttggtatgg    4320
ttggtatact gtactcacct gtgagggact ggccactcag acccacttag ctggtgagct    4380
agaagatgag gatcactcac tggaaaagtc acaaggacca tctccaaaca agttggcagt    4440
gctcgatgtg gacgaagagt gaggaagaga aaagaaggag caccaggga  gaaggctccg    4500
tctgtgctgg gcagcagaca gctgccagga tcacgaactc tgtagtcaaa gaaaagagtc    4560
gtgtggcagt ttcagctctc gttcattggg cagctcgcct aggcccagcc tctgagctga    4620
catgggagtt gttggattct ttgtttcata gcttttccta tgccataggc aatattgttg    4680
ttcttggaaa gttattatt  ttttaactc  ccttactctg agaaagggat attttgaagg    4740
actgtcatat atctttgaaa aagaaaatc  tgtaatacat atattttat  gtatgttcac    4800
tggcactaaa aaatatagag agcttcattc tgtcctttgg gtagttgctg aggtaattgt    4860
ccaggttgaa aaataatgtg ctgatgctag agtccctctc tgtccatact ctacttctaa    4920
atacatatag gcatacatag caagttttat ttgacttgta ctttaagaga aaatatgtcc    4980
accatccaca tgatgcacaa atgagctaac attgagcttc aagtagcttc taagtgtttg    5040
tttcattagg cacagcacag atgtggcctt tcccccttc  tctcccttga tatctggcag    5100
ggcataaagg cccaggccac ttcctctgcc ccttcccagc cctgcaccaa agctgcattt    5160
caggagactc tctccagaca gcccagtaac tacccgagca tggcccctgc atagccctgg    5220
aaaaataaga ggctgactgt ctacgaatta tcttgtgcca gttgcccagg tgagagggca    5280
ctgggccaag ggagtggttt tcatgtttga cccactacaa ggggtcatgg gaatcaggaa    5340
tgccaaagca ccagatcaaa tccaaaactt aaagtcaaaa taagccattc agcatgttca    5400
gtttcttgga aaaggaagtt tctacccctg atgcctttgt aggcagatct gttctcacca    5460
ttaatctttt tgaaaatctt ttaaagcagt ttttaaaaag agagatgaaa gcatcacatt    5520
atataaccaa agattacatt gtacctgcta agataccaaa attcataagg gcaggggggg    5580
agcaagcatt agtgcctctt tgataagctg tccaaagaca gactaaagga ctctgctggt    5640
```

```
gactgactta taagagcttt gtgggttttt ttttccctaa taatatacat gtttagaaga    5700
attgaaaata atttcgggaa aatgggatta tgggtccttc actaagtgat tttataagca    5760
gaactggctt tccttttctc tagtagttgc tgagcaaatt gttgaagctc catcattgca    5820
tggttggaaa tggagctgtt cttagccact gtgtttgcta gtgcccatgt tagcttatct    5880
gaagatgtga aacccttgct gataagggag catttaaagt actagatttt gcactagagg    5940
gacagcaggc agaaatcctt atttctgccc actttggatg gcacaaaaag ttatctgcag    6000
ttgaaggcag aaagttgaaa tacattgtaa atgaatattt gtatccatgt ttcaaaattg    6060
aaatatatat atatatatat atatatatat atatatatat atagtgtgtg tgtgtgttct    6120
gatagcttta actttctctg catctttata tttggttcca gatcacacct gatgccatgt    6180
acttgtgaga gaggatgcag ttttgttttg gaagctctct cagaacaaac aagacacctg    6240
gattgatcag ttaactaaaa gttttctccc ctattgggtt tgacccacag gtcctgtgaa    6300
ggagcagagg gataaaaaga gtagaggaca tgatacattg tactttacta gttcaagaca    6360
gatgaatgtg gaaagcataa aaactcaatg gaactgactg agatttacca cagggaaggc    6420
ccaaacttgg ggccaaaagc ctacccaagt gattgaccag tggcccccta atgggacctg    6480
agctgttgga agaagagaac tgttccttgg tcttcaccat ccttgtgaga gaagggcagt    6540
ttcctgcatt ggaacctgga gcaagcgctc tatctttcac acaaattccc tcacctgaga    6600
ttgaggtgct cttgttactg ggtgtctgtg tgctgtaatt ctggttttgg atatgttctg    6660
taaagatttt gacaaatgaa aatgtgtttt tctctgttaa aacttgtcag agtactagaa    6720
gttgtatctc tgtaggtgca ggtccatttc tgcccacagg tagggtgttt ttctttgatt    6780
aagagattga cacttctgtt gcctaggacc tcccaactca accatttcta ggtgaaggca    6840
gaaaaatcca cattagttac tcctcttcag acatttcagc tgagataaca aatcttttgg    6900 aatttttca cccatagaaa gagtggtaga tatttgaatt tagcaggtgg agtttcatag    6960
taaaaacagc ttttgactca gctttgattt atcctcattt gatttggcca gaaagtaggt    7020
aatatgcatt gattggcttc tgattccaat tcagtatagc aaggtgctag gttttttcct    7080
ttccccacct gtctcttagc ctggggaatt aaatgagaag ccttagaatg ggtggccctt    7140
gtgacctgaa acacttccca cataagctac ttaacaagat tgtcatggag ctgcagattc    7200
cattgcccac caaagactag aacacacaca tatccataca ccaaaggaaa gacaattctg    7260
aaatgctgtt tctctggtgg ttccctctct ggctgctgcc tcacagtatg ggaacctgta    7320
ctctgcagag gtgacaggcc agatttgcat tatctcacaa ccttagccct tggtgctaac    7380
tgtcctacag tgaagtgcct ggggggttgt cctatcccat aagccacttg gatgctgaca    7440
gcagccacca tcagaatgac ccacgcaaaa aaagaaaaa aaaaattaaa aagtcccctc    7500
acaacccagt gacacctttc tgctttcctc tagactggaa cattgattag ggagtgcctc    7560
agacatgaca ttcttgtgct gtccttggaa ttaatctggc agcaggaggg agcagactat    7620
gtaaacagag ataaaaatta attttcaata ttgaaggaaa aagaaataa gaagagagag    7680 agaaagaaag catcacacaa agattttctt aaaagaaaca attttgcttg aaatctcttt    7740
agatggggct catttctcac ggtggcactt ggcctccact gggcagcagg accagctcca    7800
agcgctagtg ttctgttctc tttttgtaat cttggaatct tttgttgctc taaatacaat    7860
taaaaatggc agaaacttgt tgttggact acatgtgtga ctttgggtct gtctctgcct    7920
ctgctttcag aaatgtcatc cattgtgtaa aatattggct tactggtctg ccagctaaaa    7980
cttggccaca tcccctgtta tggctgcagg atcgagttat tgttaacaaa gagacccaag    8040
```

```
aaaagctgct aatgtcctct tatcattgtt gttaatttgt taaaacataa agaaatctaa    8100
aatttcaaaa aa                                                       8112
```